(12) United States Patent
de los Reyes

(10) Patent No.: US 9,599,594 B2
(45) Date of Patent: Mar. 21, 2017

(54) STACKABLE PLANAR ADSORPTIVE DEVICES

(71) Applicant: SPF Technologies LLC, Somerville, MA (US)

(72) Inventor: Gaston de los Reyes, Somerville, MA (US)

(73) Assignee: SPF TECHNOLOGIES LLC, Somerville, MA (US)

( * ) Notice: Subject to any disclaimer, the term of this patent is extended or adjusted under 35 U.S.C. 154(b) by 0 days.

(21) Appl. No.: 14/907,804

(22) PCT Filed: Aug. 12, 2014

(86) PCT No.: PCT/US2014/050743
§ 371 (c)(1),
(2) Date: Jan. 26, 2016

(87) PCT Pub. No.: WO2015/023678
PCT Pub. Date: Feb. 19, 2015

(65) Prior Publication Data
US 2016/0161453 A1 Jun. 9, 2016

Related U.S. Application Data

(63) Continuation-in-part of application No. 13/964,726, filed on Aug. 12, 2013, now Pat. No. 9,120,037.
(Continued)

(51) Int. Cl.
*G01N 30/52* (2006.01)
*B01D 15/20* (2006.01)
(Continued)

(52) U.S. Cl.
CPC ......... *G01N 30/52* (2013.01); *B01D 15/1842* (2013.01); *B01D 15/206* (2013.01);
(Continued)

(58) Field of Classification Search
CPC ............... G01N 30/52; G01N 30/6047; G01N 2030/528; G01N 2030/527; B01D 15/206;
(Continued)

(56) References Cited

U.S. PATENT DOCUMENTS 3,340,085 A * 9/1967 Halasz ...................... B01J 20/06
428/403
3,422,604 A * 1/1969 Haase ...................... G01N 30/38
96/102

(Continued)

FOREIGN PATENT DOCUMENTS

| GB | WO 92/03206 A1 | 3/1992 |
| JP | A 2006-90813 | 4/2006 |
| JP | A 2010-8410 | 1/2010 |

OTHER PUBLICATIONS

Maksimova, E.F., et al. "Methacrylate-based monolithic layers for planar chromatography of polymers," Journal of Chromatography A, 1218: 2425-2431 (2011). Available online Dec. 21, 2010.*
(Continued)

*Primary Examiner* — Katherine Zalasky
*Assistant Examiner* — Benjamin Lebron
(74) *Attorney, Agent, or Firm* — Barry Gaiman

(57) ABSTRACT

Adsorptive bed devices include a scaffold in housing having a stress absorbing rigid structure and open cells filled with adsorptive beads. The scaffold restricts movement of the plurality of adsorptive beads, absorbs stress induced by a hydraulic pressure gradient along a direction of liquid flow and transfers a portion of the induced compressive stress to the housing. In one embodiment the adsorptive bed is packed into a chromatography column, and in another embodiment the adsorptive bed is sealed in a monolithic block. In another embodiment, the adsorptive bed device includes an adsorptive block, first and second planar distributors and peripheral seal. The adsorptive media includes
(Continued)

multiple layers of planarly cohesive media and when operated in a shallow bed configuration possesses significant tensile strength along its planar dimensions enabling it to support the hydraulic pressures that will be generated by the fluids being processed through the adsorptive devices.

22 Claims, 38 Drawing Sheets

Related U.S. Application Data

(60) Provisional application No. 61/979,105, filed on Apr. 14, 2014.

(51) Int. Cl.

| | |
|---|---|
| *B01D 15/18* | (2006.01) |
| *B01D 15/22* | (2006.01) |
| *B01J 20/28* | (2006.01) |
| *B33Y 80/00* | (2015.01) |
| *G01N 30/60* | (2006.01) |
| *B01J 20/282* | (2006.01) |

(52) U.S. Cl.
CPC .............. *B01D 15/22* (2013.01); *B33Y 80/00* (2014.12); *G01N 30/6047* (2013.01); *B01J 20/282* (2013.01); *B01J 20/28016* (2013.01); *B01J 20/28042* (2013.01); *G01N 2030/527* (2013.01); *G01N 2030/528* (2013.01)

(58) Field of Classification Search
CPC ................. B01D 15/22; B01D 15/1842; B01J 20/28028; B01J 20/282; B01J 20/28033; B01J 20/28016; B01J 20/28042; B33Y 80/00

See application file for complete search history.

(56) References Cited

U.S. PATENT DOCUMENTS

| | | | | | |
|---|---|---|---|---|---|
| 4,971,736 | A | * | 11/1990 | Hagen | ................ B01J 20/28028 |
| | | | | | 264/175 |
| 5,683,916 | A | * | 11/1997 | Goffe | .................... B01D 61/00 |
| | | | | | 210/198.3 |
| 5,800,706 | A | * | 9/1998 | Fischer | .................. B01D 39/06 |
| | | | | | 210/198.2 |
| 7,947,175 | B2 | | 5/2011 | Shinkazh | |
| 7,988,859 | B2 | | 8/2011 | Shinkazh | |
| 2001/0032814 | A1 | * | 10/2001 | Kearney | ................ B01D 15/14 |
| | | | | | 210/284 |
| 2003/0150806 | A1 | * | 8/2003 | Hobbs | ................. B01F 13/0059 |
| | | | | | 210/635 |
| 2005/0006293 | A1 | | 1/2005 | Koehler | |
| 2008/0135484 | A1 | | 6/2008 | Hammer | |
| 2008/0148936 | A1 | * | 6/2008 | Baksh | .................... B01D 53/02 |
| | | | | | 95/47 |
| 2008/0236389 | A1 | * | 10/2008 | Leedy | .................... B01D 53/02 |
| | | | | | 95/95 |
| 2008/0283458 | A1 | | 11/2008 | Ishii | |
| 2009/0321338 | A1 | * | 12/2009 | Natarajan | .......... B01D 15/1864 |
| | | | | | 210/198.3 |
| 2010/0187167 | A1 | | 7/2010 | Reinbigler | |
| 2010/0222570 | A1 | * | 9/2010 | Ratnam | .................... C07H 5/02 |
| | | | | | 536/127 |
| 2012/0097591 | A1 | | 4/2012 | Berthold | |
| 2012/0118807 | A1 | | 5/2012 | Natarajan | |
| 2013/0020263 | A1 | | 1/2013 | Gebauer | |
| 2013/0068671 | A1 | | 3/2013 | Gebauer | |

OTHER PUBLICATIONS

Svec, F., et al. "Molded rigid monolithic porous polymers: an inexpensive, efficient, and versatile alternative to beads for the design of materials for numerous applications," Ind. Eng. Chem. Res., 38: 34-48 (1999).*

Siwak, M., et al. "Integration of a novel modular chromatography scaffold and resin design to achieve a Hyper ProductiveTM Protein A capture process". PowerPoint slides. Presented at ACS BIOT San Diego, Mar. 13-17, 2016.*

International Search Report and the Written Opinion, PCT/US2014050743, Nov. 20, 2014, pp. 10.

* cited by examiner

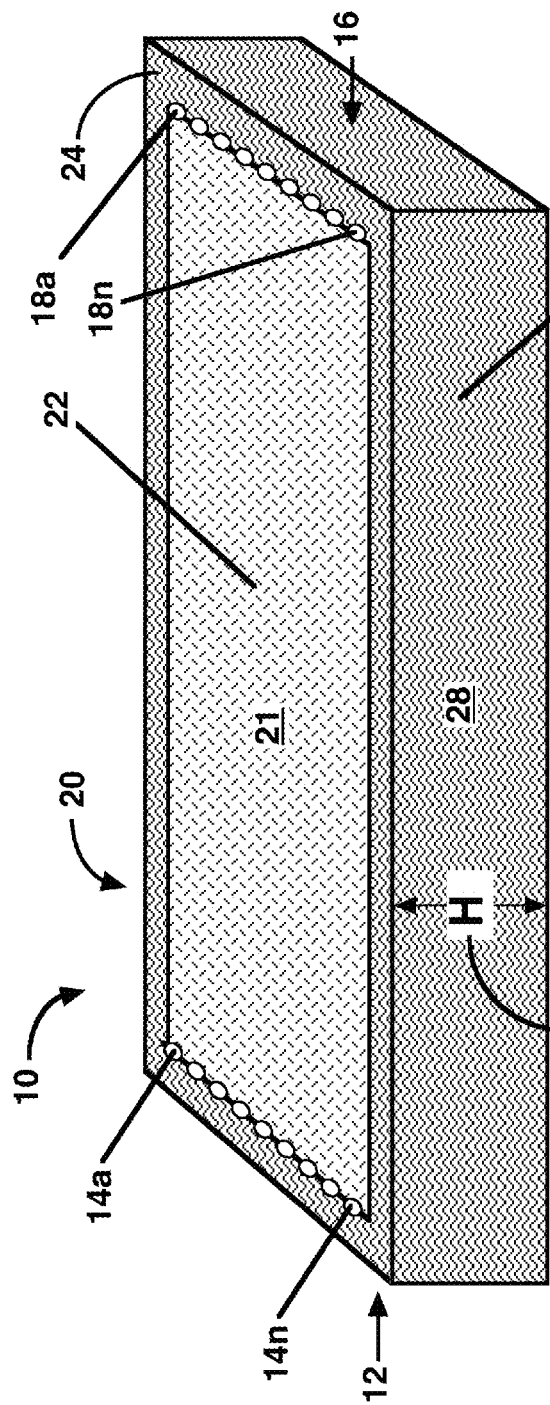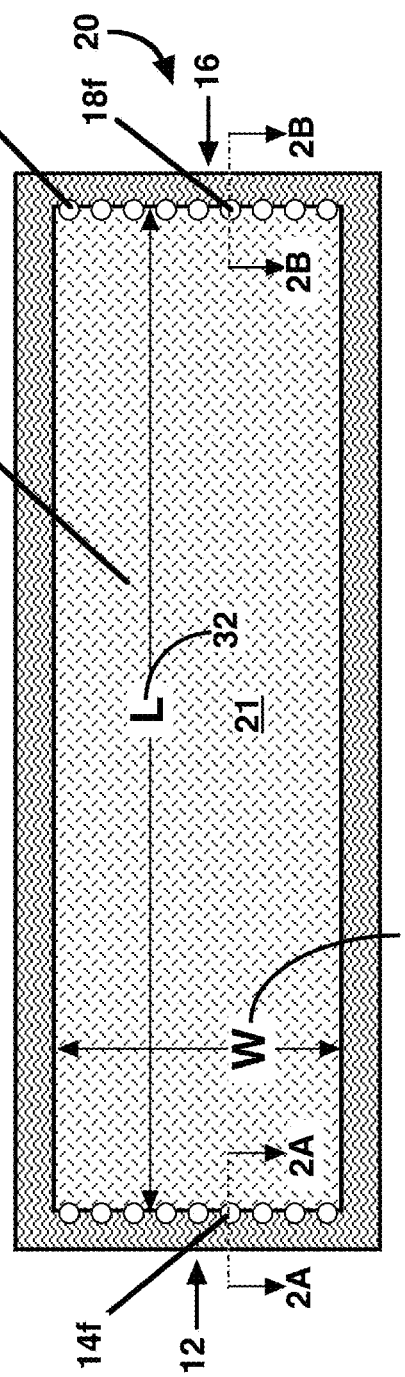

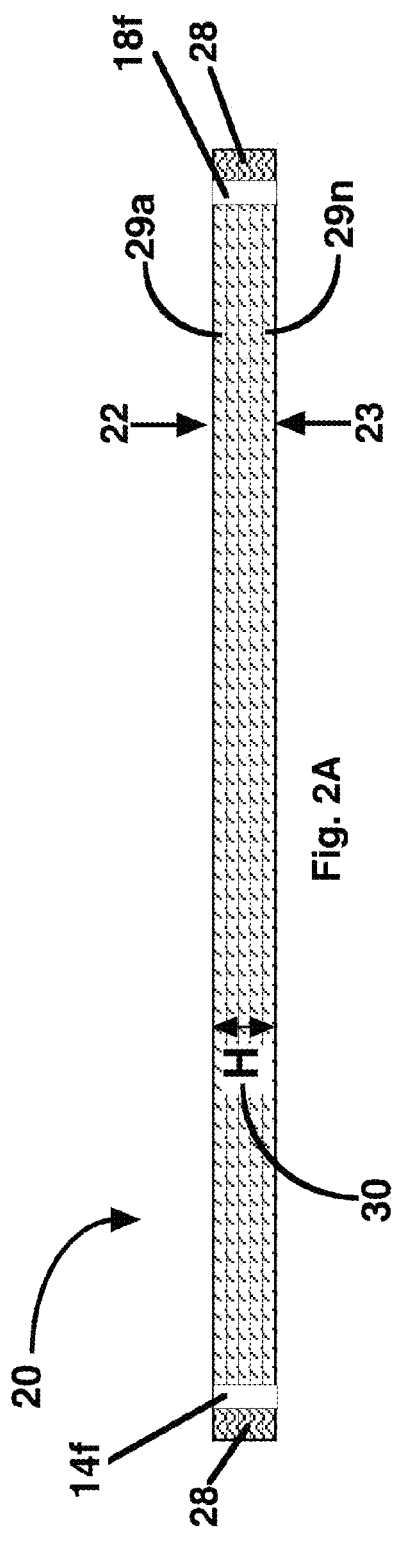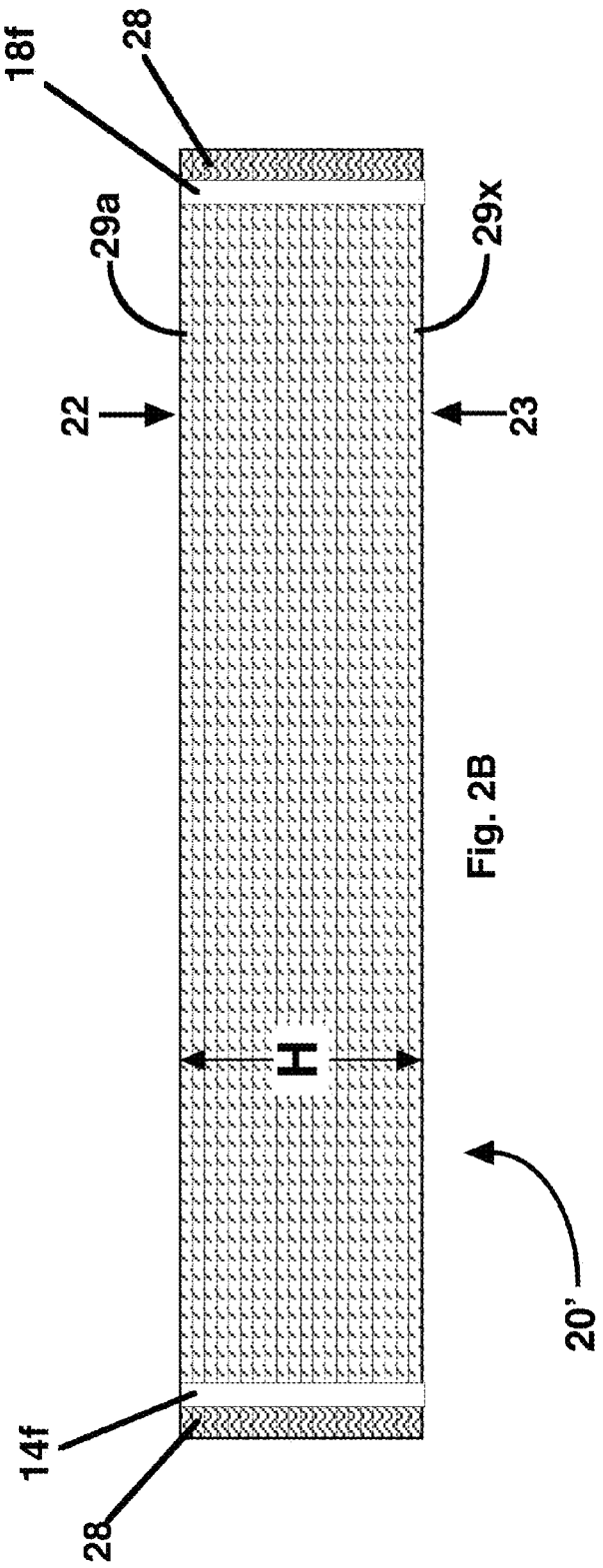

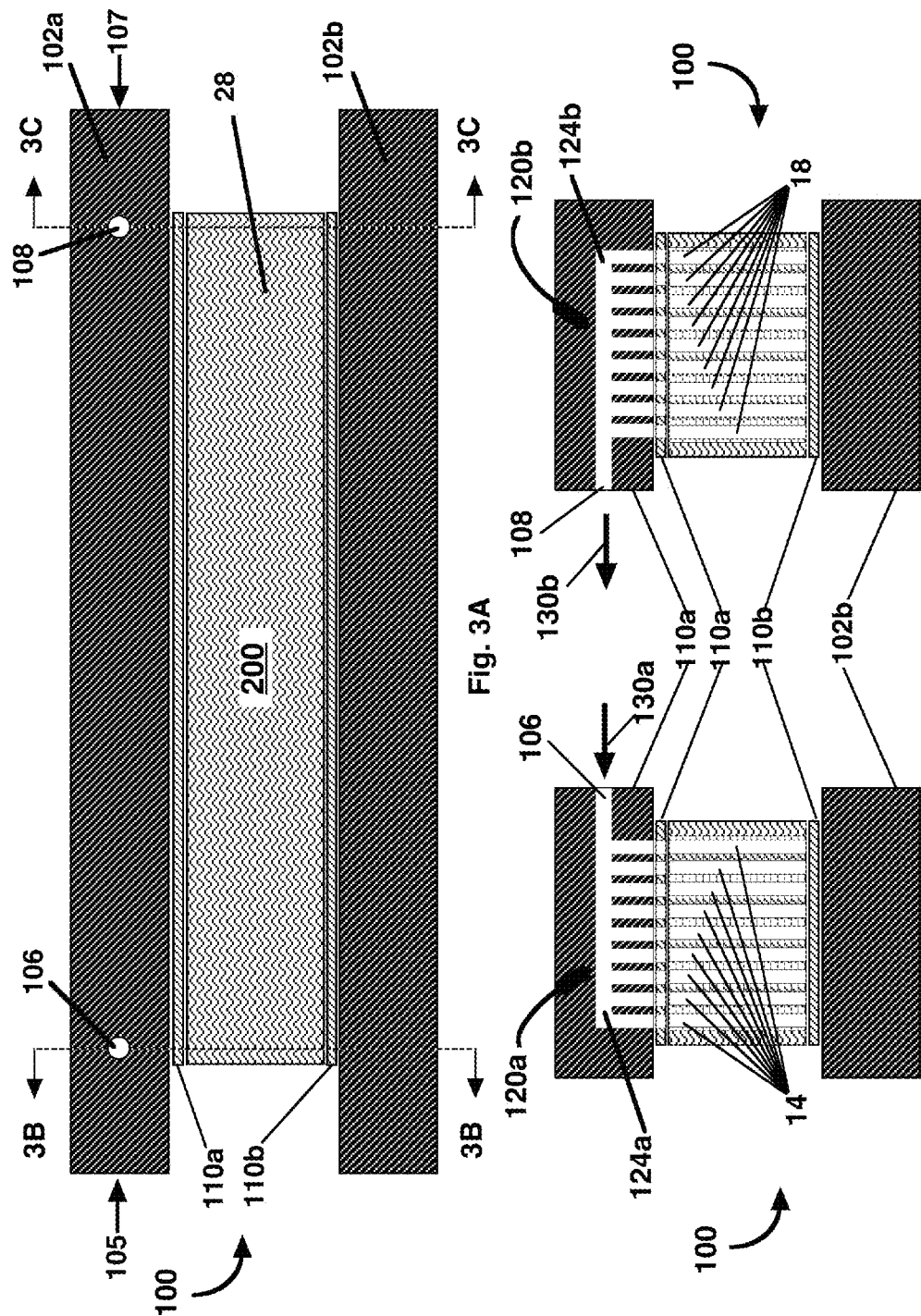

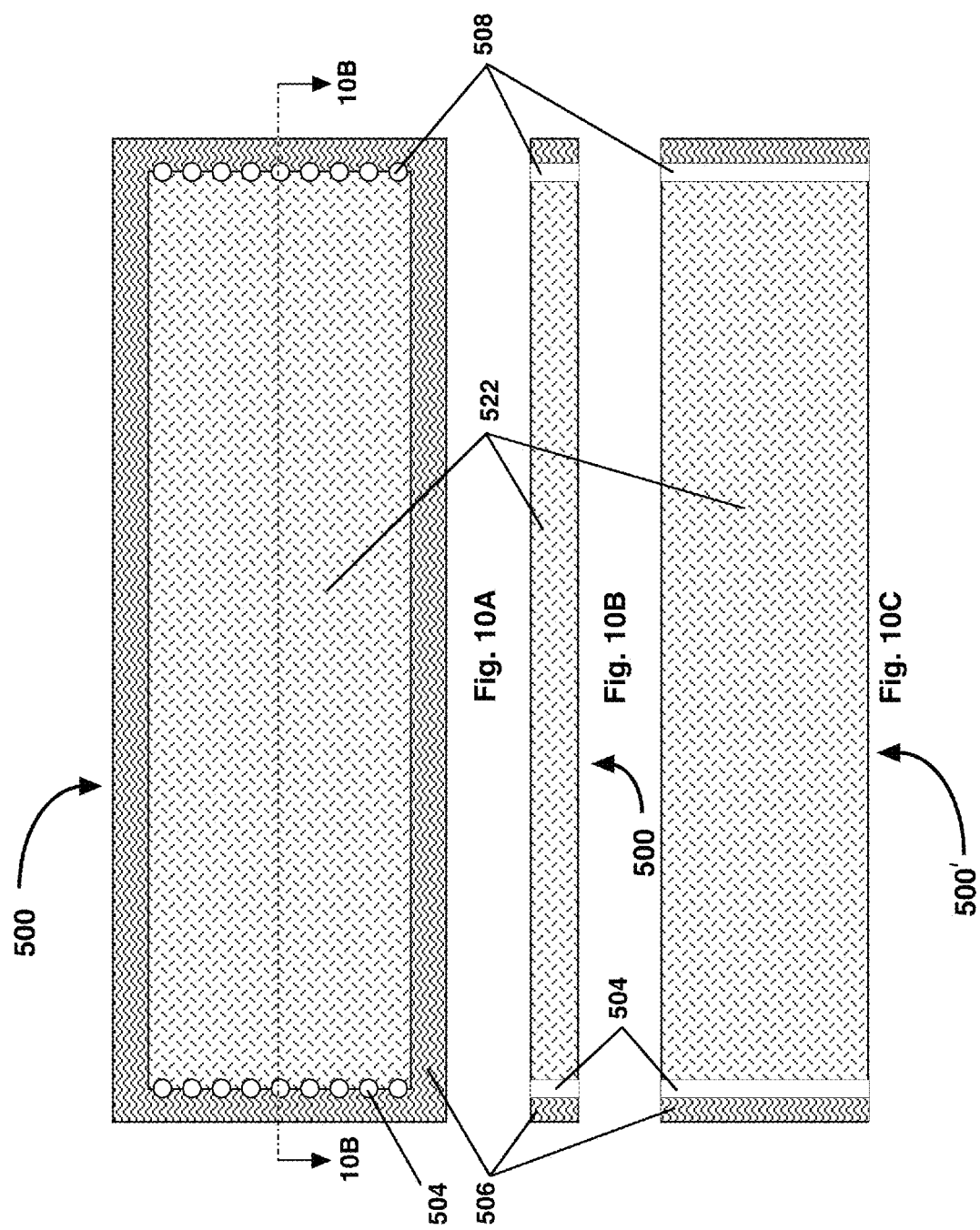

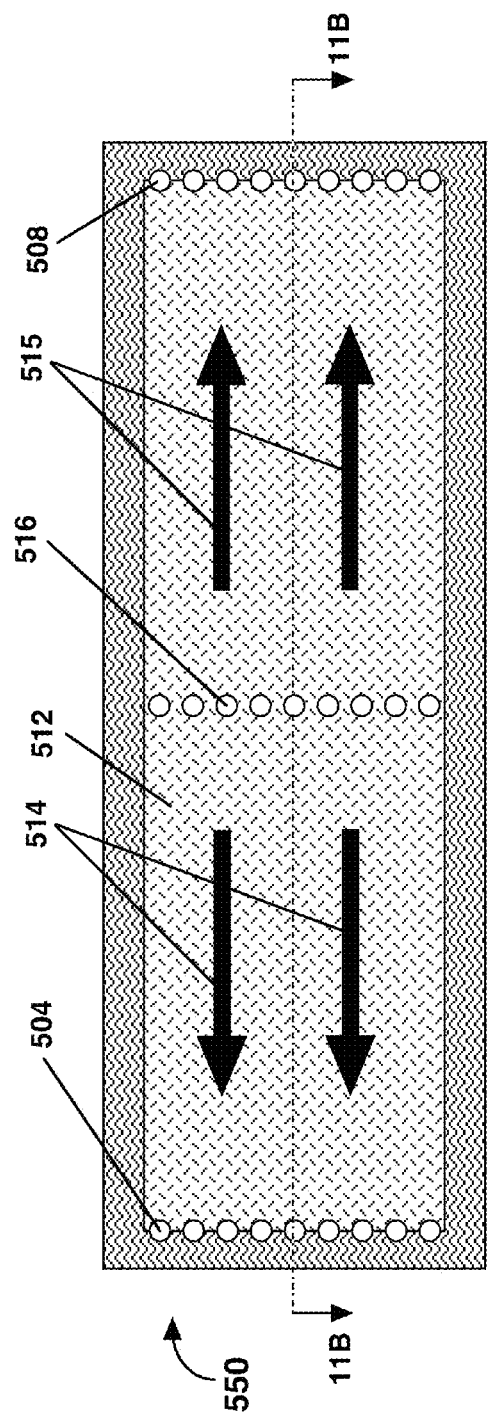
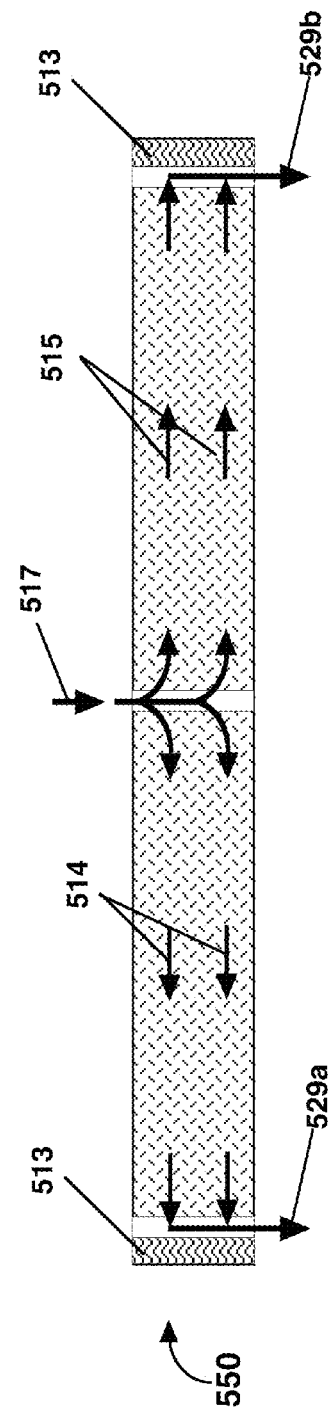

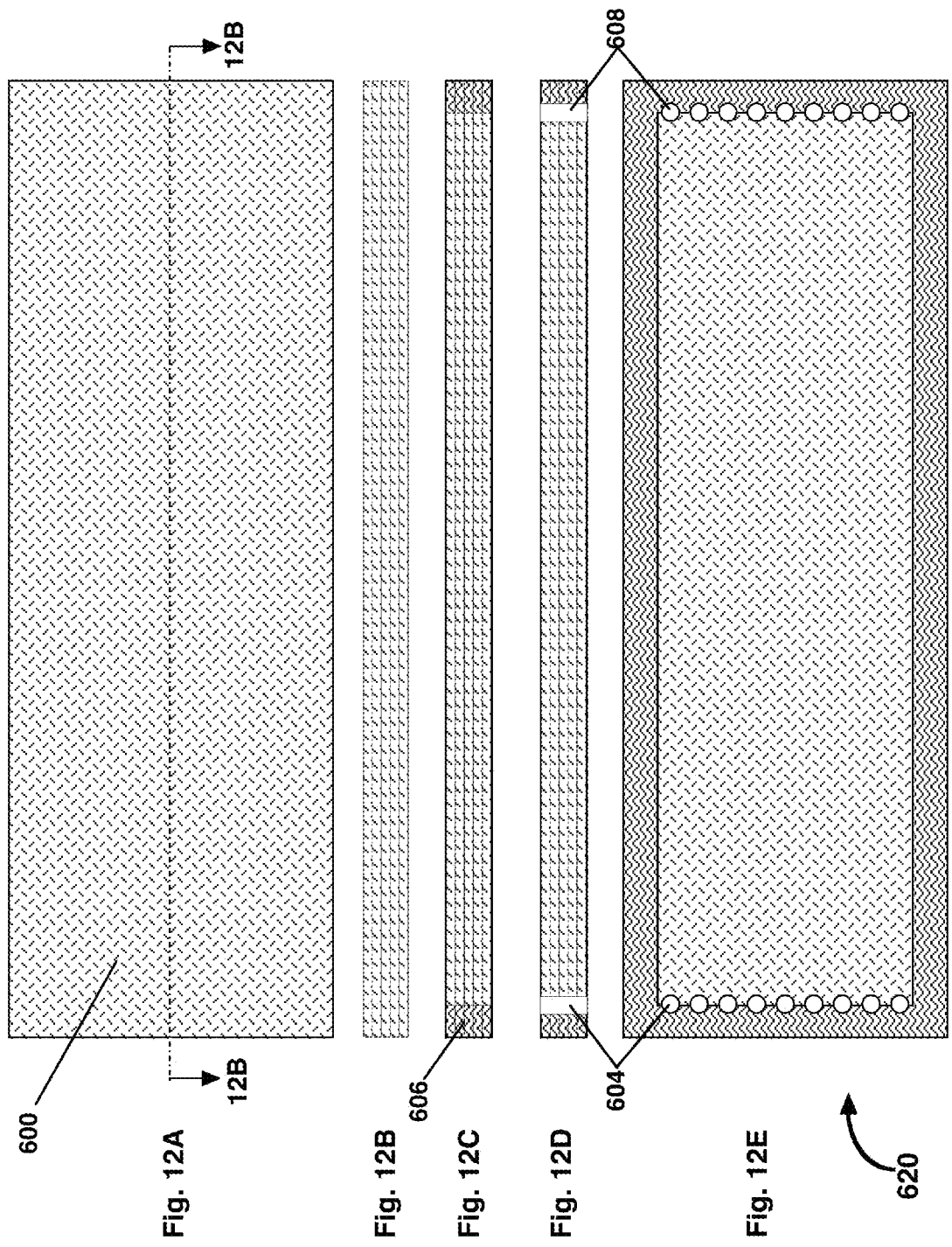

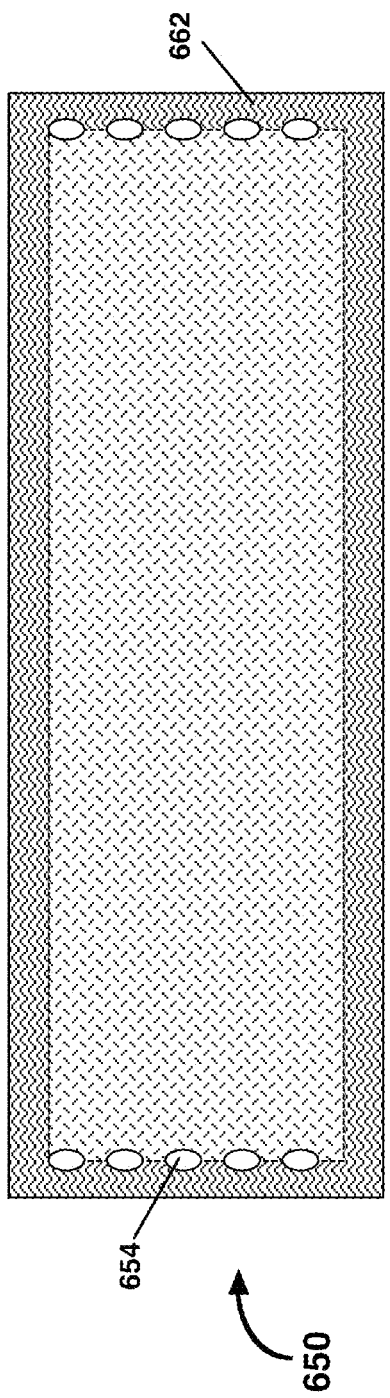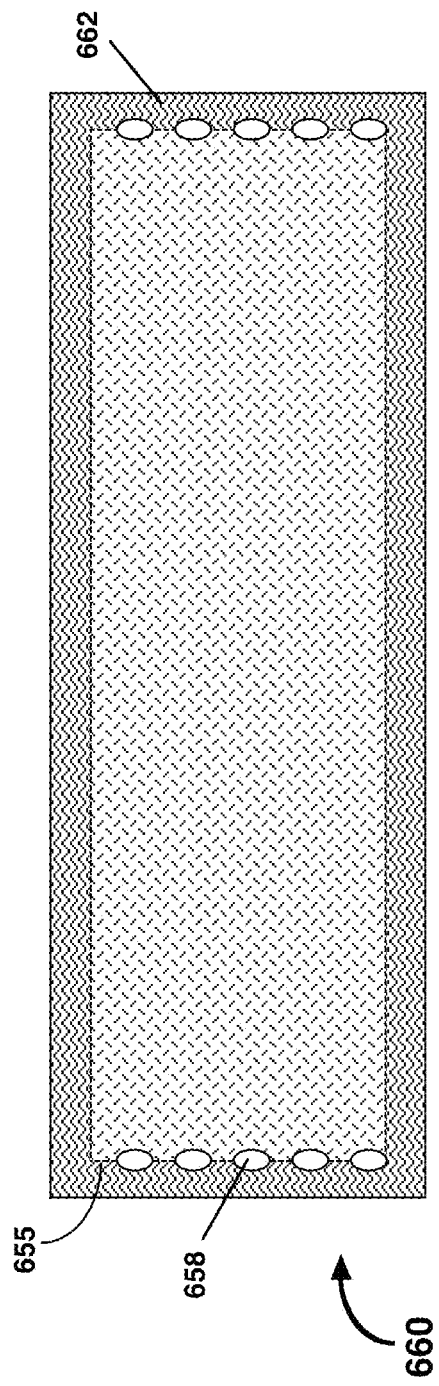

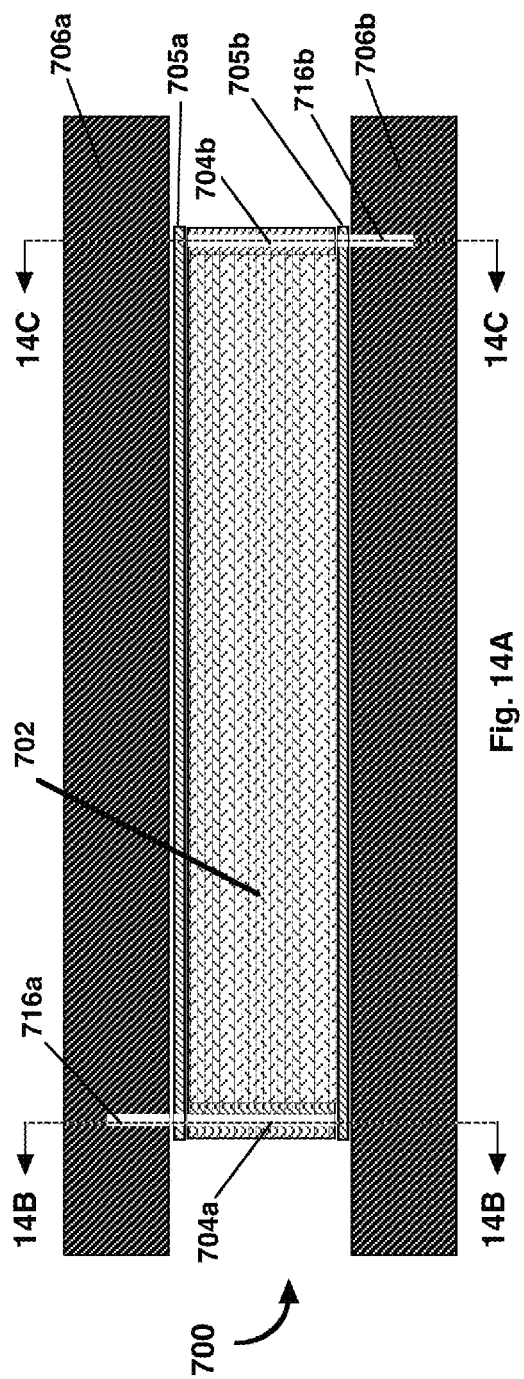
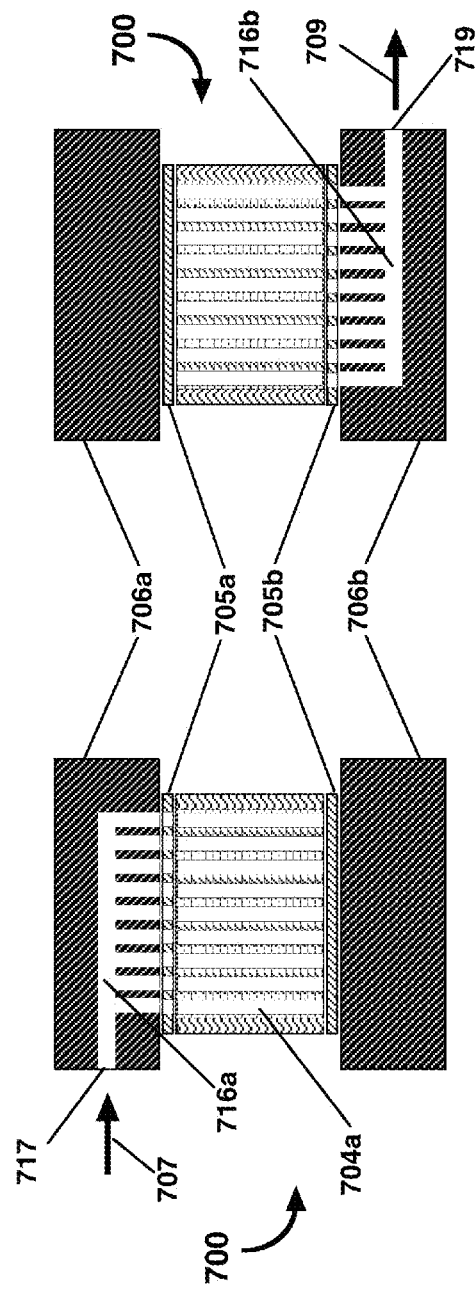
Fig. 14A
Fig. 14B
Fig. 14C

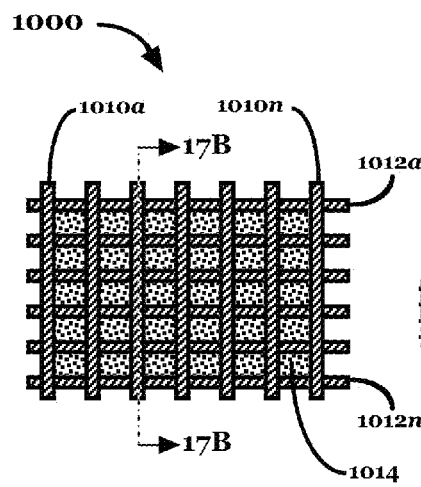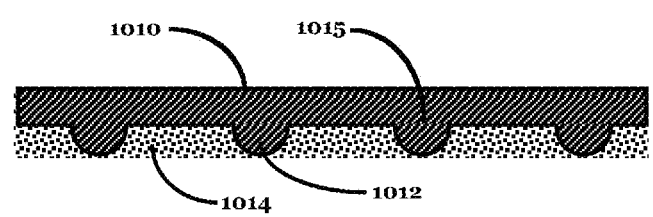
Fig. 17A  Fig. 17B
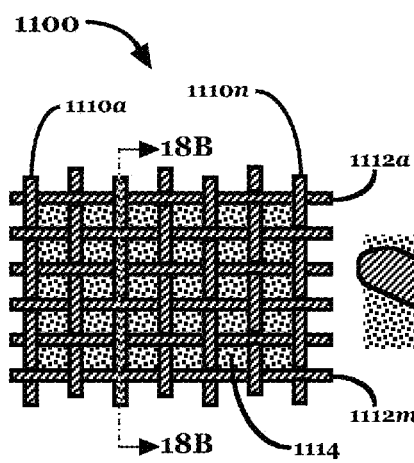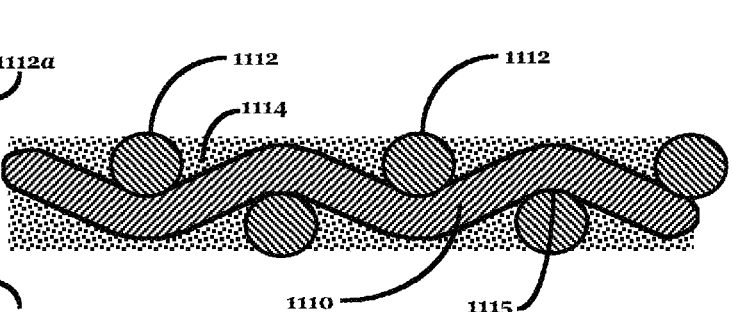
Fig. 18A  Fig. 18B

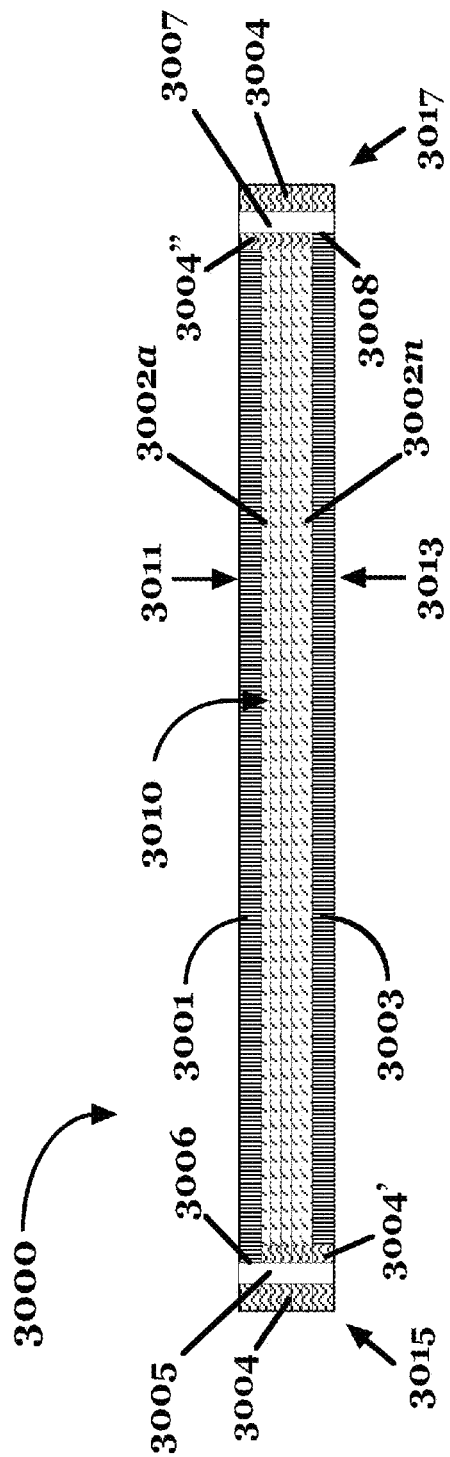
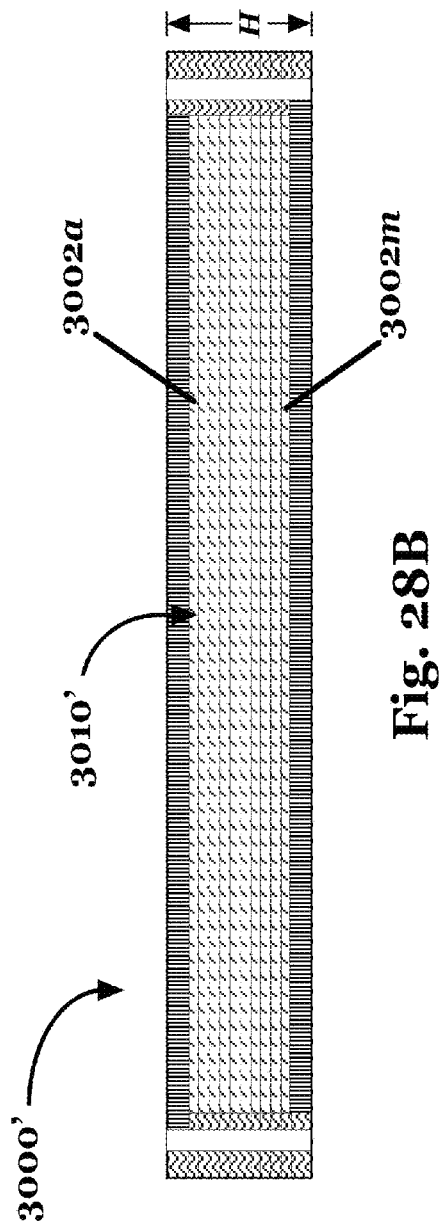
Fig. 28A
Fig. 28B

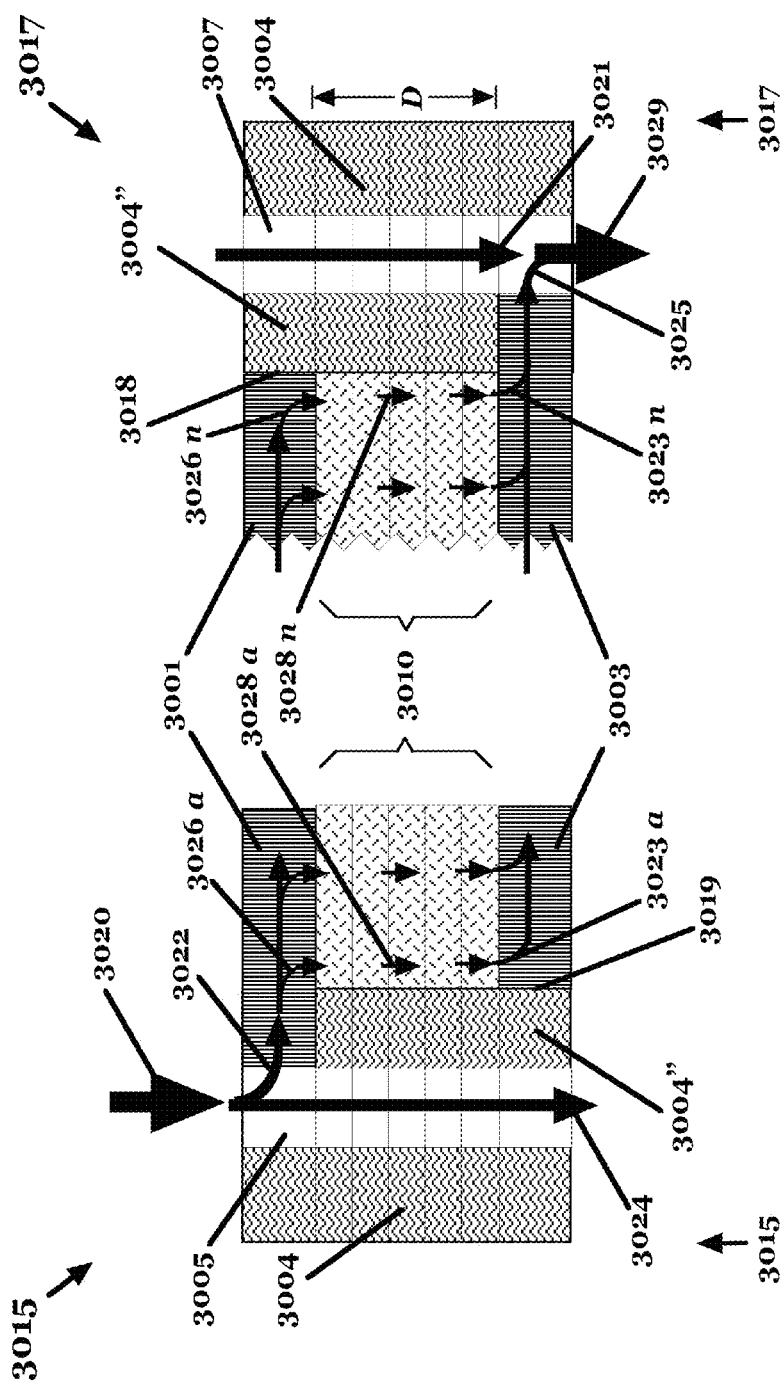

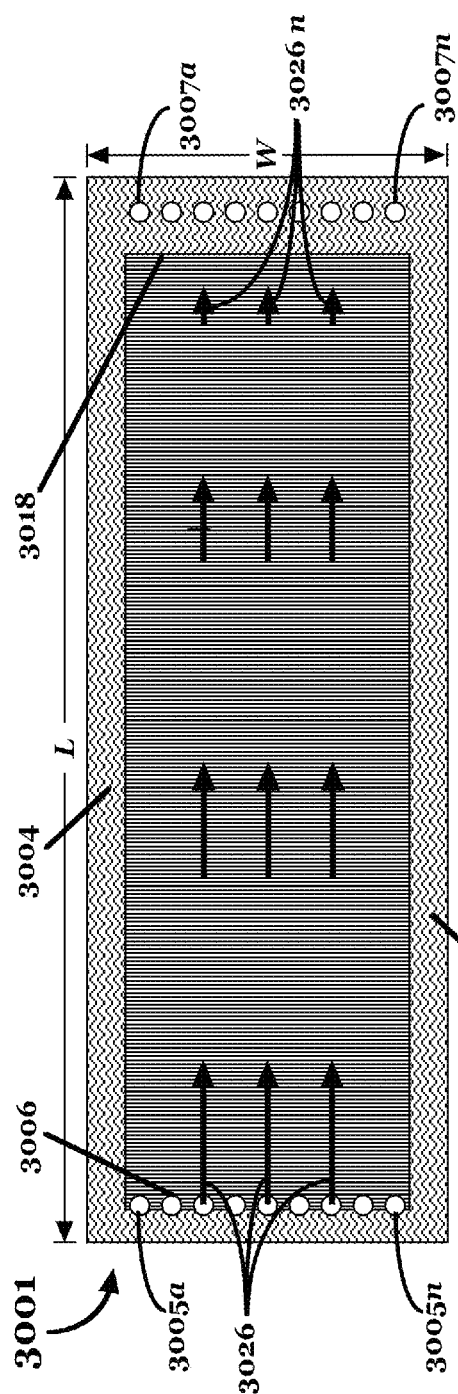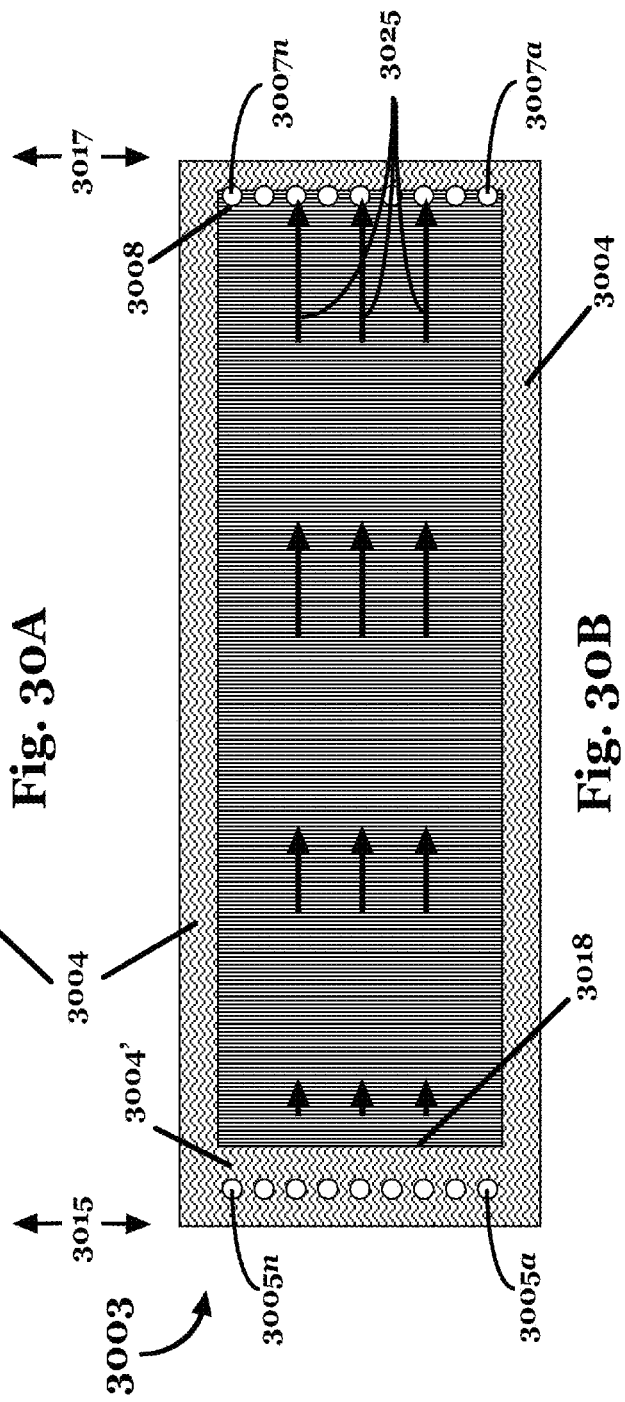
Fig. 30A
Fig. 30B

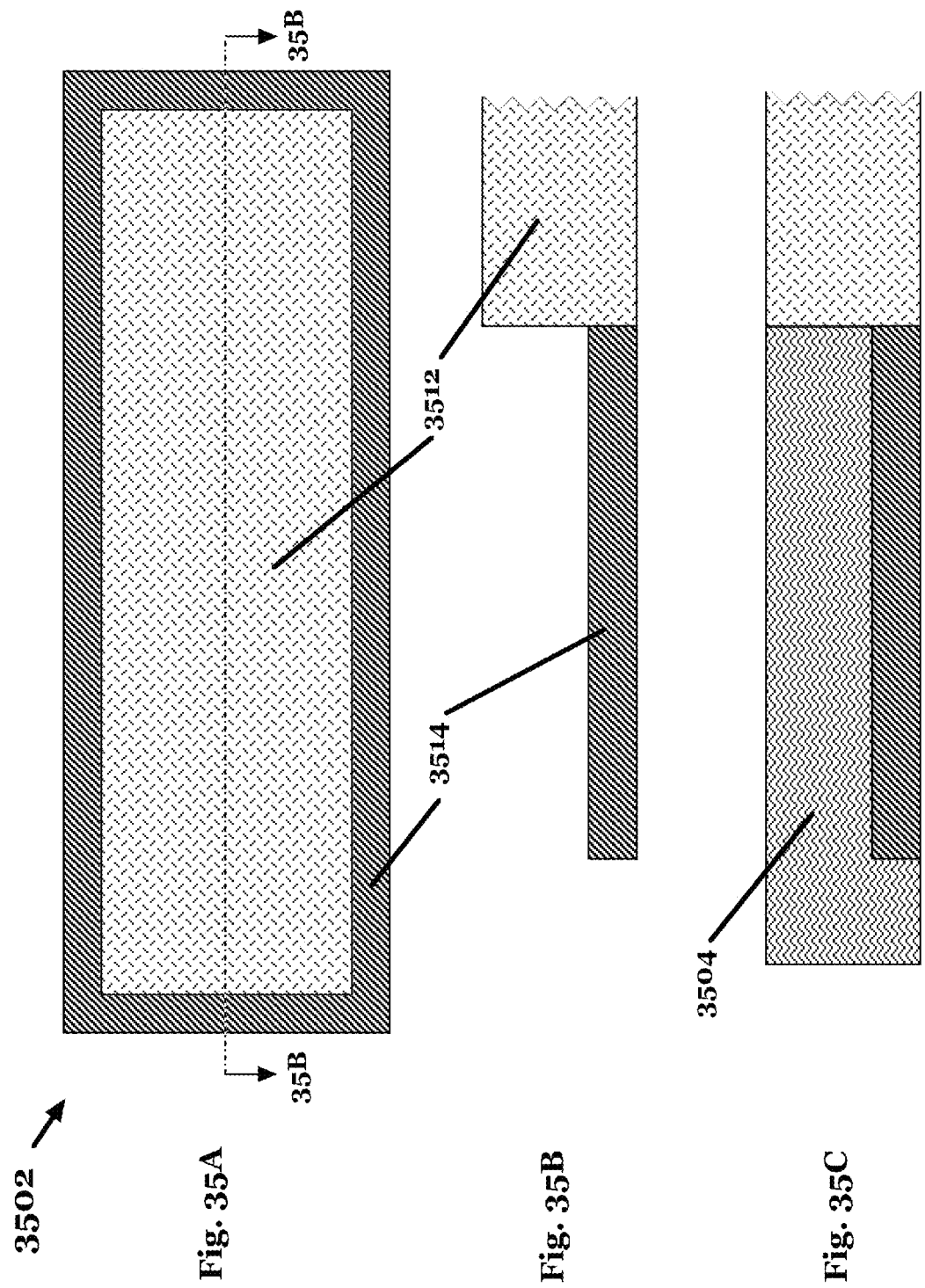

STACKABLE PLANAR ADSORPTIVE DEVICES

TECHNICAL FIELD

The field of this invention is related to adsorptive devices and processes, of which chromatography is an example. More specifically, this invention relates to devices having shallow adsorptive beds.

BACKGROUND OF THE INVENTION

Adsorptive processes and devices are widely used in the analysis and purification of chemicals, including synthetic and naturally-derived pharmaceuticals, blood products and recombinant proteins.

Chromatography is a general separation technique that relies on the relative affinity or distribution of the molecules of interest between a stationary phase and a mobile phase for molecular separation. The stationary phase typically comprises a porous media imbibed with solvent. The mobile phase comprises a solvent, which can be aqueous or organic, that flows through the interstitial space that exists between the spaces occupied by the stationary phase.

Columns with associated end caps, fittings and tubing are the most common configuration, with the media packed into the tube or column. The mobile phase is pumped through the column. The sample is introduced at one end of the column, the feed end, and the various components interact with the stationary phase by any one of a multitude of adsorptive phenomena. The differential adsorptive interaction between the components and media leads them to traverse the column at different velocities, which results in a physical separation of the components in the mobile phase. The separated components are collected or detected at the other end of the column, the eluent end, in the order in which they travel in the mobile phase. In one type of adsorptive process, referred to as capture and release process, the process involves multiple steps, first to load the media, then to wash it, and then to elute it.

Chromatographic methods include among other methods, gel chromatography, ion exchange chromatography, hydrophobic interaction chromatography, reverse phase chromatography, affinity chromatography, immuno-adsorption chromatography, lectin affinity chromatography, ion affinity chromatography and other such well-known chromatographic methods.

Adsorptive media comes in many forms, most typically in the form of beads. The beads are conventionally packed into columns, with the column walls and ends immobilizing the beads into a fixed adsorptive bed, a bed being a porous three dimensional structure containing the stationary phase (in this case the beads) and the pore space through which the mobile phase flows/permeates (the space between the beads). Adsorptive media may also be formed into cohesive beds that retain their shape by virtue of the cohesion in the media; just like beds made with beads, these beds have two distinct regions, one occupied by the stationary phase and another occupied by the mobile phase; this type of media are referred to as monolithic media, or simply as monoliths. Media may also be formed in the shape of fabrics or webs, which can be stacked to form an adsorptive bed. Beds made of monoliths are cohesive in 3 dimensions, whereas beds made of webs are cohesive only in 2 dimensions; beds made of beads alone have no cohesion, requiring the column to maintain its shape.

Planar adsorptive processes and devices have been in use. Examples of planar adsorptive processes are paper chromatography and thin layer chromatography. In these processes, the adsorptive bed has a planar geometry in contrast to the cylindrical geometry of conventional chromatography beds. The mobile phase typically flows through the stationary phase by virtue of the capillarity of the porous medium, which draws the solvent into the porous space of the media. These processes do not require that the fluid pressure be contained since the fluid is not being pumped. More recently, a form of planar chromatography has been developed in which the fluid is pumped; this process is referred to as over-pressure planar chromatography (OPPC). OPPC requires that the media be contained in apparatus that maintains the shape of the bed in spite of the pressures used. In all cases, the planar adsorptive beds used in these processes are very thin, usually no thicker than a millimeter, making them suitable for analytical applications.

Membrane-based adsorptive devices have been developed. In these devices the adsorptive media is either supported by or embedded into a flat micro-porous membrane, which is then fabricated into filtration devices. Two or more of these membranes may be stacked to form an adsorptive bed with a longer flow path; however, the number of layers that can be stacked is limited by the low hydraulic permeability of microfiltration membranes. Such filtration devices are characterized by the fact that the fluid being treated flows through the adsorptive media in a direction substantially perpendicular to the planar dimension of the media. The virtue of membrane adsorbers is their fast kinetics, enabling them to have short bed depths and high feed rates. However, the same attributes that confer them with fast kinetics severely and limit their capacity. Additionally, the intrinsic geometry of existing membrane adsorbers limit their scalability, the largest ones typically being no larger than 5 liters.

Furthermore, the bed depth, or absorptive path length, important in purification steps requiring resolution, is limited in membrane-based devices due to the low hydraulic permeability of microporous membranes. Membrane absorptive media is expensive, because the high cost of the membrane substrate and the challenges of functionalizing the membrane surface with absorptive chemistry. Finally, membrane-based adsorptive devices inherently have low capacity, and as a result membrane adsorption devices have found applicability primarily in "polishing" steps—e.g. virus and DNA removal—where the adsorptive load is negligible, rather than in the core capture/purification steps.

Conventional chromatographic devices require that beads must be packed into a column. The quality of this packing determines the performance of the adsorbing bed. This adds another source of variability to the chromatographic process and must be validated before use. Furthermore, beds packed with beads are prone to voiding, a phenomenon whereby the beads settle into a denser structure resulting in the creation of voids and in non-homogeneities in the packing density of the bed, all of which results in a deterioration of performance. This is especially true in columns packed with soft beads.

SUMMARY

The special demands imposed on pharmaceutical manufacturing processes make it highly desirable that such processes be easily scaled-up. In particular, there are many advantages to processes that can be scaled-up without having to reset or redevelop the processing conditions. Such processes are referred to in the industry as linearly-scalable processes; in essence, the parameters that define the separation process and operating conditions remain unchanged as the process moves from the laboratory bench (i.e., discovery), where the column can be as small as several milliliters, to the process development laboratory (e.g., columns of several liters), to clinical manufacturing, to large-scale manufacturing, where the chromatography column can be as large as several hundred liters. Existing chromatographic devices are not linearly scalable, their design and geometry requiring significant alterations as the device size increases, thereby introducing uncertainties and unwanted risks as processes evolve from drug discovery, to clinical trials, to small-scale and then to large-scale manufacturing.

An adsorptive bed to receive a liquid flow, according to one embodiment, includes a housing having a first surface, a scaffold disposed within the housing in contact with the first surface. The scaffold includes a stress absorbing substantially rigid structure and a plurality of open cells disposed within the rigid structure. The adsorptive bed further includes a plurality of adsorptive beads filling the plurality of open cells forming a packed bed of the plurality of adsorptive beads and the scaffold restricts movement of the plurality of adsorptive beads, absorbs compressive stress induced by a hydraulic pressure gradient along a direction of the liquid flow and transfers a portion of the induced compressive stress to the first surface of the housing. Such a device enables the use of adsorptive bead-based media in planarly cohesive adsorptive beds. Such a device can be linearly scaled to operate from the process development laboratory scale, to clinical manufacturing, to large-scale manufacturing.

Aspects of the present invention relate to absorptive devices that have the high capacity of beads but the operational advantages of webs, and in particular webs that have the properties of native agarose in rigid form. Other aspects of the present invention relate to linearly scalable devices and absorptive devices that provide the flexibility to develop new purification processes beyond the conventional batch chromatography processes.

A chromatographic method to process a liquid includes providing an adsorptive bed comprising as described above, processing the liquid using a rapid cycling controller and operating at a pressure of greater than 100 psi. A chromatography system includes devices using the adsorptive bed described above and additionally include at least one pump and at least one valve controlling a liquid feed stream and a rapid cycling controller coupled to the at least one pump and at least one valve. Such a technique and corresponding system allows operation of adsorptive bed packed in a chromatography column or an adsorptive bed is sealed in a monolithic block to operate at higher flow rates and pressures than can be achieved with conventional devices.

BRIEF DESCRIPTION OF DRAWINGS

The foregoing and other aspects, embodiments, objects, features and advantages of the present teachings can be more fully understood from the following description in conjunction with the accompanying drawings. In the drawings, like reference characters generally refer to like features and structural elements throughout the various figures. The drawings are not necessarily to scale, emphasis instead being placed upon illustrating the principles of the present teachings. The following drawings are illustrative of embodiments of the invention and are not meant to limit the scope of the invention as encompassed by the claims.

FIG. 1A is a schematic diagram of a perspective top view of an adsorptive device according to an aspect of the invention;

FIG. 1B is a schematic diagram of a bottom view of the adsorptive device of FIG. 1;

FIGS. 2A and 2B are schematic diagrams of cross sectional views (along section 2A-2A) of the device of FIG. 1A;

FIG. 3A is a schematic diagram of a side view of an adsorptive device for processing a fluid according to an aspect of the invention;

FIGS. 3B and 3C are schematic diagrams of cross sectional views (along section 3B-3B and along section 3C-3C) of the device of FIG. 2A showing details of the end plates and manifolds;

FIGS. 7A, 7B, 8, 9,10A, 10B, 10C, 11A and 11B, are schematic diagrams showing alternative geometries, media types and flow profiles of cassettes according to other aspects of the invention;

FIGS. 12A, 12B, 12C, 12D, 12E, 13A and 13B are schematic diagrams showing alternative fabrication methods of devices according to the invention;

FIGS. 14A, 14B and 14C are schematic diagrams showing a cassette assembly according to an aspect of the invention;

FIG. 17A is a schematic diagram showing a planarly cohesive separator sheet based on a bi-planar plastic netting suitable for supporting adsorptive beads according to aspects of the invention;

FIG. 17B is a cross section view of the planarly cohesive separator sheet taken along section 17B-17B of FIG. 17A;

FIG. 18A is a schematic diagram showing a planarly cohesive separator sheet based on a woven screen with a square weave according to aspects of the invention;

FIG. 18B is a cross section view of the planarly cohesive separator sheet taken along section 18B-18B of FIG. 18A;

FIGS. 28A-28B are schematic side views of the Chromassette-S adsorptive device of FIG. 27;

FIGS. 29A-29B show magnified views of first end and second end of Chromassette-S adsorptive device of FIG. 27;

FIGS. 30A-30B are top and bottom plan views of first and second planar distributors of the Chromassette-S adsorptive device of FIG. 27;

FIG. 33A is a schematic diagram of a Type-II planar distributor.

FIG. 33B is a schematic diagram of a Type-II planar distributor similar to the Type-II planar distributor of FIG. 33A but having fewer first and second distribution passageways;

FIGS. 35A-35C are schematic diagrams showing a device with improved adhesion and sealing performance of the peripheral seals according to embodiments disclosed herein;

DETAILED DESCRIPTION OF THE INVENTION

Figure 4:
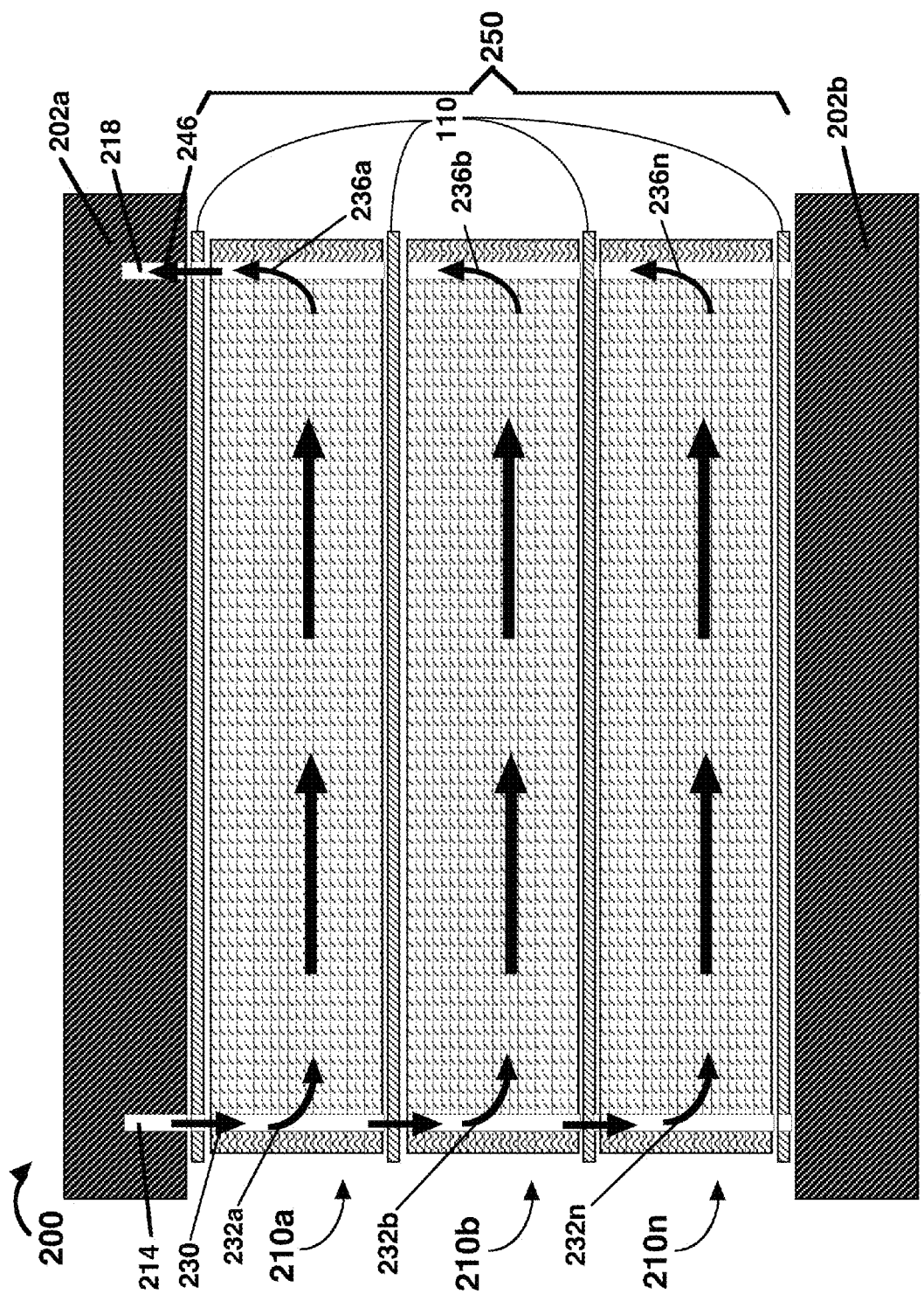
FIG. 4 is an elevation view of a stack of cassettes hydraulically in parallel forming a composite cassette.

This invention generally relates to devices and processes suitable for preparative and manufacturing processes, and more specifically to processes used in the manufacture in the pharmaceutical industry for the production of medicinal or therapeutic products.

In contrast to conventional devices, applicants have discovered a way to support adsorptive media in a configuration that is linearly scalable and self supporting. Embodiments of the invention utilize planarly cohesive media. A web of adsorptive media, as for example, Macro-IPN media, is planarly cohesive. The media retains its shape even when pulled apart by a tensile force. A monolith is also planarly cohesive, except that it is much thicker than a bed. The cohesion plane of planarly cohesive media is oriented in parallel to the planar surfaces of the adsorptive device. The cohesiveness of the media along the cohesion plane enables the fabrication of adsorptive media blocks as described below.

The term adsorptive media, chromatography media, and media are herein used interchangeably to refer to the stationary phase of an adsorptive device; media can also refer a single type of medium. As used herein, intimate contact generally refers to the scale of the void space left between adjacent layers, and means that these void spaces are of the same order of magnitude as the scale of the interstitial space occupied by the mobile phase within the beds. The term solvent and mobile phase are used herein interchangeably to refer to the stationary phase. The term lateral flow means fluid flow within the media along the cohesion plane; for example, in web-based adsorptive media lateral flow means flow along the plane of the web, in contrast to flow that is perpendicular to the plane of the web. The term adsorptive block and adsorptive device and cassette are used interchangeably to refer to the planarly cohesive beds of adsorptive media used in devices disclosed herein. The term isotropic means that the porous media through which the fluid flows has a homogenous porous structure perpendicular to the direction of flow, such that the specific resistance to flow is independent of the location of the in the media in planes perpendicular to the direction of flow; the importance of isotropic media is elaborated upon further below. By substantially it is meant that the deviations of the values of the property being described are sufficiently small to enable the adsorptive device to perform as expected.

Referring to FIGS. 1A-1B, an adsorptive device 10 includes at least one block 20 comprising planarly cohesive, substantially isotropic adsorptive media 21, the block has a first end 12, a second end 16, a first substantially planar surface 22, a second substantially planar surface 23, at least one sidewall 26 substantially perpendicular to the first and second planar surfaces 22, 23. The block further comprises a first plurality of distribution passageways 14a-14n (collectively referred to as distribution passageway 14) disposed within the at least one block 20, adjacent the first end 12 and substantially perpendicular to the first and second planar surfaces 22 and 23, a second plurality of distribution passageways 18a-18n (collectively referred to as distribution passageway 18) disposed within the at least one block 20 adjacent the second end and substantially perpendicular to the first and second planar surfaces 22 and 23, and a peripheral edge seal 28 encapsulating the at least one sidewall 26 having a planar surface portion 24.

The alignment and location of the distribution passageways 14 and 18 with respect to each other and the geometrical shape of the first and second planar surfaces 22 and 23 (also referred to as the footprint) are designed to induce substantially uniform lateral flow of fluid within the block 20 from the first end 12 to the second end 16. The block 20 may have a variety of footprints, for example, rectangular, circular, trapezoidal, etc. The shape of the footprint in conjunction with the location of the distribution passageways 14 and 18 are the design factors responsible for inducing the desired uniform flow.

The block 20 is a three-dimensional device characterized by a length 32, a height 30 and a width 34. The direction of fluid flow is aligned with the length coordinate; the width of the planar surfaces 22 and 23 defines the width 34 and the height 30 of the block 20 is the dimension perpendicular to the planar surfaces 22 and 23.

In operation, fluid is introduced and distributed into distribution passageways 14 and collected and removed from distribution passageways 18. The adsorptive device 10 is rendered "self-supporting" by the encapsulation of the sidewall 26 defined by the cohesion planes, parallel to the planar surfaces 23 and 23, of the planarly cohesive, substantially isotropic adsorptive media 21. The blocks 20 of adsorptive device 10 do not require additional support structures to contain the hydraulic pressures generated in use, enabling the blocks 20 to be easily loaded and unloaded between end plates shown below in conjunction with FIG. 2A. This attribute additionally allows the stacking of blocks 20 without a change of the end plates enabling very easy scale-up.

It is understood that in an adsorptive device 10 there are numerous possible paths, or streamlines, between the distribution passageways 14 and 18. The fluid in each streamline takes a certain amount of time to complete the trajectory from the first end 12 to the second end 16, this time being typically referred to as the residence time. High performance adsorptive devices require that the variation in the residence time of all the streamlines be as small as possible. To achieve this performance attribute, adsorptive blocks should have adsorptive media that is substantially isotropic along planes perpendicular to the direction of flow, in addition to having streamlines that have substantially uniform length. Flow uniformity is the net result of this combination of properties.

In one embodiment the layers of adsorptive media are formed from web-based adsorption media, for example, macroporous IPN media produced in a web and cut to fit the block 20. Macroporous IPN media is described in PCT application PCT/US2010/024804 entitled POROUS INTERPENETRATING POLYMER NETWORKS WITH IMPROVED PROPERTIES, filed Feb. 19, 2010, which is incorporated by reference in its entirety. In other embodiments the layers of adsorptive media might comprise Empore discs (3M Corp., St. Paul, Minn.), or Whatman Chromatography Paper (GE Life Sciences, Westborough Mass.).

FIG. 2A shows a magnified section view (through Section 2A—Section 2A of FIG. 1A) of distribution passageways 14 on the first end of block 20. FIG. 2A shows a cross section of block 20 having four layers of web 29. FIG. 2B shows a block 20' having more layers of web 29 and therefore a higher height than the block 20 shown in FIG. 1A. Block 20 can include multiple web layers 29a-29n (collectively referred to as web layer 29) of the planarly cohesive, substantially isotropic adsorptive media 21.

The feed stream (not shown) is distributed along the width of the block 20 by manifold 120 (shown below in conjunction with FIG. 3B) entering each one of several passageways 14a-14n as a feed sub-stream, which is further distributed and turned forming lateral flow streams within each web layer 29. In contrast to filtration devices, lateral streams 8 flow along the plane that defines web layer 29 (i.e., these flow laterally rather than perpendicularly to the plane of web layer 29).

FIG. 2B shows adsorptive device 10' which includes additional web layers 29 as compared to adsorptive device 10 of FIG. 2A.

Now referring to FIGS. 3A-3C, an adsorptive device 100 for processing a fluid includes a pair of end plates 102a and 102b (also referred to as end plate 102). Each end plate 102 has a feed end 105 and an eluent end 107. At least one of the pair of end plates 102 has a feed inlet 106 disposed at the feed end 105, and at least one of the pair of end plates 102 has an eluent outlet 108 disposed at the eluent end 107. The adsorptive device 100 further includes a plurality of cassettes 200 in a stacked configuration (shown here as a single cassette 200, stacked configurations described below in conjunction with FIGS. 3, 4 and 5).

Each cassette 200 is similar to the block 20 of FIG. 1A. As described above, the cassette 200 geometry and location of the passageways induce substantially uniform lateral flow from the feed end 105 to the eluent end 107 within the block, the uniform lateral flow being parallel to the first and second substantially planar surface. Here, one of the pair of end plates 102a is adjacent to the first surface 22 of the cassette 200 and a second one of the pair of end plates 102b is adjacent to a second surface 23 of the cassette 200.

Still referring to FIGS. 3A-3C, cassette 200 further comprises peripheral edge seal 28 forming an impermeable seal of web 29 (also called "seal" and "peripheral edge seal") using a sealant. In one embodiment a thermoset resin is used and in another embodiment a thermoplastic resin is used to form the seal. Other sealants known in the art can also be used. Peripheral edge seal 28 is adhered to web 29 forming a structural boundary to include the elevated pressures present inside the cassette. Cassette 200 further comprises passageways 14 and 18 distributed along its width at both the feed and eluent ends, respectively, and are used for the introduction of the feed stream and collection of the eluent stream along the width of cassette 200. Passageways 14 (also referred to as distribution passageways) penetrate cassette 200 along its height from top to bottom, enabling the distribution of fluid along the height H.

FIG. 3B shows a sectional side view of a manifold 120a disposed in end plate 102a. Manifold 120a is used to introduce the feed stream 130a, whereas manifold 120b disposed on the opposite end of end plate 102a is used to recover the eluent stream 130b, as shown in FIG. 3C. Flow passages 124a inside manifold 120a are used to distribute the feed stream to distribution passageways 14 in cassette 200. Flow passages 124b inside manifold 120b are used to collect the eluent stream from distribution passageways 18 in cassette 200. It is understood that there are several different operational configurations of the manifold 120a and 120b in the end plates 102a and 102b.

In certain embodiments, cassettes 210a-210n are stacked such that they are hydraulically in parallel as shown in FIG. 4 (hereafter referred to as a "parallel configuration"). In this case cassettes 210 form a composite cassette 250 whose height is equal to the sum of the heights of each cassette 210. Manifolds 120a and 120b (FIG. 3A) are used to support stacked cassettes 210 by means of support structure (not shown), which can be made of tie rods or of some sort of external press), and include passageways (not shown) to distribute the feed stream into the distribution passageways on the feed end and to collect the eluent stream from the eluent end of cassettes 210. Manifolds 120 are have a feed and an eluent end to match the feed and eluent ends of cassettes 210.

Feed and eluent distribution passageways 14 and 18 can be configured in several positions in the end plates. Both can be located only in the top manifold, or only in the bottom manifold. Alternatively, feed distribution passageways can be located only on the top end plate with eluent distribution passageways only on the bottom end plate or any combinations thereof, as long as there is at least one set of feed distribution passageways and one set eluent distribution passageways in either the top or bottom manifolds disposed within the end plates. Gaskets 110 may be used to obtain a reliable seal between adjacent cassettes 210 and between cassettes 210 and manifolds. Gaskets 110 may be integrated (and adhered) into each cassette 210, or may be a separate component that is added as part of a stack of cassettes 210 to form a block. To enable cassettes 210 to be stacked in the fashion shown in FIG. 4, these must be approximately of the same length and width, and the distribution passageways need to be similarly located so that they line up and are in fluid communication; however, it should be understood that while FIG. 4 shows cassettes 210 of the same height, cassettes can be of different heights.

Figure 5:
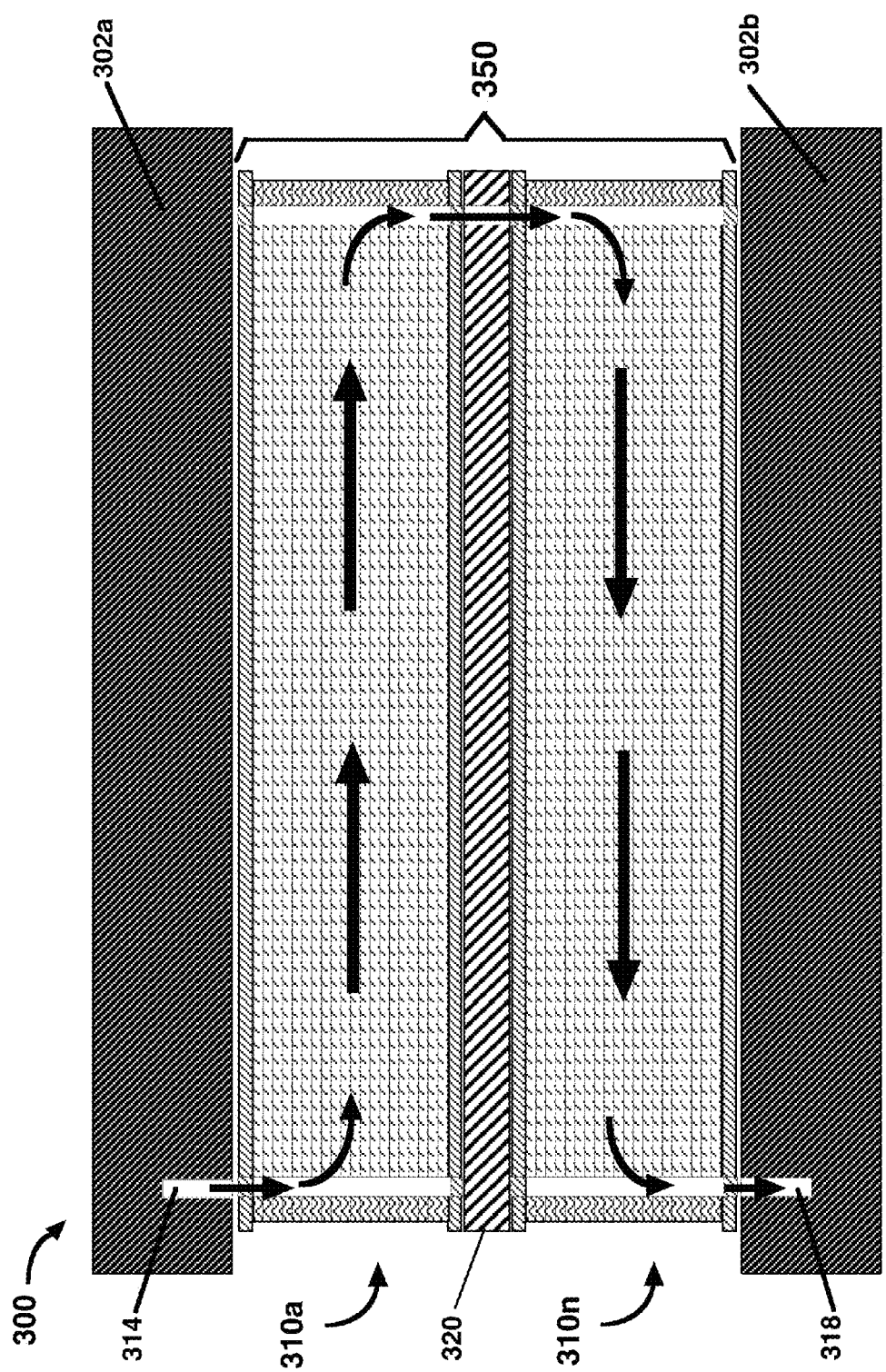
FIG. 5 is an elevation view of a stack of cassettes hydraulically in series forming a composite cassette.

Alternatively in other embodiments, cassettes are stacked such that they are hydraulically in series as shown in FIG. 5. In this case cassettes 310a-310n form a composite cassette 350 whose hydraulic length is equal to the sum of the lengths of each cassette 310 by virtue of flow diverter plate 320. Manifolds (not shown) are used to support stacked cassettes 310 by means of support structure (not shown), and include distribution to distribute the feed stream into the distribution passageways 314 on the feed end and to collect the eluent stream from the eluent end of cassettes 310. End plates have a feed and an eluent end to match the feed and eluent ends of cassettes 310. In contrast to the parallel configuration shown in FIG. 4, feed and eluent passageways must be located in separate manifolds. Gaskets 110 may be used to obtain a reliable seal between adjacent cassettes 310, between cassettes 310 and flow diverter plates 320, and between cassettes 310 and end plates. Gaskets 110 may be integrated (and adhered) into each cassette 310, or may be a separate component that is added as part of a stack of cassettes 310 to form a block. To enable cassettes 310 to be stacked in the fashion shown in FIG. 5, these must be approximately of the same length and width, and the distribution passageways need to be similarly located so that they line up and are in fluid communication. However, it should be understood that while FIG. 5 shows cassettes 310 of the same height, cassettes can be of different heights; furthermore, two or more cassettes can be placed in series.

It is understood that it is possible to create composite cassettes utilizing combinations of parallel and series configurations as shown in FIGS. 4 and 5 by introducing flow diverter plates 320 at desired locations within a stack of cassettes 310.

Figure 6:
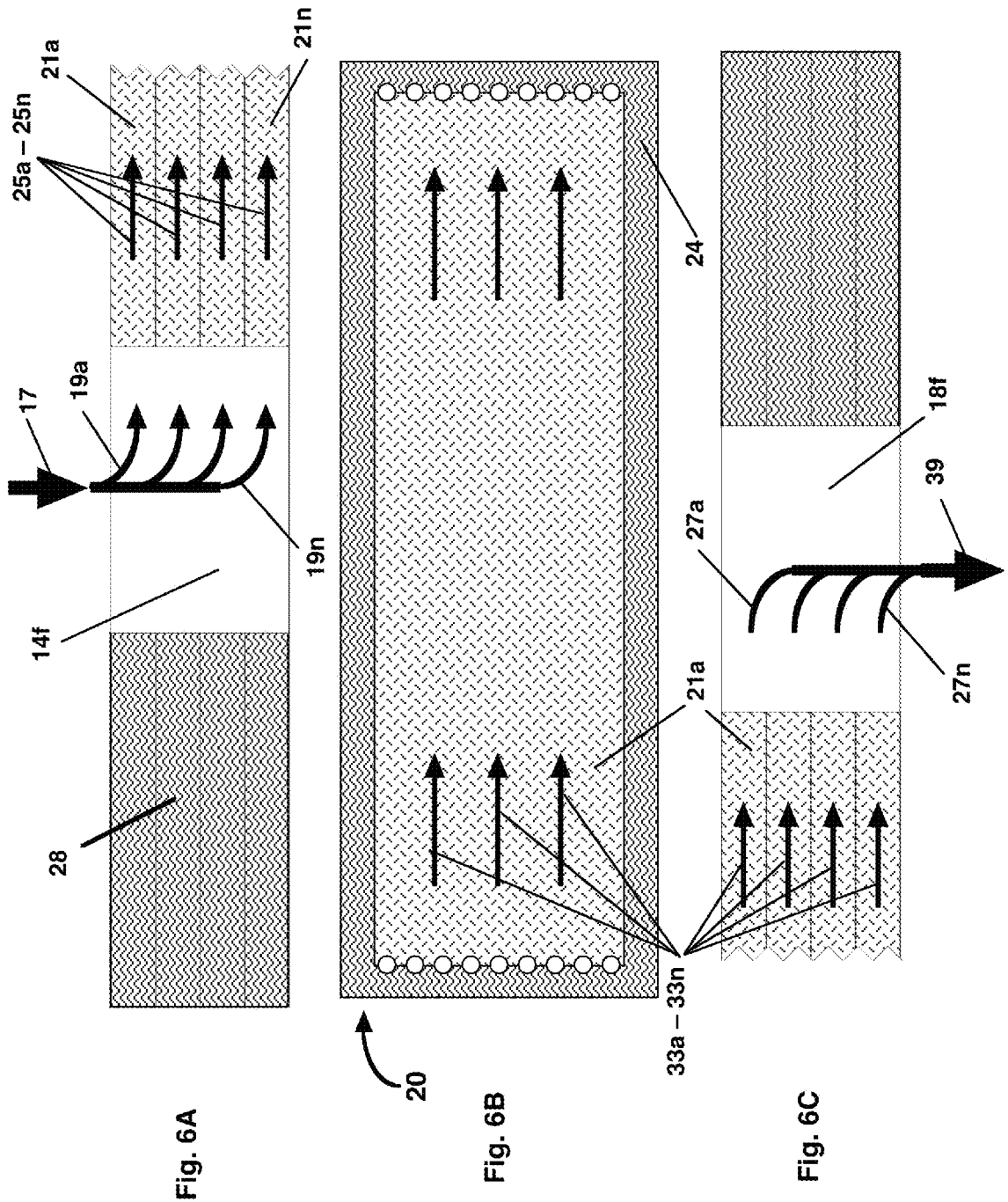
FIGS. 6A-6C are schematic diagrams showing flow profiles in cassettes according to an aspect of the invention.

FIG. 6A shows a magnified section view (through Section 2A on FIG. 1B) of distribution passageway 14f on the feed end of block 20, showing the flow profile of the feed stream within each web 21a-21n. The feed stream (not shown) is distributed along the width of the block by the manifold (not shown) entering each one of several distribution passageways 14 as feed sub-stream 17, which is further distributed and turned forming lateral streams 25a-25n within each web layer. In contrast to filtration devices, lateral streams 25a-25n flow along the plane that defines web 21 (i.e., these flow laterally rather than perpendicularly to the plane of web 21). FIG. 6B shows the flow streamlines 21a-21n in a plan view on web 21, showing the fluid traveling from the feed end towards the eluent end. FIG. 6C shows a magnified section view (through Section 2A on FIG. 1B) of distribution passageway 18f on the eluent end of block 20, further showing how lateral streams 33a-33n within each web layer 21 are collected to form eluent sub-stream 39 within distribution passageway 18f. There are multiple eluent sub-streams 39 that are collected along the width of the cassette by the manifold (not shown) forming the complete eluent stream (not shown) from block 20.

Figure 7:
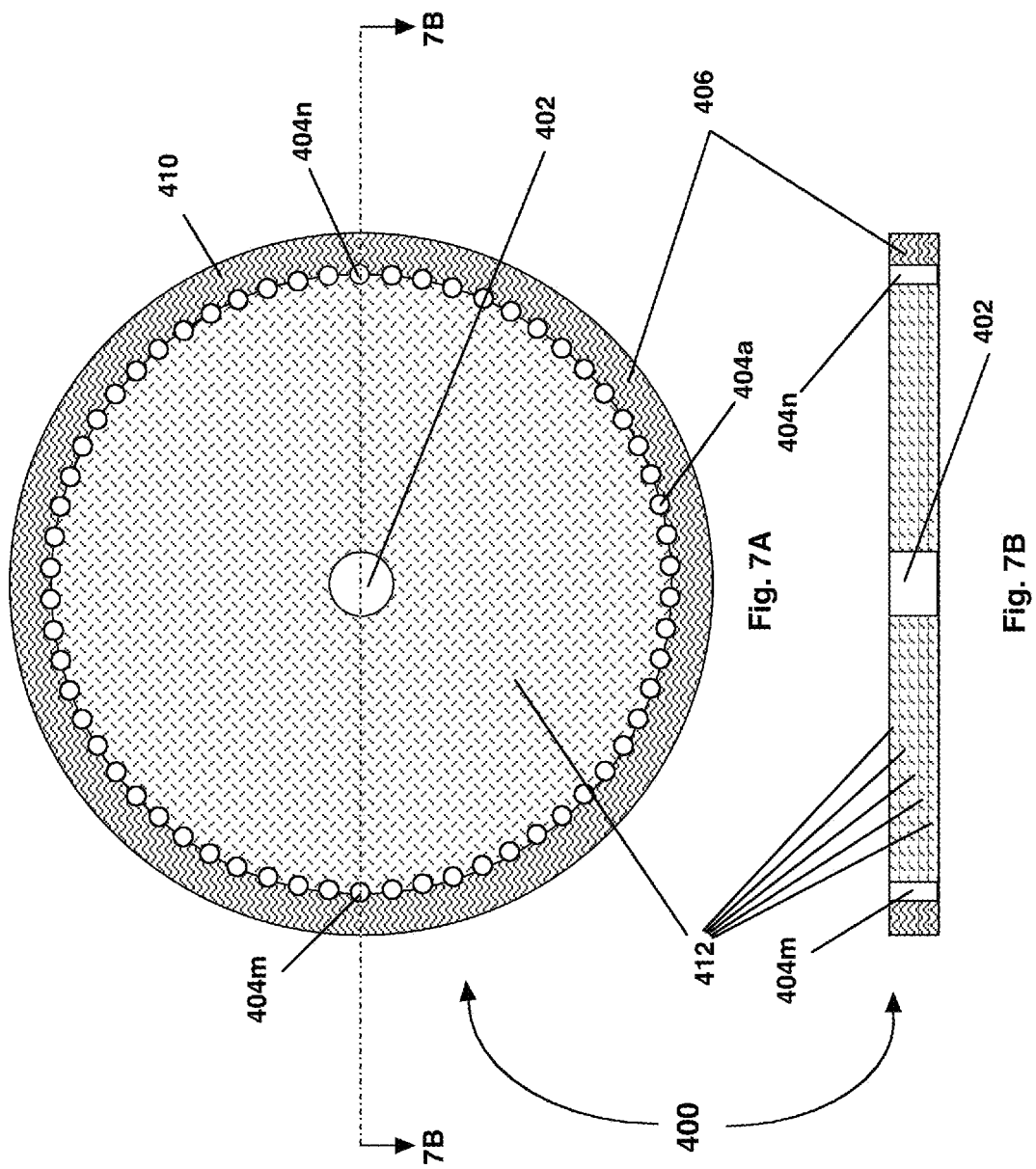

FIG. 7 shows another embodiment, where the cassette is configured in a circular geometry instead of a rectangular geometry as shown in FIG. 1A. Circularly shaped web 412 has a peripheral edge seal 410 with distribution passageways 404a-404n. In this case the feed distribution passageways 404 are located in the periphery of web 412, whereas the eluent distribution passageway 402 may be a single channel in the center of web 412 (it should be understood that the distribution passageway 402 in the center of the circular web may also comprise two or more distribution passageways 402). Alternatively, the passageway 402 in the center is the feed distributor whereas the passageways 404 near the periphery are the eluent distributors. In this case the fluid flow path is radial, making the length of the flow path approximately equal to the radius of the circularly shaped web 412.

Figure 8:
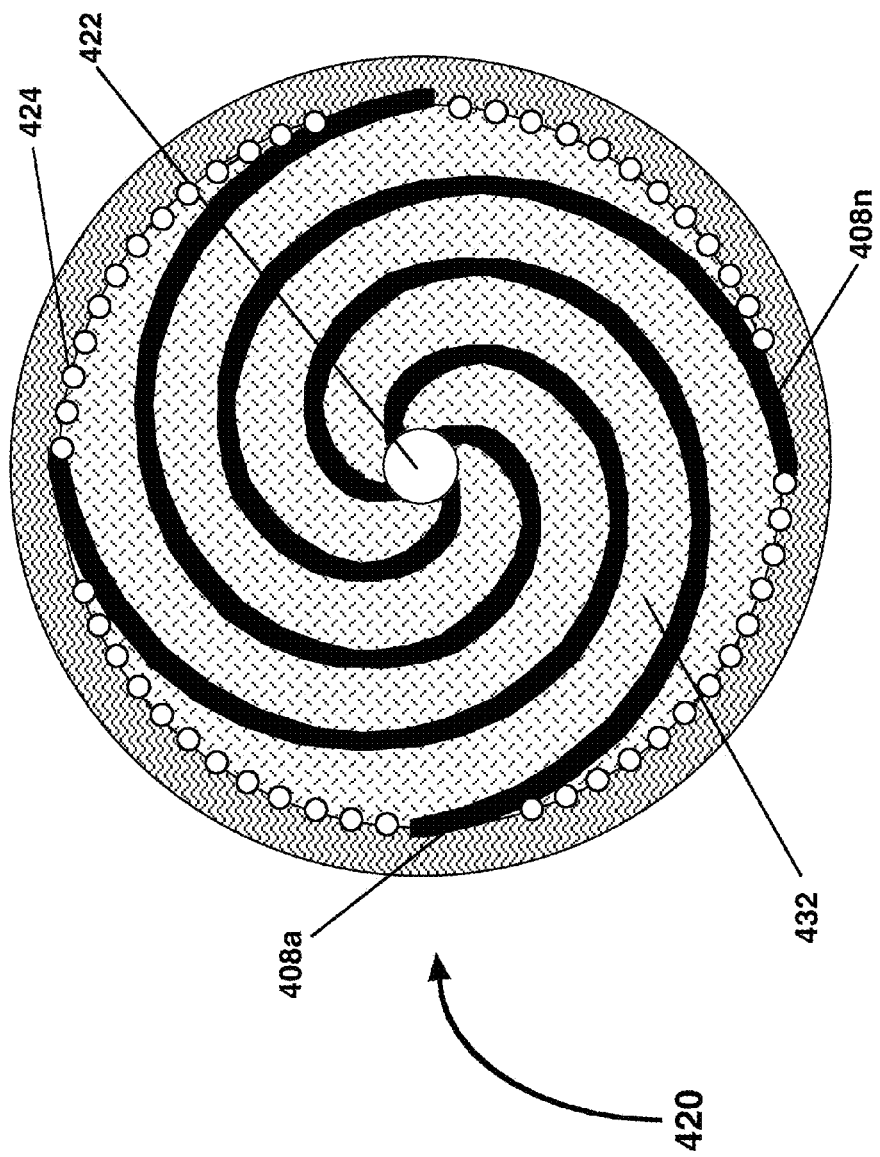

FIG. 8 shows another embodiment of a circularly shaped cassette including ribs 408a-408n that force the fluid to flow in a spiral trajectory forming a longer flow path than that on the embodiment shown in FIG. 7.

Figure 9:
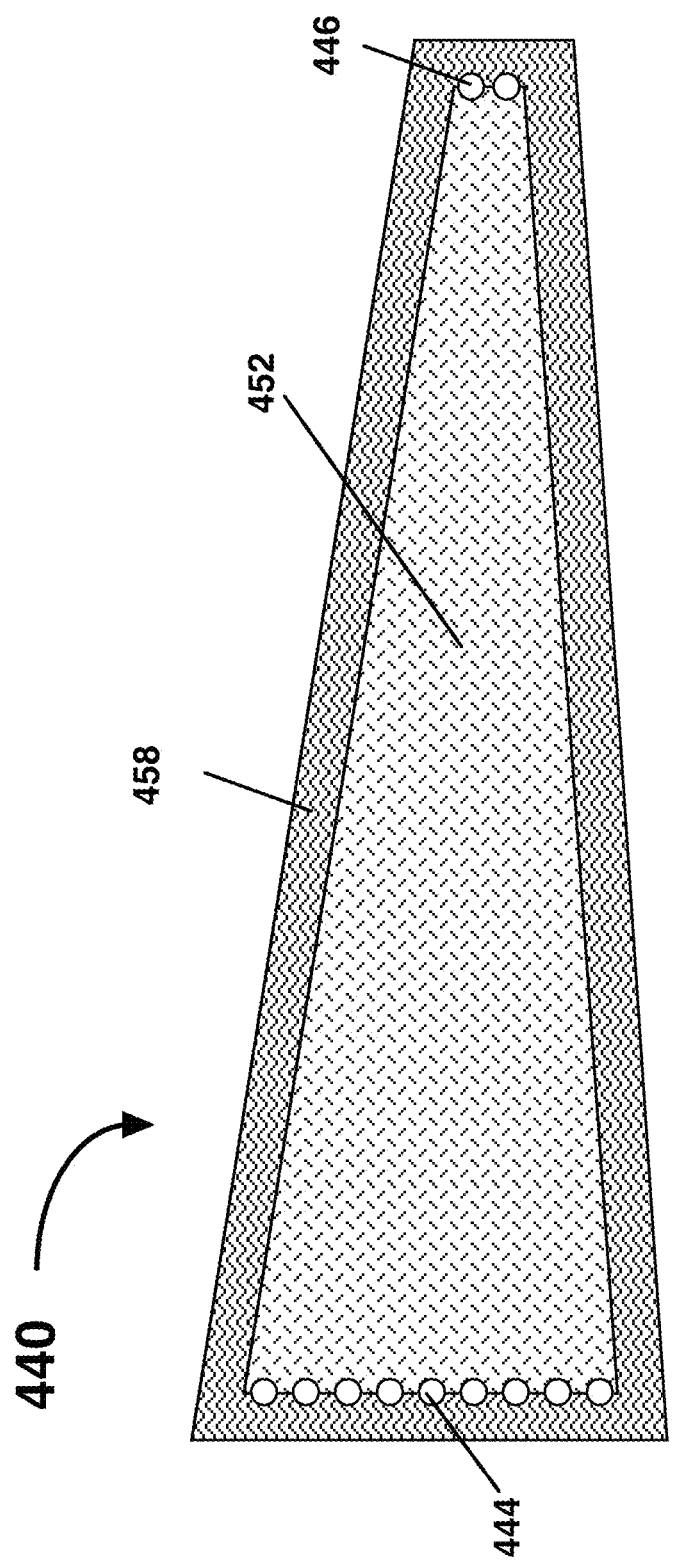

FIG. 9 shows another embodiment of a cassette 440 whose webs 452 are approximately in the shape of a "pie slice" or a trapezoid. Any shape is possible as long as webs 452 are flat, have peripheral edge seal 448 and distribution passageways 444 and 446, the application dictating which shape is most beneficial. Also, in general it should be understood that ribs (not shown) can be utilized in any geometry, circular, rectangular or otherwise, to channel the fluid in trajectories which may be different from the natural trajectory that a fluid would travel within the webs 452.

FIG. 10 shows a cassette 500 according to one embodiment devices disclosed herein made with an adsorptive media in the form of a monolith 522 instead of multiple web layers, the key difference being that monolith 522 is much thicker than a web, such that a single monolith creates a substantial height (only possible with multiple layers when using webs). According to this embodiment monolith 522 comprises peripheral edge seal 506 and distribution passageways 508, FIG. 10B showing a cassette made with a monolith thinner than that shown in FIG. 10C. Just as has been described in FIGS. 1 through 7, cassettes of the same geometries and possibilities can be made with monoliths 522 as long as these have planar top and bottom surfaces and have sufficient tensile and compressive strength to support the hydraulic forces generated in use. Monoliths create the option of adding a seal to the planar top and bottom surfaces capable of restraining the hydraulic forces generated in use. In this case the top and bottom plates become optional since the cassette is self-supporting; furthermore, the end plates only need to attach to the feed and eluent distributors in cassette 500.

FIG. 11A shows a plan view of another embodiment of a rectangular-shaped cassette in which the cassette is "double-sided". In this embodiment the cassette includes another set of distribution passageways 516 at the center point of the length dimension of web 512 in addition to the set of distribution passageways 504 and 508 at the two ends of the cassette 500. Referring to FIG. 11A cassette 550 comprises webs 512 with peripheral edge seal 513 having a set of center distribution passageways 516 at the center point of the length dimension of web 512, and two sets of distribution passageways 504 and 508 at the two ends of web 512. In this particular embodiment center passageways 516 distribute the feed stream, while end passageways 504 and 508 collect the eluent stream. Flow profiles for this embodiment are shown in FIG. 11B. In an alternative embodiment of a double-sided cassette (not shown), distribution passageways 504 and 508 distribute the feed streams while center passageways 506 collect the eluent streams.

FIGS. 12A-12E represent in schematic manner an exemplary process to fabricate the cassette shown in FIG. 1A. A plurality of webs 600 are cut to a desired dimension as shown FIG. 12A and stacked as shown in FIG. 12B. A peripheral edge seal 606 is created by one of many methods known to those skilled in the art (e.g., a thermoset resins or thermoplastic resin or other sealants known to those skilled in the art can also be used) as shown in FIG. 12C. Once cured, the stack of webs 600 is perforated (by drilling, die cutting, laser cutting or other methods known to those skilled in the art) to form substantially straight distribution passageways 604 and 608 in the height dimension as shown in FIG. 12D, resulting in finished cassette 620 of FIG. 12E.

There are many variations to this fabrication method. For example, the distribution passageways may be perforated on each individual web 650 before these are stacked; this method allows the formation of distribution passageways that are not identically located in each web 650, which is acceptable as long as the distribution passageways 654 and 658 have some overlap enabling fluid communication when adjacent webs 650 and 660 are stacked, as shown in FIGS. 13A and 13B. Referring to FIG. 13A, web 650 is perforated with oblong distribution passageways 658, which are not centered in the width dimension but are closer to one edge of web 650 than the other edge, whereas web 660 shown in FIG. 1B is perforated with the same oblong distribution passageways 658 which are also not centered (according to offset 655), but displaced towards the opposite edge of web 660. When adjacent webs 650 and web 660 are stacked, the distribution passageways 654 and 658 do not line up perfectly on top of each other, but do overlap to still create a distributor that is in fluid communication. It should be appreciated that perforating the web 650 with distributor passageways 654 before stacking the webs provides a large flexibility in the formation of the distributors, which may be of advantage in some applications. Likewise it may be advantageous to add peripheral edge seal 662 to each web individually before these are stacked.

Distributors may add to band spreading, a phenomenon that deteriorates the effectiveness of chromatographic separation, a deterioration that increases as the hold-up volume of distributors becomes larger relatively to the volume in the separation medium. Therefore, distributors should be designed to have the lowest volume. However, this needs to be balanced with the pressure drop generated by a distributor, which becomes larger the smaller the diameter of the distribution passageways. In many cases, it is possible to maintain the distributor volume to be small relative to the rest of the adsorptive medium, and in such cases, it does the exact distribution pattern of the feed and eluent streams within the distributor has little impact on the separation performance of the devices. In such cases, it is of little consequence where the fluid enters and exits the cassette.

Another approach to reduce the deterioration produced by distributors is to design them such that the bands are not distorted, even when the distributor volume is not small. This requires that every streamline within the passageway separation device (the separation media and the distributor, including the flow passages/distributors contained within the end plates) have the same residence time. For devices disclosed herein, wherein the feed stream comes from a point source and the eluent stream goes back to a point source, the location of entry and exit of the feed and eluent streams, respectively, may be important, leading to preferred embodiments for the distributor design. In the case of rectangular devices disclosed herein (e.g. as shown in FIG. 1 through 4), to maintain the residence time at every streamline as uniform as possible in the presence of significant hold-up volume in the distributors the design principle that should be followed is this: there should be mirror image symmetry in the flow pattern of the feed and eluent streams as they enter and exit the cassette along any plane bisecting the cassette in any of its dimensions. Specifically, this means two things: first, the feed and eluent streams should be located in opposing end plates, and secondly, the feed stream should enter the top (or bottom) end plate on the side opposite to that in which the eluent stream exits the opposite end plate.

FIGS. 14A, 14B and 14C show a device 700 comprising a cassette assembly according to one aspect disclosed herein with end plates designed according to the design principle described in the previous paragraph. FIG. 14A shows a sectional side view of cassette assembly 700, with top end plate 706a, a first gasket 705a, cassette 702, a second gasket 705b, and bottom end plate 706b. In this schematic diagram, top end plate 706a is used to introduce the feed stream, whereas bottom end plate 706b is used to recover the eluent stream. Flow passages 716a inside top end plate 706a is used to distribute the feed stream to distributor passageways 704a in cassette 702. Flow passages 716b inside bottom end plate 706b are used to collect the eluent stream from distributor passageways 704b in cassette 702. FIG. 14B is a front view of a cassette assembly 700 taken along section 14B in FIG. 14A. Referring to FIG. 14B, feed stream 707 enters end plate 706a at feed port 717, and then is further distributed along the width of the device utilizing flow passages 716a. Referring now to FIG. 14C, eluent stream 709 exits end plate 706b at eluent port 719, after having been collected along the width of the device utilizing flow passages 716b. FIGS. 14A, 14B and 14C clearly show that feed and eluent flow passages in end plates 706a and 706b are in mirror image symmetry one to the other as described in the previous paragraph, representing a preferred embodiment whenever the volume of the distributor passageways 704a and 704b in the devices disclosed herein lead to decreased separation performance. It should be further noticed that in this embodiment the flow direction of the feed and eluent streams is the same at every point within cassette assembly 702.

Figures 15A, 15B:
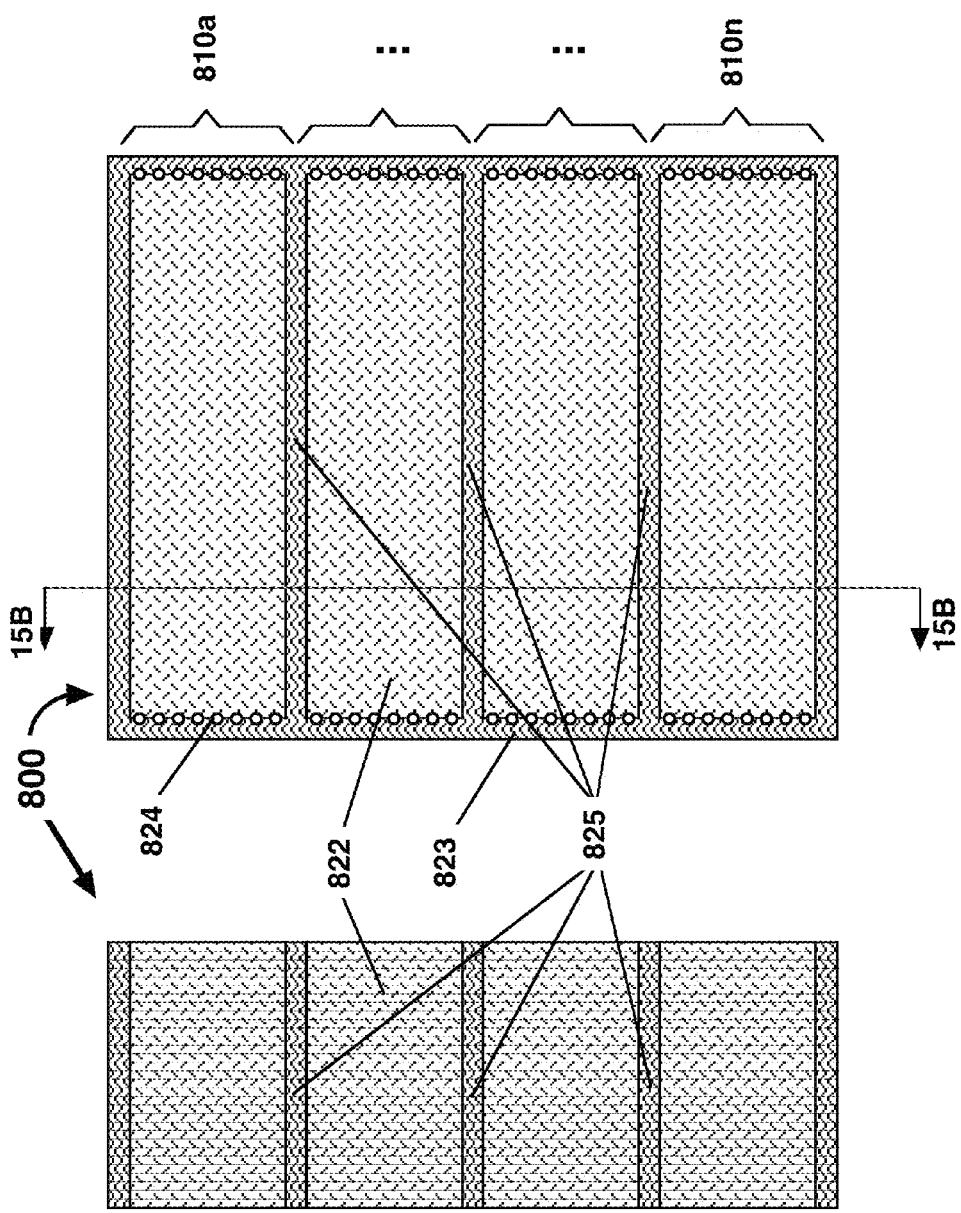
FIGS. 15A, 15B, 16A and 16B are schematic diagrams showing the multiplexed cassettes according to aspects of the invention.

FIGS. 15A and 15B show another embodiment disclosed herein, according to which multiple cassettes 810a-819n are integrated into a single multiplexed cassette 800. Block 822 has peripheral edge seal 823 and further partitioned into multiple cassettes 810a-810n by means of inter-cassette seals 825. Distribution passageways 824 are perforated along the height of block 822 on both ends of block 822 in the manner shown in FIG. 15A. In this embodiment block 822 of multiplexed cassette 800 is built from a stack of multiple layers of web (not shown). Peripheral edge seals 823 and inter-cassette seals 825 are adhered to webs such that these can sustain the internal pressures present in cassettes 810a-810n during use. In another embodiment the media used to form the adsorptive block 822 may be in the form of a monolith (not shown) instead of webs.

Figure 16A:
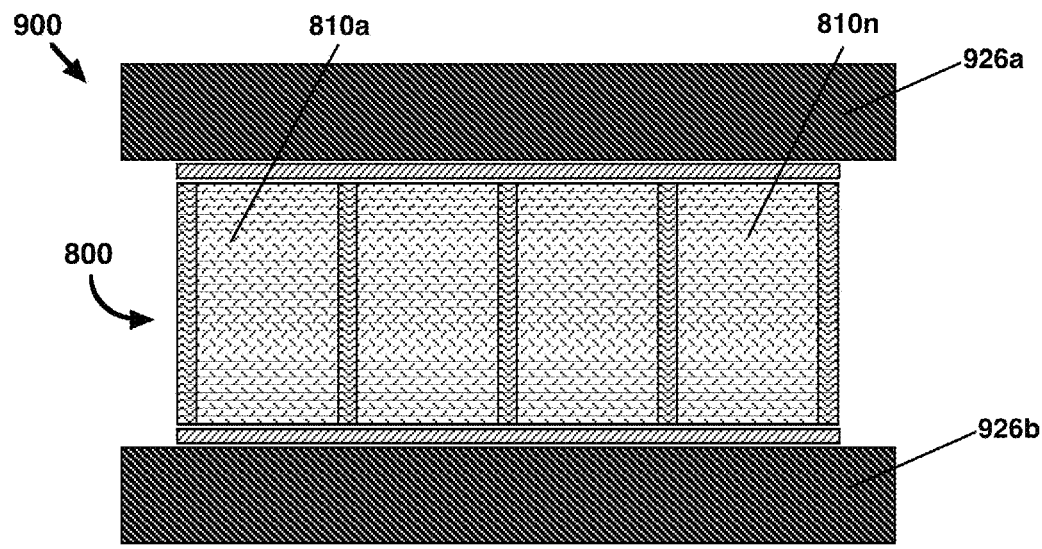
Figure 16B:
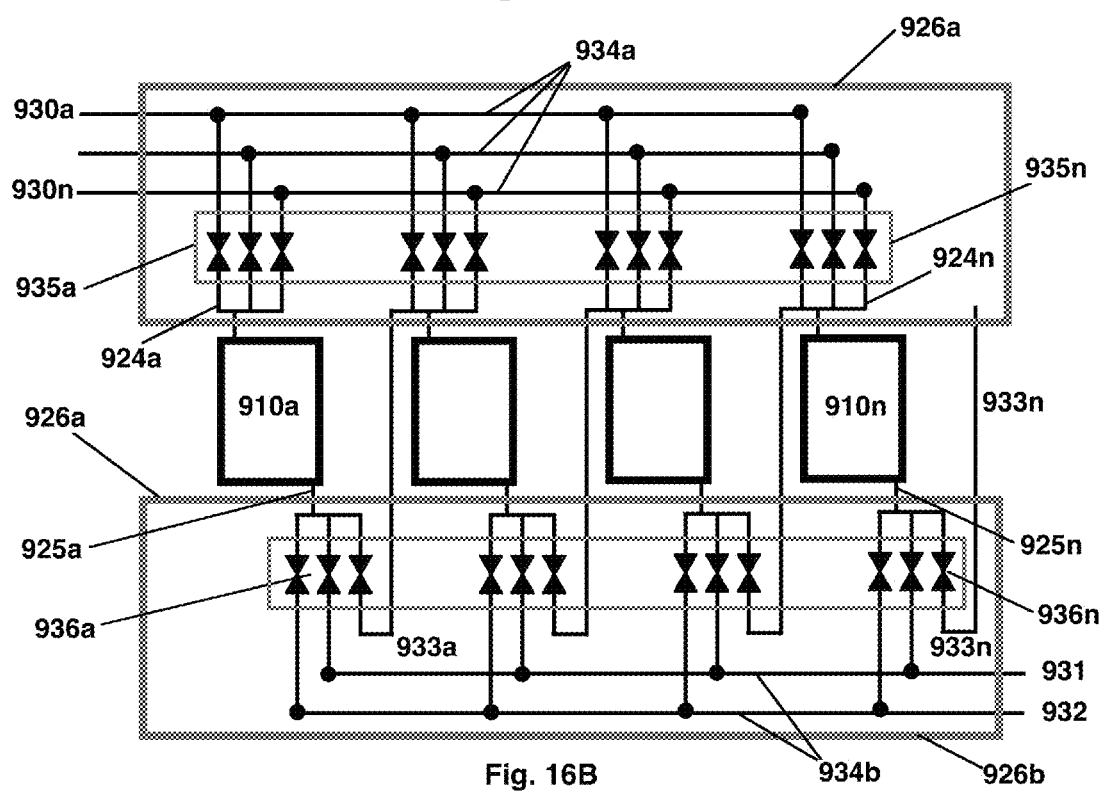

FIG. 16A is an elevation view of a multiplexed cassette 800 in combination with end plates 926a and 926b forming multi-cassette assembly 900. FIG. 16B is a schematic flow diagram of multiplexed cassette assembly 900. End plate 926a includes multiple passageways 934a for introducing multiple feed streams 930a-930n and an array of valves 935a-935n for diverting each feed stream into the manifold 924a of each one of cassettes 810a-810n. End plate 926b includes multiple passageways for collecting multiple eluent streams 934b from each one of cassettes 810a-810n and an array of valves 935b for diverting each eluent stream from the eluent distributors 924b into either a product stream 931, a waste stream 932, or possibly, a feed stream 933a-933n into another one of cassettes 810a-810n. The passageways and valves are included within the end plate, thereby liberating the user from having to make individual connections to each individual cassette 810a-810n. The process design dictates which valves are opened and closed, with a control system (not shown) that opens and close the valves accordingly. In some embodiments the end plates 926a and 926b are reusable. In other embodiments end plates 926a and 926b may be integrated with the cassette to form a completely disposable assembly 900, in which case valves 935a and 935b may be pneumatically actuated, with the pneumatic streams actuated by an array of reusable valves (not shown) connected to the disposable cassette assembly 900 by simple, quick-connect means known to those skilled in the art. This embodiment would be suitable for applications where cross-contamination between batches cannot be tolerated, or where the cost of cleaning and validating the cleaning cycle is cost or time prohibitive, or when the safety of operating personnel demands that there be no exposure to the fluid streams.

In other embodiments adsorptive beds designed to receive a liquid flow as described below in conjunction with FIGS. 17A-23 can be used to form planarly cohesive adsorptive blocks or can be used in chromatography columns. In these embodiments the composite adsorptive bed includes a scaffold with open cells (also referred to as void spaces) and adsorptive beads occupying the void space created by the scaffold. The scaffold provides the planar cohesion required by the planar adsorptive devices, and the adsorptive beads provide the desired adsorptive properties. In embodiments utilizing chromatography columns, the scaffold provides structural support to prevent the beads from being crushed, and the adsorptive beads provide the desired adsorptive properties. FIGS. 17A through 22B show examples of planarly cohesive separator sheets suitable for scaffolds for both planar adsorptive devices and chromatography columns, as described below.

Figure 23A:
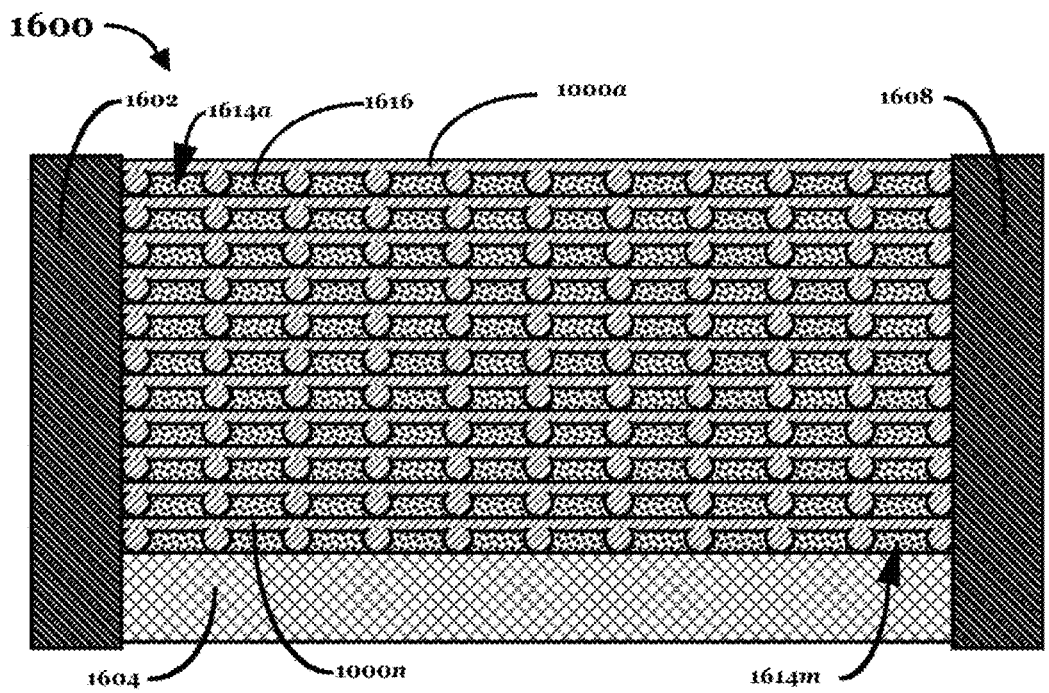
FIG. 23A is a schematic diagram of a scaffold formed by stacking planarly cohesive separator sheet aligned and in intimate contact with adjacent sheets according to aspects of the invention.
Figure 23B:
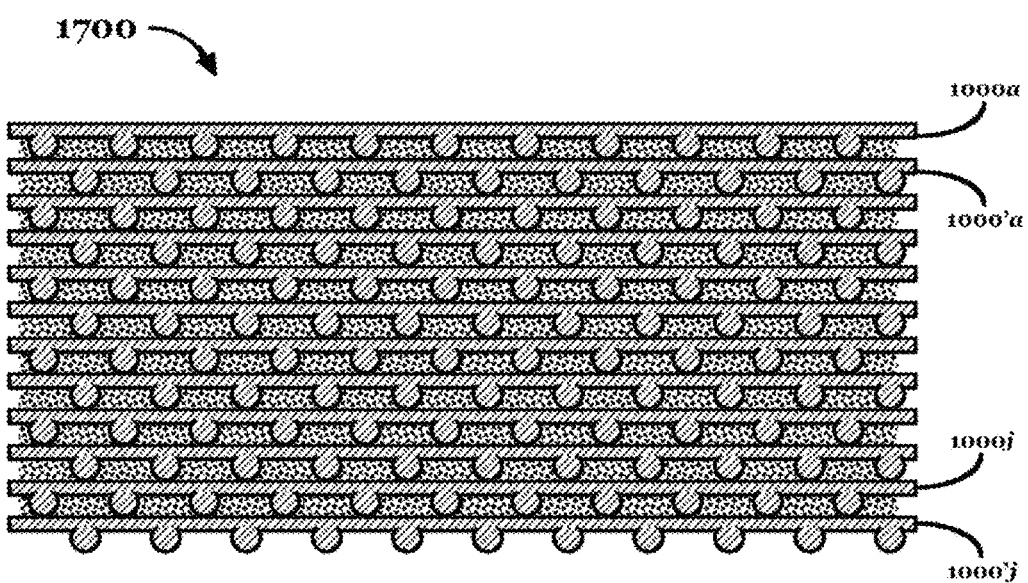
FIG. 23B is a schematic diagram of a scaffold formed by stacking planarly cohesive separator sheet staggered and in intimate contact with adjacent sheets according to aspects of the invention.

Now referring to FIG. 17A, a planarly cohesive separator sheet 1000 includes a plurality of rigid structural members 1010a-1010n (generally referred to as members 1010) and rigid structural members 1012a-1012m (generally referred to as members 1012) arranged to define the plurality of open cells 1014. The planarly cohesive separator sheet 1000, when stacked together form a stress absorbing substantially rigid structure of a scaffold as shown in FIGS. 23A and 23B. The planarly cohesive separator sheet 1000 can also be stacked in a chromatography column as shown in FIG. 26. In one embodiment, the planarly cohesive separator sheet 1000 comprises a bi-planar plastic net 1000. The bi-planar net 1000 is formed from members 1010 arranged to form a first array of straight members parallel to each other and in a single plane, and members 1012 arranged to form a second array of straight members parallel to each other and in a single plane, wherein the first and second array are perpendicular to each other as shown in FIG. 17A. Here, the rigid structural members are polymeric monofilaments.

FIG. 17B shows a cross-section view of the planarly cohesive separator sheet 1000. In one embodiment the members 1010 and members 1012 are polymeric monofilaments and are fused together at the point of contact, for example, by melting the filaments at the point of contact 1015. The arrangement of members 1010 and members 1012, here fused polymeric monofilaments creates open cells 1014, which enable the packing of adsorptive beads. The planarly cohesive separator sheet 1000 is used to create a stress absorbing substantially rigid structure capable of withstanding compressive and tensile stresses, both of which are present when fluid is pumped creating a liquid flow into a planarly cohesive adsorptive beds or composite adsorptive beds in chromatography columns.

Substantially rigid as used herein, generally means that the deformation of the rigid structural members and the whole scaffold under the stress loads encountered in the application is sufficiently small to be imperceptible in the performance of the adsorptive bed. Functionally this generally means that the adsorptive bed does not move under the applied stresses and, therefore, does not experience voiding, channeling or increased hydraulic resistance due to crushing of the beads. Substantially rigid structural members and their corresponding scaffolds absorb the stresses induced within the composite adsorptive bed by the pressure gradients created by liquid flowing through the bed, thereby preventing these stresses from blowing apart the peripheral seals in stackable planar adsorptive devices, or crushing the beads in conventional chromatography columns Hereafter "rigid" means "stress absorbing substantially rigid," when referring to either structural member, separator sheets or scaffolds.

Now referring to FIG. 18A, a planarly cohesive separator sheet 1100 similar to the planarly cohesive separator sheet 1000 of FIG. 17A includes a woven screen 1104 with a plurality of rigid structural members 1110a-1110n (generally referred to as members 1010) and a plurality of rigid structural members 1112a-1112m (generally referred to as members 1012) woven together to define the plurality open cells 1114. Here the woven screen 1104 is formed with two arrays of parallel polymeric monofilaments, each array of filaments running in a direction perpendicular to the other and woven together.

FIG. 18B shows a cross-section view of the planarly cohesive separator sheet 1100. In contrast to the planarly cohesive separator sheet 1000, the members 1110 and 1112 are woven together and are not fused together. In other embodiments selective fusing of the members 1110 and members 1112 can be used to render the separator sheet 1100 more rigid.

Figure 19A:
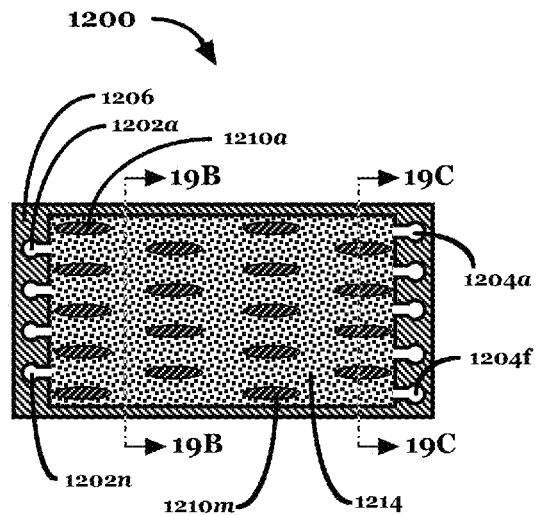
FIG. 19A is a schematic diagram showing a planarly cohesive separator sheet based on a molded plate according to aspects of the invention.

Now referring to FIG. 19A, a planarly cohesive separator sheet 1200, here a molded plate 1200, includes a bottom planar surface 1220, top planar surface (not shown), edge seals 1206 (also referred to as peripheral seals) and spacers 1210a-1210m (generally referred to as spacers 1210). Molded plate 1200 also includes feed distribution passages 1202a-1202n and eluent distribution passages 1204a-1204m to introduce and collect liquid fed to the composite planarly cohesive adsorptive bed and eluent distribution passages 1204a-1204f to collect the liquid after having been exposed to the composite adsorptive bed.

Figure 19B:
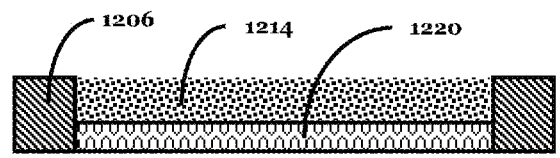
FIG. 19B is a cross section view of the planarly cohesive separator sheet taken along section 19B-19B of FIG. 19A.
Figure 19C:
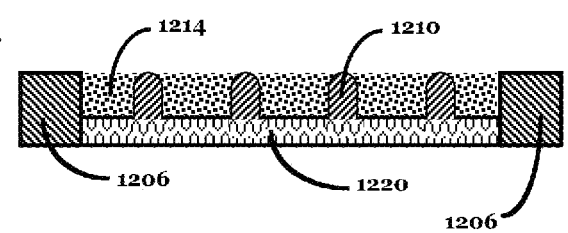
FIG. 19C is a cross section view of the planarly cohesive separator sheet taken along section 19C-19C of FIG. 19A.

FIGS. 19B and 19C are cross-sectional views of molded plate 1200 showing the beads 1214 packed into the open cells formed by the rigid structure which includes the flat bottom 1220, edge seals 1206 and spacers 1210. Spacers 1210 maintain the spacing between molded plate 1200 and an adjacent molded plate (not shown) when stacked together forming a rigid structure. The open cells of the molded planarly cohesive separator sheet 1200 enables liquid introduced through feed passages 1202 to flow through the composite adsorptive bed and collected by the eluent passages 1204.

Figure 20A:
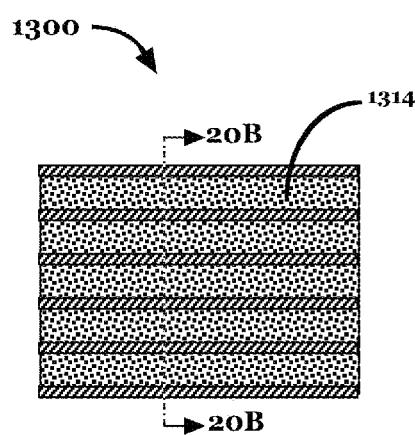
FIG. 20A is a schematic diagram showing a planarly cohesive separator sheet based on an extruded sheet according to aspects of the invention.
Figure 20B:
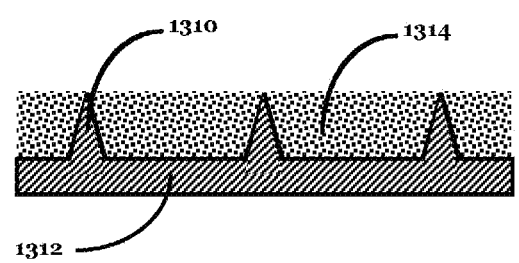
FIG. 20B is a cross section view of the planarly cohesive separator sheet taken along section 20B-20B of FIG. 20A.

Now referring to FIG. 20A a planarly cohesive separator sheet 1300, here an extruded sheet 1300, includes a flat bottom 1312 and spacers 1310a-1310m (generally referred to as spacers 1310). FIG. 20B is a cross-sectional view of extruded sheet 1300 showing the beads 1314 packed into the open cells formed by the rigid structure of the flat bottom 1312 of the of extruded sheet 1300 and spacers 1310. Spacers 1310 maintain the spacing between extruded sheet 1300 and an adjacent extruded sheet (not shown) when stacked together forming a rigid structure. Adsorptive beads 1314 fill the open cells of the extruded sheet 1300.

Figure 21A:
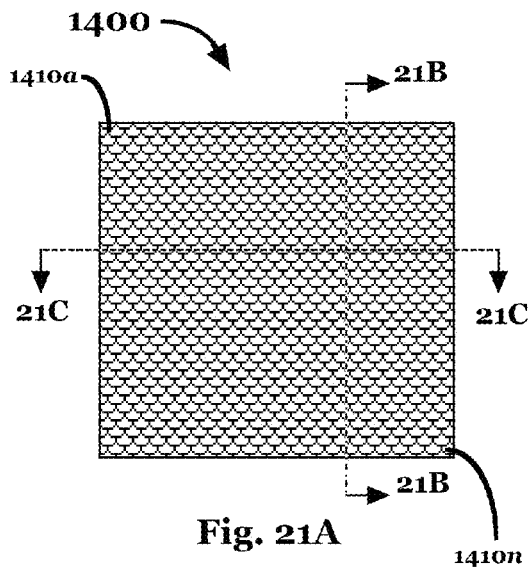
FIG. 21A is a schematic diagram showing a planarly cohesive separator sheet based on a perforated plate or sheet according to aspects of the invention.
Figure 21B:
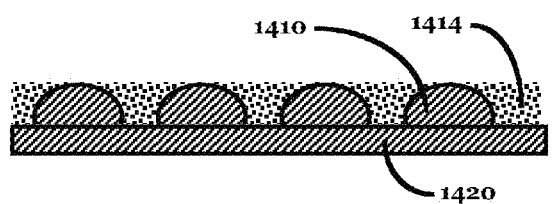
FIG. 21B is a cross section view of the planarly cohesive separator sheet taken along section 21B-21B of FIG. 21A.
Figure 21C:
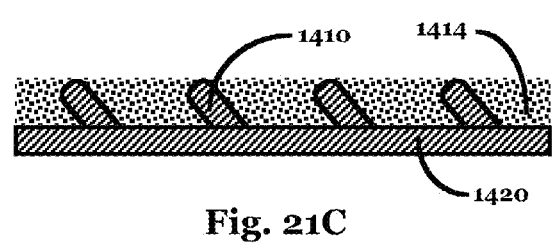
FIG. 21C is a cross section view of the planarly cohesive separator sheet taken along section 21C-21C of FIG. 21A.

Now referring to FIG. 21A a planarly cohesive separator sheet 1400, here, a perforated plate 1400, includes a flat bottom 1420, and spacers 1410a-1410m (generally referred to as spacers 1410). Spacers 1410a-1410m are created by perforating a thin plate, wherein the material removed at the perforations remains attached to the flat bottom 1420 of the perforated plate but bent relatively to the plane of the perforated plate. FIG. 21B is a cross-sectional side view of perforated plate 1400 showing adsorptive beads 1414 packed into open cells formed by the rigid structure of the flat bottom 1420 of the perforated plate 1400 and spacers 1410. Spacers 1410 maintain the spacing between perforated plate 1400 and an adjacent perforated plate (not shown) when stacked together forming a rigid structure. The open cells of the perforated plate 1400 enable liquid flow through the perforated plate 1400. FIG. 21C is a cross-sectional side view of perforated plate 1400 in a direction perpendicular to the side view shown on FIG. 21B, whereby the perforations forming the spacers 1410 are being viewed along their flat dimension. The spacers 1410 created by the perforations may be aligned or may be staggered to improve the flow uniformity as shown in this example.

Figure 22A:
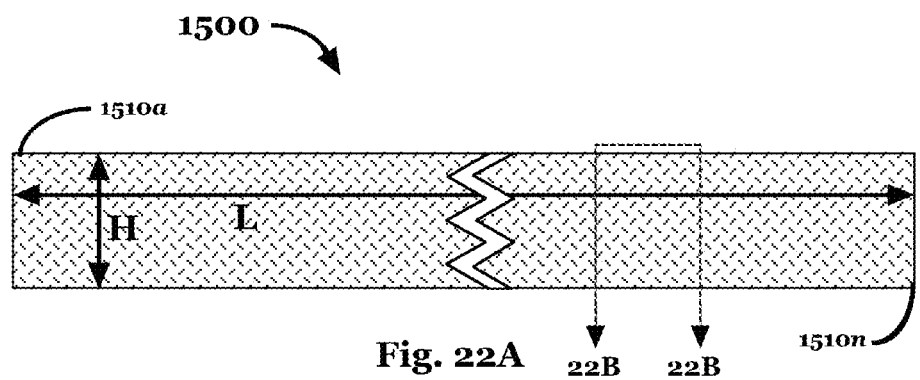
FIG. 22A is a schematic diagram showing a planarly cohesive separator sheet based on a sintered sheet of randomly packed rods or fibers according to aspects of the invention.
Figure 22B:
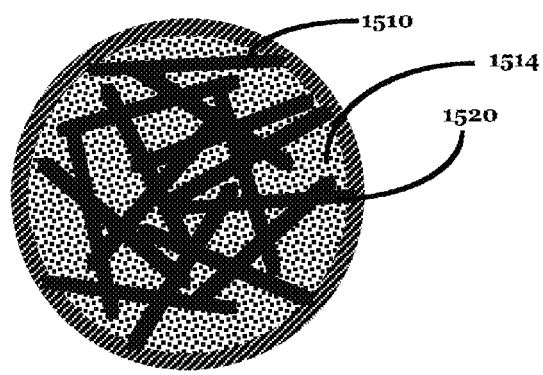
FIG. 22B is a cross section view of the planarly cohesive separator sheet taken along section 22B-22B of FIG. 22A.

Now referring to FIG. 22A a planarly cohesive separator sheet 1500, here, a porous non-woven web 1500, includes randomly packed fibers 1510a-1510n, which are bonded into a rigid structure. The rigid structure of non-woven web 1500 includes a plurality of open cells filled with adsorptive beads 1514 forming a composite planarly cohesive adsorptive bed. FIG. 22B is a magnified cross-sectional view of non-woven web 1500 showing the beads 1514 packed in the open cells created by the rigid structure, which restricts movement of the beads. The non-woven web 1500 has a length L and a thickness H. If the thickness H of non-woven web 1500 is very large, e.g., more than 1 cm and even more than 5 cm, then non-woven web 1500 becomes a porous monolith that provides an adsorptive bed without the need to stack a plurality of separator sheets 1500.

In other embodiments, the planarly cohesive separator sheet is formed by randomly packed packing pieces bonded into a planarly cohesive sheet (not shown). Suitable packing pieces can have any shape and size as long as they form a rigid scaffold having void space in the form of open cells. Examples of suitable packing pieces include, but are not limited to, those used in packed distillation and extraction columns (e.g., Rashig rings; Splined Rings; Pall Rings; Berl Saddles; glass shot; Helices; Nutter Rings; Super Plastic Sphere) and any others known to those skilled in the art of distillation and extraction. In some embodiments the same packing pieces used in distillation and extraction columns may be suitable packing pieces for scaffolds disclosed herein; in other embodiments requiring a smaller packing piece, similarly shaped packing pieces but of a smaller dimension are used.

In these embodiments the open cells of the void space have to be sufficiently large to enable the beads to flow into these void spaces and pack them tightly. The size of the open cells can be characterized by the diameter of the largest sphere that can be inscribed inside the open cell. Since all of the plurality of open cells created by the void space are not identical, the population of open cells can be characterized by their average diameter (hereafter referred to as a characteristic diameter). The open cells of the composite adsorptive beds disclosed herein need to have a characteristic diameter that is at least about 10 times larger than the average diameter of the adsorptive beads in order to enable uniform and effective packing of the open cells of the void space.

Certain embodiments of planar adsorptive devices suitable for beads as described above in FIGS. 18 to 22 include packing retainers to retain the beads within the void space of the structural scaffold. Packing retainers are generally located on the effluent end of the adsorptive bed, between the packed bed of beads and the eluent collectors. In some embodiments there are packing retainers in both the feed and the eluent end between the feed distributor and the eluent collector, respectively. In this manner the adsorptive beads are retained forming a stationary bed.

In one embodiment, packing retainers are made with sintered ceramic or glass porous media formed into rods, discs or sheets with a pore size smaller than the size of the adsorptive beads. In other embodiments, the porous media is plastic (e.g., porous polymer material made by Porex Corporation, Atlanta Ga.), metal (e.g., porous metal made by Mott Corporation, Farmington, Conn.) or microporous membranes (e.g., Millipore Corporation, Billerica Mass.). Packing retainers may be fabricated separately and inserted into the device, or may be formed in situ within the device, the important aspect being the use of packing retainers in bead-based devices.

In other embodiments, packing retainers are formed by molding thin channels into a plastic part, with the thin channels having dimensions smaller than the size of the adsorptive beads. This is particularly useful for embodiments that use molded plates to form the planarly cohesive scaffolds such as those shown in FIG. 19A. In still other embodiments packing retainers are formed by a combination of thin channels and secondary beads or particles larger than the adsorptive beads. The thin channels retain the (large) secondary beads, which in turn retain the smaller adsorptive beads. For example, thin molded channels may have a channel depth of about 100 µm, the secondary beads may have a diameter of about 150 µm, whereas the adsorptive beads have a diameter of about 30 µm. The pore size of the bed of larger secondary beads is about 20 µm, effectively retaining the adsorptive beads. The larger secondary beads may be made of plastic, metal, ceramic or glass. The combination of thin channels and larger secondary beads allows the molding of larger channels while still retaining much smaller adsorptive beads. In another embodiment, packing retainers are inserted between each layer of planarly cohesive webs, or molded into each layer. In other embodiments packing retainers are inserted or molded into a finished structural scaffold having a peripheral seal and distribution and collection passageways on the feed and eluent end, as described in more detail below in FIGS. 36, 37, 40 and 41.

FIGS. 23A and 23B are schematic diagrams of composite beds comprising a rigid scaffold formed by stacking separator sheets of the type shown in FIG. 17 and adsorptive beads packed into the open cells created by the rigid structure of the scaffold. Now referring to FIG. 23A, an adsorptive bed 1600 includes a housing 1602 having a first surface 1604 and a scaffold 1606 disposed within the housing in contact with the first surface 1604. The scaffold 1606 includes a stress absorbing substantially rigid structure 1608 and a plurality open cells 1614a-1614n (collectively referred to as open cell 1614) disposed within the rigid structure 1608. The adsorptive bed 1600 further includes a plurality of adsorptive beads 1616 filling the plurality of open cells 1614 forming a packed bed of the plurality of adsorptive beads.

Here, the stress absorbing substantially rigid structure 1608 includes a plurality of stacked planarly cohesive separator sheets 1000a-1000n (collectively referred to as separator sheet 1000), each of the plurality of stacked planarly cohesive separator sheets 1000 being in intimate contact with adjacent ones of the plurality of stacked planarly cohesive separator sheets 1000, and each of the plurality of stacked planarly cohesive separator sheets 1000 include a plurality of rigid structural members arranged to define the plurality open cells 1614.

In one embodiment, the separator sheets 1000 are stacked on top of each other such that the members that form the rigid structure of scaffold 1600 are lined up. Scaffold 1600 has void space in the form of open cells that are filled by adsorptive beads, which are packed into a bed. FIG. 23B is a schematic of another embodiment of scaffolds disclosed herein. Scaffold 1700 is formed by stacking separator sheets of the type shown in FIG. 17. Separator sheets 1000 are stacked on top of each other such that the filaments that form the rigid structure of scaffold 1600 are staggered. Scaffold 1700 has void space in the form of open cells that are filled by adsorptive beads, which are packed into a bed. It should be understood that the separator sheets can be stacked such that the open cells are substantially aligned as in FIG. 23A, or that the open cells are staggered in a repeating sequence as shown in FIG. 23B, or in any various staggered orientations. An important aspect of the stacking is that the scaffold created is substantially rigid and the void spaces of the rigid structure of the scaffold create a plurality of open cells.

In operation the adsorptive bed 1600 receives a liquid flow and the scaffold 1606 restricts movement of the plurality of adsorptive beads 1614, absorbs compressive stress induced by a hydraulic pressure gradient along a direction of the liquid flow and transfers a portion of the induced compressive stress to the first surface 1604 of the housing 1602.

The planarly cohesive scaffolds and separator sheets described in FIGS. 17A-23B can be used to create composite adsorptive beds suitable for stackable planar adsorptive devices (requiring planarly cohesive adsorptive media), or alternatively, can be used to create composite adsorptive beds suitable for chromatography columns. When used in chromatography columns the composite adsorptive beds disclosed herein enable the use soft beads packed into conventional chromatography columns and operated at pressures substantially higher than in conventional operation. Operating at these high pressures, for example, greater than 100 psi is not possible without the structural support provided by the rigid scaffold. In these embodiments the rigid scaffold of the composite adsorptive bed absorbs the compressive stress created by the liquid flow, whereas the relatively soft adsorptive beads packed into the void space of the rigid structure provide the adsorptive media for the separation. Without the rigid scaffold a large class of soft beads (e.g., agarose and sepharose beads) cannot be used at high pressures, limiting the length of the column and/or the velocity of the mobile phase used in the chromatographic separation and/or the size of the adsorptive bead that can be used. In one embodiment, the adsorptive bed supports a liquid flow velocity greater than 150 cm/hour. In planar stackable devices the adsorptive media needs to be planarly cohesive to withstand the hydrostatic pressures within the device as well as the pressure gradients created by the liquid flow. All of the stresses created by liquid flow want to blow apart the device, requiring adsorptive media that is planarly cohesive to withstand the tensile stresses. In contrast, conventional chromatography columns have a rigid housing capable of withstanding the pressure, however, the pressure gradients induced by liquid flow create a compressive stress that must be withstood by the adsorptive bed.

Figure 24A:
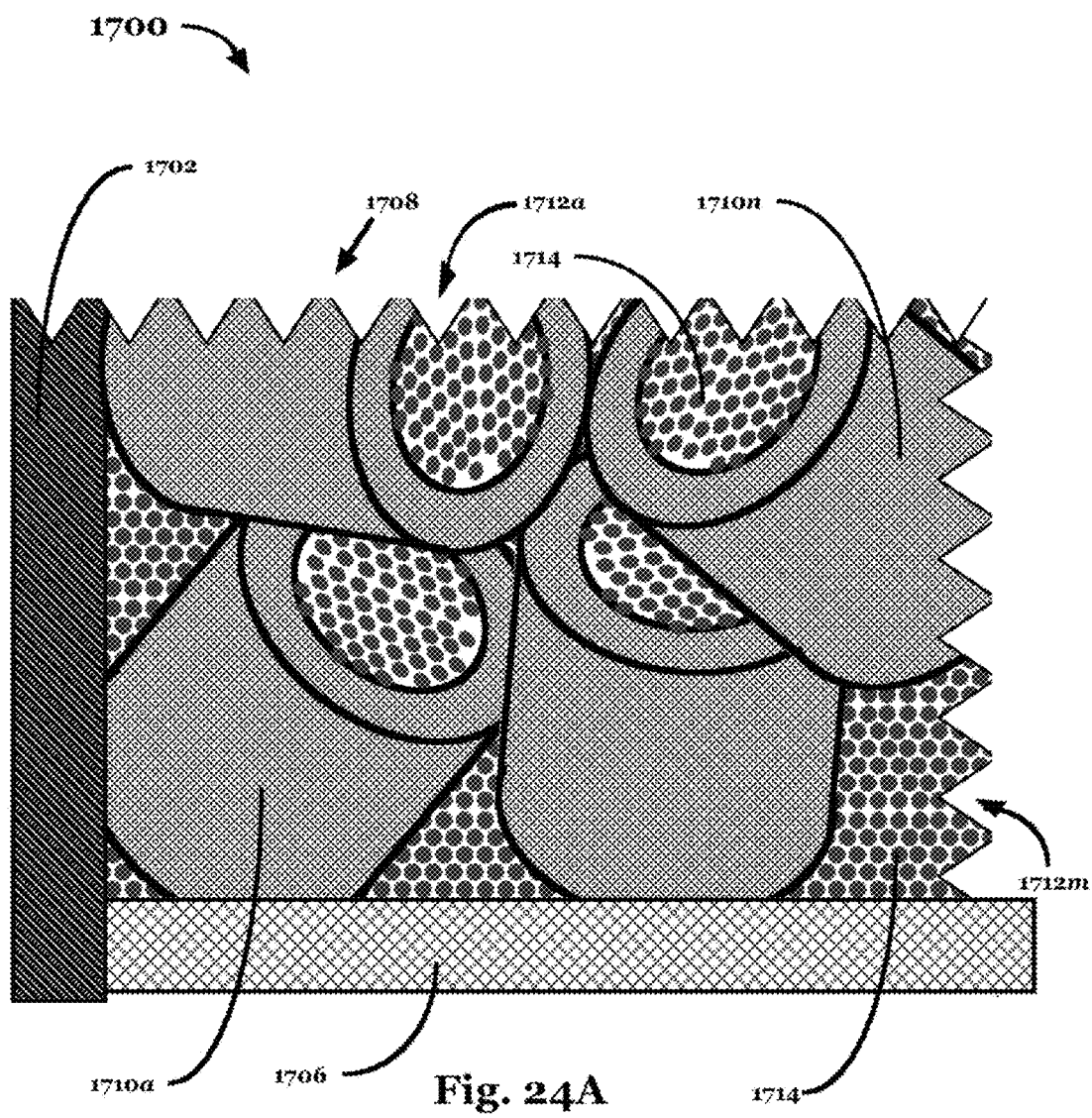
FIG. 24A is a schematic diagram showing a adsorptive bed having a rigid structure comprising a plurality of randomly packed Raschig rings packed into a chromatography column according to aspects of the invention.

FIG. 24A shows a portion of a composite bed 1700 which includes a scaffold 1702 having a rigid structure including a plurality of randomly packed packing pieces 1710a-1710n (collectively referred to as packing pieces 1710). Each one of the plurality of randomly packed packing pieces 1710 is made from a rigid structural material and the plurality of randomly packed packing pieces 1710 are arranged to define the plurality of open cells 1712a-1712m (collectively referred to as open cell 1712) formed by the packing pieces 1710. Here the packing pieces 1710 are Raschig Rings. The packing pieces 1710 include, but are not limited to, a Lessig Ring, a Splined Ring, a Pall Ring, a Berl Saddle, a glass shot, a helix, a Nutter Ring and a Super Plastic Sphere. It is understood that various type of packing pieces 1710 can be intermixed. In one embodiment the plurality of randomly packed packing pieces 1710 are randomly packed one on top of each other in a chromatography column, and beads 1714 packed into the open cell 1712 void space formed by the rigid structure of the scaffold. The packing pieces within a chromatography column form a rigid structure supported by the column bottom 1706 and the column sidewalls 1702. The rigid scaffold restricts the movement of the beads and absorbs the compressive stress created by the liquid flow preventing the beads from getting crushed.

Figure 24B:
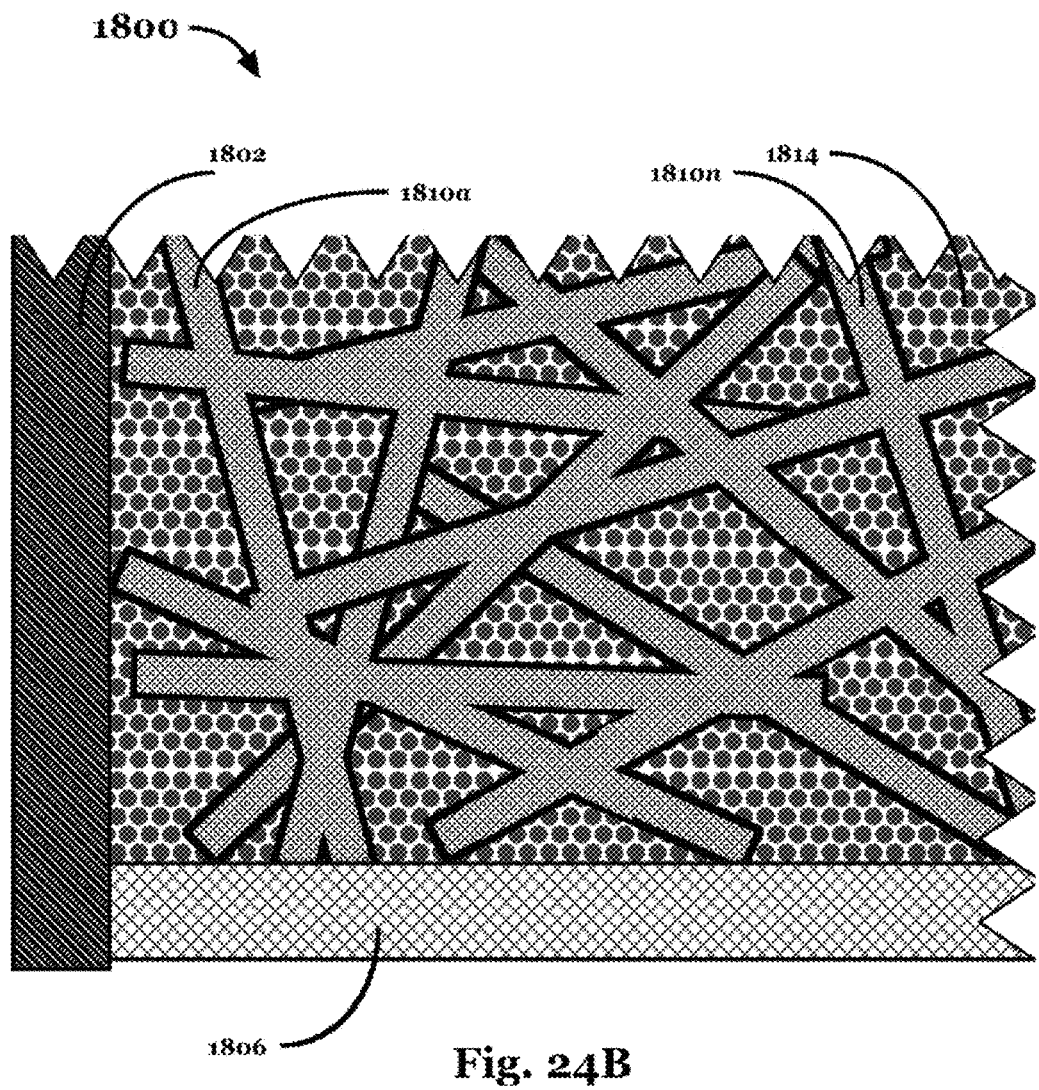
FIG. 24B is a schematic diagram showing an adsorptive bed having a rigid structure comprising a plurality of randomly packed filaments packed into a chromatography column according to aspects of the invention.

FIG. 24B shows a composite bed 1800 comprising a scaffold formed by packing pieces 1810a-1810n (generally referred to as packing pieces 1810), here, filaments which are randomly packed one on top of each other in a chromatography column, and beads 1814 packed into the void space formed by the rigid structure of the scaffold. The packing pieces within a chromatography column form a rigid structure supported by the column bottom 1806 and the column sidewalls 1802. The rigid scaffold restricts the movement of the beads and absorbs the compressive stress created by the liquid flow preventing the beads from getting crushed. In some embodiments packing pieces 1710 and 1810 of composite adsorptive beds 1700 or 1800 can be fused, bonded or sintered together prior to packing the open cells with adsorptive beads (not shown).

Beads may be introduced into the void space by dry packing or slurry packing methods known to those skilled in the art. In some embodiments the beads are introduced into the scaffold gradually as the separator sheets are stacked. In other embodiments the beads are introduced after the whole scaffold is fabricated into a planarly cohesive device or arranged inside the chromatography column. In still other embodiments it may be possible to introduce the adsorptive beads into individual separator sheets.

Figures 25A, 25B:
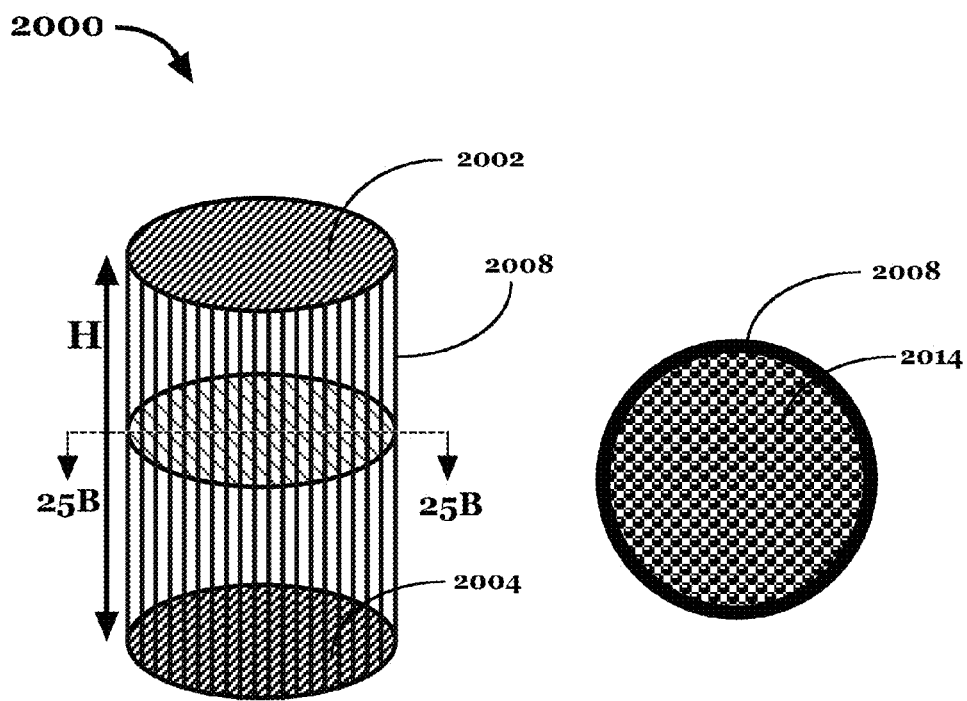
FIGS. 25A-25B are schematic diagrams showing a conventional chromatography column.

FIG. 25A is perspective view of a prior art chromatography column in wire-frame format. Chromatography column 2000 has sidewalls 2008, bottom planar surface 2004 and top surface 2002. Chromatography column 2000 is packed with adsorptive beads (not shown) to form an adsorptive bed of height H. FIG. 25B is a cross-sectional view of column 2000 showing adsorptive beads 2014 supported by sidewalls 2008. In operation column 2000 is fed a liquid to a distributor (not shown) at the top surface 2002. Due to the hydraulic resistance of the adsorptive bed formed by the packing of adsorptive beads 2014, the fluid must be a pumped under pressure, which creates a hydrostatic pressure within the column 2000 as well as a pressure gradient. The forces developed by the hydrostatic pressure are restrained by the sidewalls 2008 and top and bottom surfaces 2002 and 2004, respectively. The pressure gradient created by each layer of beads in the packed bed builds a compressive stress on the packed bed that increases along the flow direction of the liquid. As a result, the beads at the bottom of the packed bed, adjacent to the bottom surface 2004, are being compressed by the hydraulic pressure gradient from the top to the bottom surfaces, hereafter referred to as the pressure drop. Soft agarose and sepharose beads commonly used in the purification of biomolecules start to deform when subjected to compressive pressures of about 25~50 psi. For this reason chromatography columns packed with these types of soft beads can't be operated at flow rates that generate pressure drops within the column that exceed 50 psi, and preferably 30 psi. The compressive stress limitation of soft beads significantly limits the conditions at which such chromatography columns can be operated. More specifically, such columns must be relatively short (e.g., typically less than 50 cm), must be operated at relatively low flow velocities (e.g., typically less than 150 cm/hr) and must utilize relatively large beads (e.g., typically not less than 90-100 µm in diameter). The net result is that chromatography columns are difficult to scale up, and the processes have a low productivity leading to large columns and/or long processing times.

Figure 26A:
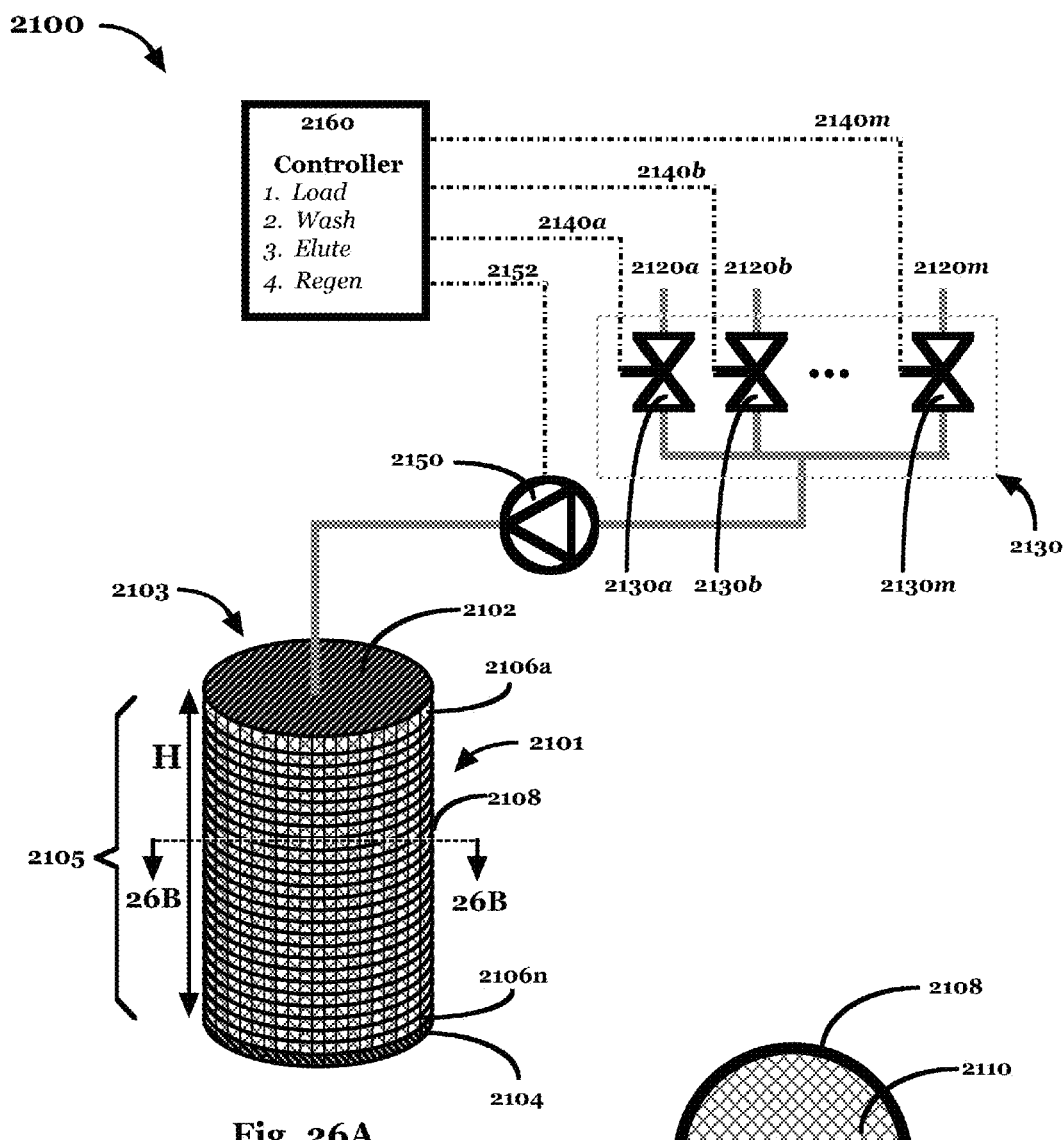
FIG. 26A is a schematic diagram showing a adsorptive bed having a rigid structure scaffold of stacked planarly cohesive separator sheets packed into a chromatography column coupled to a quick cycle controller according to aspects of the invention.

Now referring to FIG. 26A, a chromatography system 2100 includes an adsorptive bed 2105 including scaffold 2101, here packed into a chromatography column 2103 acting as a housing. The chromatography system 2100 further includes a rapid cycling controller 2160, at least one pump 2150 and at least one valve 2130a controlling a liquid feed stream. The rapid cycling controller 2160 is coupled via control line 2152 to the pump 2150 and control line 2140a to valve 2130a controlling a liquid feed stream. It is understood that multiple pumps and valves 2130a-2130n with corresponding control line 2140a-2140n can be used to control the system. The chromatography column 2103 includes sidewalls 2108, bottom surface 2104 and top surface 2102. Column 2103 is packed with a composite adsorptive bed 2105 comprising a rigid scaffold 2101 having void space in the form of open cells, and adsorptive beads (not shown) packed into the open cells as shown in the embodiments described in FIGS. 17 to 24. The scaffold 2101 disposed within the chromatography column housing 2103 is in contact with the bottom surface 2104 (also referred to as the first surface). The scaffold 2101 acts as a rigid structure absorbing the compressive stress induced on the adsorptive bed along a direction of the liquid flow (indicated along the double arrow labeled "H"). The scaffold 2101 restricts movement of the plurality of adsorptive beads, absorbs compressive stress induced by hydraulic pressure gradient along the direction of the liquid flow and transfers a portion of the stress to the first surface of the housing, here, the bottom surface 2104 of the chromatography column housing 2103.

Figure 26B:
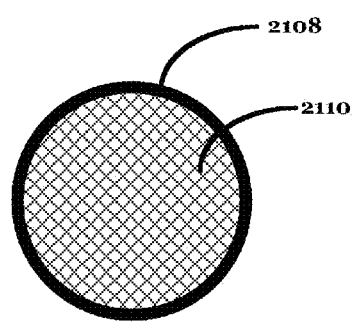
FIG. 26B is a schematic diagram showing a cross section of the chromatography column taken along section 26B-26B of FIG. 26A.

In one embodiment the rigid scaffold 2101 comprises a stack of separator sheets 2106a-2106n (collectively referred to as separator sheets 2106) that have been cut to the same shape (i.e., diameter) as the interior diameter of the chromatography column. The stack of separator sheets 2106 fills the interior of the chromatography column creating a rigid scaffold of height H, with void space in the form of open cells packed with adsorptive beads (not shown). FIG. 26B is a cross-section view of column 2103 showing sidewalls 2108 and composite adsorptive bed 2110 comprising a rigid scaffold comprising with open cells formed by separator sheets 2106, and adsorptive beads (not shown) packed into the open cells. In other embodiments, the scaffold 2101 is similar to the scaffolds shown in FIGS. 24A and 24B.

In contrast to the chromatography columns of the prior art, the rigid scaffold restricts the movement of the adsorptive beads and absorbs the compressive stress generated by the pressure gradients generated by the adsorptive bed, enabling the utilization of soft beads in columns having pressure drops exceeding 100 psi. Such pressures are generated when beads smaller than 100 µm are packed into columns that are longer than 50 cm and/or operated at mobile phase velocities exceeding 150 cm/hr. In some embodiments pressure drops greater than 300 psi are generated, which may be necessary when utilizing soft beads smaller than 50 µm in diameter. In still other embodiments pressure drops greater than 300 psi are generated, which may be necessary when utilizing soft beads smaller than 25 µm in diameter.

In operation, chromatography system 2100 feeds the chromatography column 2103 using the pump 2150. In one embodiment the pump 150 is capable of generating pressures exceeding 100 psi. The rapid cycling controller 2160 controls the pump 2150 and valves 2130a-2130m (collectively referred to as valve array 2130) by means of control lines 2140a-2140m (collectively referred to as control lines 2140). Valve array 2130 selects one of several feed streams 2120a-2120m (collectively referred to as feed streams 2120) as necessary to effect a multi-step chromatography process. Multi-step chromatography processes typically utilize at least four feed streams 2120, which are fed sequentially to affect at least four steps: load; wash; elute; and regenerate.

These streams are fed at varying mobile phase velocities and for varying times following conditions selected by the rapid cycling controller 2160. In one embodiment, a purification process includes adsorbing target solute in the adsorptive bed, washing non-adsorbed solutes, releasing purified target solute, and conditioning the adsorptive bed for a next purification cycle. In one embodiment, the rapid cycling purification process has a rapid purification process cycle time less than about ten minutes, in another embodiment a rapid purification process cycle time less than about twenty minutes and in another embodiment a rapid purification process cycle time less than about thirty minutes.

The sequence of steps in such multi-step chromatographic processes is required to yield the desired purified solute; therefore, the multi-step sequence has to be exercised at least once in order to obtain a purified solute. It is possible to carry out the multi-step sequence more than once for a given manufacturing batch in order to process a larger amount of feed stream utilizing a chromatography column that is not capable of adsorbing the full batch in one step. In this manner, a smaller chromatography column can be used to process amounts that would require a larger column Such multi-cycle chromatography processes are increasingly common, typically cycled two to five times. It would be particularly advantageous to cycle a chromatography column a dozen times with a single manufacturing batch, and even more advantages to cycle the column more than 100 times, since the larger the number of cycles the smaller the column and the lower the cost. Although such rapid cycling processes are clearly advantageous to reduce the cost of a chromatographic column, and in particular, the cost of adsorptive media, rapid cycling is only possible with smaller diameter beads operated at high mobile phase velocities. Adsorptive beds having scaffolds with rigid structures as described above restrict the movement of the adsorptive beads and support them to enable rapid cycling chromatography processes utilizing soft beads.

Although the term "bead" generally refers to a particle in the form of a small sphere, it should be understood that the term adsorptive beads as used in this invention refers to adsorptive particles that may or may not be spherical. The materials comprising the scaffolds include, but are not limited to, plastic, metal or ceramic materials.

Referring again to FIG. 26A, in some embodiments pump 2150 can pump the liquids at pressures exceeding 300 psi, and the adsorptive bed can include adsorptive beads having diameters of approximately 50 μm. In still other embodiments pump 2150 can pump the liquids at pressures exceeding 500 psi the adsorptive bed can include adsorptive beads having diameters of approximately 25 μm. In some embodiments separator sheets 2106 may be stacked from the bottom surface 2104 to the top surface 2102 to create the rigid scaffold. To make sure the scaffold is sufficiently rigid the stack of separator sheets 2106 may be pre-compressed to a compressive stress that exceeds the anticipated pressure drop at which the column 2103 will be run before the top surface 2102 is attached to the column sidewalls 2108. The adsorptive beads may be packed into the open cell created by the rigid scaffold by pumping a slurry of beads through the column 2103 utilizing methods know to those skilled in the art. In such slurry packing process the beads gradually fill the void space in layers from bottom surface 2104 to top surface 2102 as the slurry is pumped through the column until the composite adsorptive bed becomes fully packed.

Other alternative embodiments of the adsorptive devices (referred to herein as Chromassette-S or Chromassette-Shallow Bed) differ from the embodiments described above in that the direction of fluid flow through the adsorptive media (i.e., the flow streamlines) are perpendicular (rather than parallel) to the planar surfaces of the planarly cohesive media. These embodiments are very similar to the Chromassette embodiments described above: the Chromassette-S adsorptive devices have the form and shape of a planar cassette enabling them to be stackable and linearly scalable, just as Chromassette adsorptive devices; furthermore, they can be used with web-based or bead-based adsorptive media, just as Chromassette adsorptive devices. There are two distinct differences between Chromassette and Chromassette-S adsorptive devices: Chromassette-S adsorptive devices comprise additional first and second planar distributors to distribute the fluid across the planar surface and to collect the fluid from the planar surfaces of the inventive adsorptive devices, respectively; the flow direction through the adsorptive media is perpendicular to the planar dimension of the planarly cohesive adsorptive media. The Chromassette-S embodiments are particularly suited for adsorptive media having low hydraulic permeability, which in turn limits the depth of the adsorptive bed. These devices are referred to herein as embodiments having shallow bed configuration.

The adsorptive devices described below require the use of planarly cohesive adsorptive media (or simply, planarly cohesive media), which is adsorptive media possessing significant tensile strength along its planar dimensions, and thus enabling it to support the hydraulic pressures that will be generated by the fluids being processed through the adsorptive devices. The adsorptive devices of this invention further comprise an edge seal adhered to the circumference or periphery of the planarly cohesive media, hereafter the peripheral seal, capable of withstanding the forces generated by the hydraulic pressure within the adsorptive device. It is, therefore, one feature of these devices to include a combination of planarly cohesive media having sufficient tensile strength to withstand the hydraulic forces within the adsorptive device in use and peripheral seals adhered to the periphery of the adsorptive media having sufficient adhesion force to prevent delamination of the peripheral seal from the adsorptive media. The degree of planar cohesion of the planarly cohesive media and the degree of adhesion of the peripheral seal to the periphery of the planarly cohesive media will be dictated by the hydraulic pressures at which the device will operate.

In general, the degree of cohesion of the planar adsorptive media and the degree of adhesion of the peripheral seal to the adsorptive media at its interface can be characterized by their tensile strength, which can be measured in units of force per unit cross-sectional area, or in pounds per square inch, or "psi", in British units. The tensile strength of such elements can be readily measured by placing a rectangular coupon of the adsorptive media in a tensile strength testing apparatus, for example, testers made by Instron Corporation. In these tests, the coupon is held in opposite ends by clamps that very slowly pull the coupon apart while simultaneously measuring the distance between the two clamps and the restraining force induced by the coupon. Furthermore, the inherent tensile strength of a material is best characterized by its Young's or tensile modulus (or elastic modulus), which is equal to the tensile strength per unit strain (the Young's modulus is defined as the slope of the stress vs. strain response within the region where the material behaves according to Hooke's Law—i.e., having a linear stress vs. strain curve). Planarly cohesive media for devices of this invention should have a Young's modulus exceeding 500 psi, preferably exceeding 1,500 psi and most preferably exceeding 5,000 psi; peripheral seals of this invention should have adhesion strengths that exceed 50 psi, preferably 150 psi and most preferably 500 psi (the adhesion strength being defined as the tensile strength of the interface between the adsorptive bed and the peripheral seal).

Figure 27:
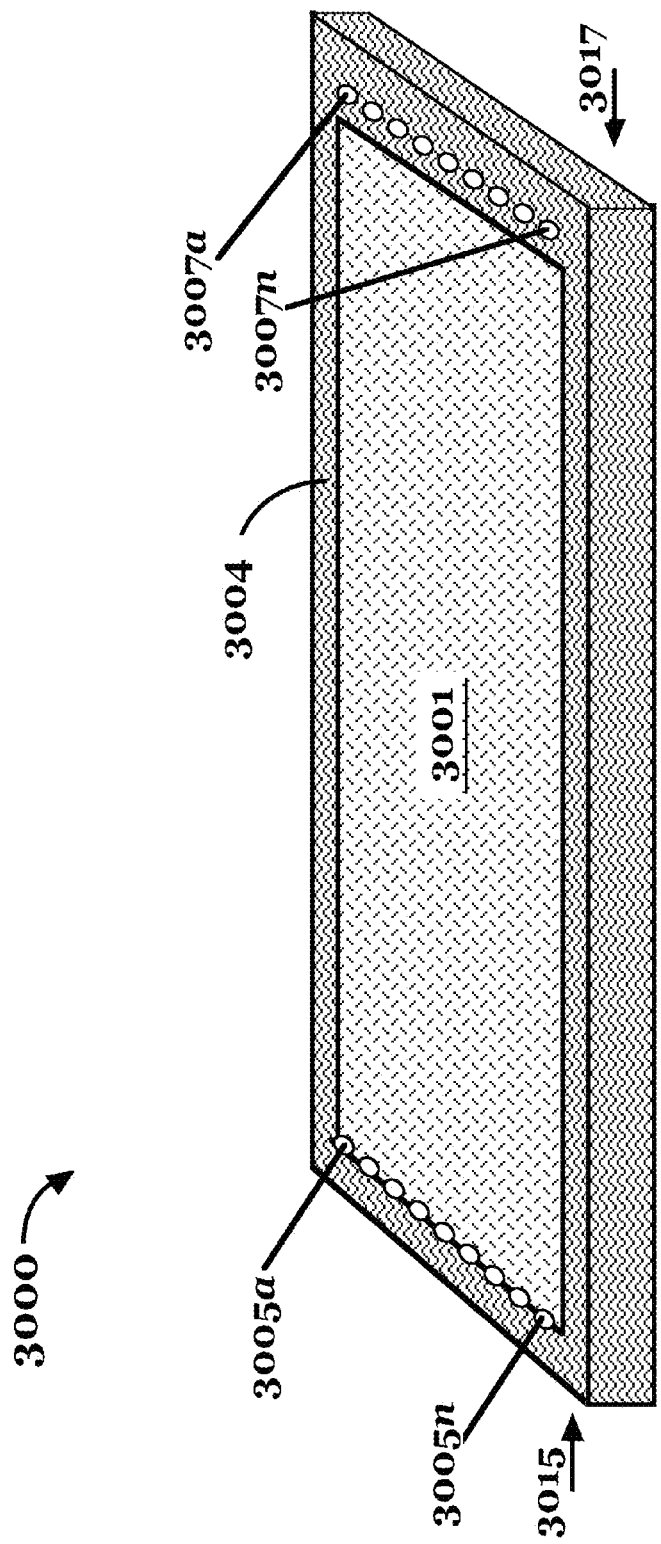
FIG. 27 is a perspective view of a Chromassette-S adsorptive device according to an aspect of the invention.

FIG. 27 is a perspective view of a Chromassette-S adsorptive device. The adsorptive device 3000 comprises first distribution passageways 3005a-3005n (collectively, distribution passageways 3005) at a first end 3015 of adsorptive device 3000, second distribution passageways 3007a-3007n (collectively, distribution passageways 3007) at a second end 3017 of adsorptive device 3000 and peripheral seal 3004. Adsorptive block (not shown) is sandwiched between first planar distributor 3001 disposed (or layered) on top planar surface of adsorptive device 3000 and second planar distributor disposed (or layered) on bottom planar surface of adsorptive device 3000. First planar distributor 3001 is in fluid communication with first distribution passageways 3005, but not with second distribution passageways 3007.

Now referring to FIGS. 28A and 28B, the adsorptive device 3000 comprises adsorptive block 3010, first and second planar distributors 3001 and 3003, and peripheral seal 3004. Adsorptive block 3010 comprises a plurality of planarly cohesive adsorptive media 3002a-3002n (collectively, adsorptive media 3002) stacked on top of each other; in this case, adsorptive block 3010 comprises five layers of planarly cohesive media. Adsorptive block 3010 is further bounded above and below by first planar distributor 3001 adjacent to the top of the adsorptive block 3010 and second planar distributor 3003 adjacent to the bottom of the adsorptive block 3010. Planar distributors 3001 and 3003 are in intimate contact with adsorptive block 3010. Peripheral seal 3004 seals the circumference of adsorptive block as well as the circumference of the first and second planar distributors 3001 and 3003 as described in more detail below. Adsorptive device 3000 is further characterized by having a first and second planar surfaces 3011 and 3013, respectively, and first and second ends 3015 and 3017, respectively.

The adsorptive device 3000 further comprises a first set of distribution passageways 3005 forming a first manifold (e.g., for distributing the feed stream across multiple adsorptive devices 3000 stacked on top of each other) and a second set of distribution passageways 3007 forming a second manifold (e.g., for collecting the effluent stream from multiple adsorptive devices 3000 stacked on top of each other). Distribution passageways 3005 and 3007 are substantially perpendicular to the planar surfaces of adsorptive device 3000. FIG. 28B shows adsorptive device 3000', identical in all respects to adsorptive device 3000 of FIG. 28A except that adsorptive block 3010' is thicker, comprising ten layers of planarly cohesive media 3002 instead of five.

The terms "top" and "bottom," as used herein, are purely descriptive and are used to simplify the description of the invention throughout the specification, the important aspect being that adsorptive device 3000 and adsorptive block 3010 have two planar surfaces, a first planar surface and a second planar surface, and that these two planar surfaces are on opposite sides of the adsorptive block. The two planar surfaces can be oriented horizontally as shown in FIG. 28A, in which case one is on the top and the other one is on the bottom of adsorptive block 3010; in other embodiments the first and second planar surfaces can be oriented vertically, in which case one is on the left and the other one is on the right of the adsorptive block 3010; in other embodiments the two planar surfaces can be in other orientations not aligned in any way to the direction of gravity. Furthermore, the description will adopt the convention that the first planar surface 3011 is on the top, in which case the second planar surface 3013 is on the bottom, but it should be understood that the planar surfaces, and corresponding planar distributors, might be in the opposite locations.

Peripheral seal 3004 completely seals the exterior of adsorptive device 3000. As shown in FIG. 28A and FIG. 28B sealing region 3004' of peripheral seal 3004 isolates adsorptive block 3010 and second planar distributor 3003 from first distribution passageways 3005. Likewise, sealing region 3004" of peripheral seal 3004 isolates adsorptive block 3010 and first planar distributor 3001 from second distribution passageways 3007. In contrast, first planar distributor 3001 is in fluid communication with first distribution passageways 3005 at interface 3006, which is accomplished by selectively preventing the sealing of interface 3006 by peripheral seal 3004. Likewise, second planar distributor 3003 is in fluid communication with second distribution passageways 3007 at interface 3008, which is accomplished by selectively preventing the sealing of interface 3008 by peripheral seal 3004. It is understood, in FIGS. 29A-29D that this sealing configuration creates the desired flow pattern on adsorptive devices of this invention. As will be described below the peripheral seal 3004 may be one of:

monolithic comprising a single continuous sealing medium for adsorptive device 3000;

pellicular (as in individual layers or pellicles)—each individual layer or web of planarly cohesive media 3001 that forms adsorptive block 3010 and the two planar distributors each have their own individual peripheral seals, such that when these layers are stacked and in intimate contact to each adjacent layer the plurality of individual peripheral seals form peripheral seal 3004; and two or more layers planarly cohesive media 3001 may be sealed together first and each planar distributor may be sealed individually, such that when these layers (having their own peripheral seals) are stacked and in intimate contact to each adjacent layer the plurality of individual peripheral seals form peripheral seal 3004.

Figure 31:
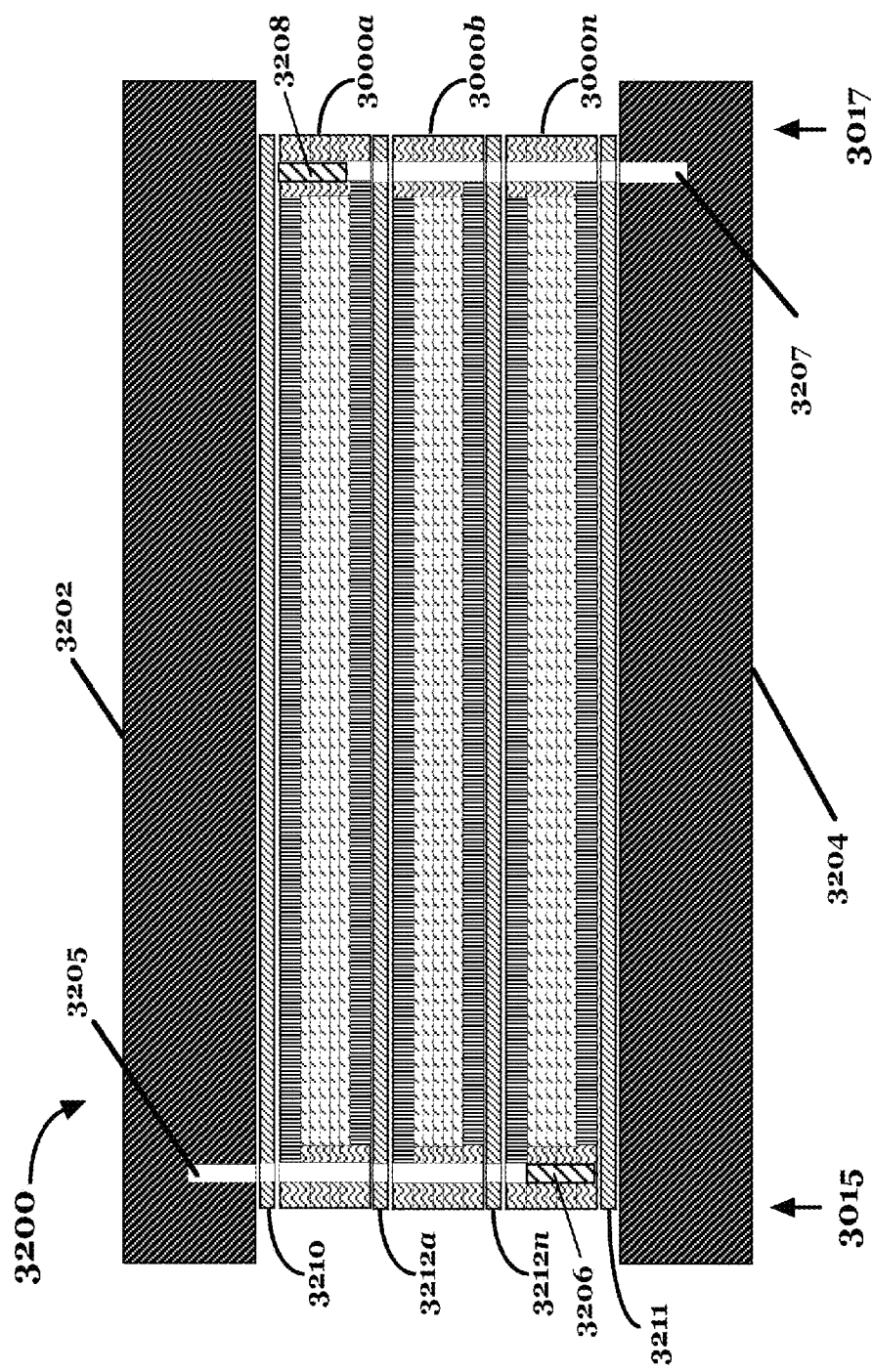
FIG. 31 is a cross-sectional side view of a Chromassette-S adsorptive device assembly having multiple Chromassette-S adsorptive devices of FIG. 27 stacked into a single adsorptive device assembly.

In one embodiment, adsorptive devices 3000 and 3000' have first and second planar surfaces 3011 and 3013, respectively, enabling them to be stacked on top of other adsorptive devices having the same footprint (i.e. having the same planar dimensions characterized by length, L and width W as shown in FIG. 29B for an adsorptive device having a rectangular footprint) and locations of distribution passageways 3005 and 3007. While adsorptive devices 3000 may be stacked with identical adsorptive devices or with adsorptive devices having different thicknesses or height (H in FIG. 28B), good adsorptive practice dictates that only identical adsorptive devices 3000 be stacked as shown in FIG. 31.

FIG. 29A and FIG. 29B show magnified views of first end 3015 and second end 3017 of adsorptive device 3000, respectively, with arrows representing the flow of the fluid being fed and collected from adsorptive device 3000. Main feed stream 3020 is distributed by top end plate (not shown) into entrance of first distribution passageways 3005. A portion of main feed stream 3020, subfeed stream 3022, is diverted and turned 90° into first planar distributor 3001 by virtue of being in fluid communication with first distribution passageways 3005. Feed stream 3022 is further split, distributed and turned back 90° by first planar distributor 3001 into a plurality of fluid streams at the top of adsorptive block 3026a-3026n (collectively, fluid streams 3026), which penetrate adsorptive block 3010 further creating streamlines 3028a-3028n (collectively, streamlines 3028) in a direction substantially perpendicular to the plane of the layers of planarly cohesive media comprising adsorptive block 3010.

Streamlines 3028 flow from top planar surface of adsorptive block 3010 traversing depth, D, of adsorptive block 3010, and are turned 90° and collected by second planar distributor 3003 at bottom of planar surface of adsorptive block 3010 in subeffluent streams 3023a-3023n (collectively, subeffluent streams 3023), which are combined to form an effluent stream 3025. Effluent stream 3025 further combines with main effluent stream 3021, originating from adsorptive devices stacked on top of adsorptive device 3010 (not shown), to form main effluent stream 3029, which is further directed to subsequent adsorptive devices (not shown). Point 3018 in first planar distributor 3001 is the stagnation point of feed stream 3026 by virtue of peripheral seal 3004", which prevents fluid communication between first planar distributor 3001 and second distribution passageways 3007. Likewise, point 3019 in second planar distributor 3003 is the stagnation point of effluent stream 3025 by virtue of peripheral seal 3004', which prevents fluid communication between second planar distributor 3003 and first distribution passageways 3005.

FIG. 30A and FIG. 30B are top and bottom plan views of first and second planar distributors 3001 and 3003, respectively, with arrows representing the direction and magnitude of fluid flow within the planar distributors. Referring to FIG. 30A, first planar distributor 3001 comprises peripheral seal 3004 sealing the pressurized fluid within the distributor. First distribution passageways 3005a-3005n (collectively, distribution passageways 3005) are in fluid communication with first planar distributor 3001 at first end 3015 of adsorptive device, enabling feed stream 3022 to enter first planar distributor 3001; feedstream 3022 is a portion of main feed stream (not shown) flowing through distribution passageways 3005. Feed stream 3022 gradually diminishes in magnitude as it traverses from first end 3015 of adsorptive device within first planar distributor 3001 towards second end 3017 of adsorptive device by virtue of being in intimate contact with adsorptive block 3010 (not shown), splitting up into a plurality of streams flowing into adsorptive block 3010 (streamlines 3028 in FIG. 29A and FIG. 29B). By the time feed stream 3026 approaches the end of the first planar distributor 3001 it becomes very small as represented by arrows 3026n, being fully consumed by the time it reaches the stagnation point 3018. Referring to FIG. 30B, second planar distributor 3003 comprises peripheral seal 3004 sealing the pressurized fluid within the distributor. Second distribution passageways 3007a-3007n (collectively, distribution passageways 3007) are in fluid communication with second planar distributor 3003 at second end 3017 of adsorptive device, enabling effluent stream 3025 to exit second planar distributor 3003. Effluent stream 3025 gradually increments in magnitude as it traverses from first end 3015 of adsorptive device within second planar distributor 3003 towards second end 3017 of adsorptive device by virtue of being in intimate contact with adsorptive block 3010 (not shown), collecting a plurality of streams flowing from adsorptive block 3010 (streamlines 3028 in FIG. 29A and FIG. 29B). Likewise, there is no flow at stagnation point 3019 at first end of second planar distributor 3003.

FIG. 31 is a cross-sectional side view of adsorptive device assembly 3200 comprising top end plate 3202, bottom end plate 3204 and a stack of adsorptive devices 3000a-3000n (collectively, adsorptive devices 3000). Adsorptive devices 3000 are held in place by top end plates 3202 and bottom end plates 3204 respectively, attached to each other by tie rods (not shown) or by some other means of supporting the hydraulic pressure generated within adsorptive devices 3000 well known to those skilled in the art, e.g., hydraulic cylinders or clamps (not shown). Gasket 3210 seals interface between top end plate 3202 and top planar surface of first adsorptive device 3000a, gasket 3211 seals interface between bottom end plate 3204 and bottom planar surface of last adsorptive device 3000n, and gaskets 3212a-3212n (collective, gaskets 3212) seal interfaces between top and bottom planar surfaces of adjacent adsorptive devices 3000 stacked within adsorptive device assembly 3200. Gasket 3210 has openings at first end of adsorptive devices 3015 that line up with first distribution passageways 3005 and none in second end 3017 of adsorptive devices, whereas gasket 3211 has openings at second end of adsorptive devices 3017 that line up with second distribution passageways 3007 and none in first end of adsorptive devices 3015; in this embodiment these gaskets are identical but not symmetrical requiring that they be installed 180° from each other. In contrast, gaskets 3212 have openings at both first and second ends of adsorptive devices 3015 and 3017 that line up with first and second distribution passageways 3005 and 3007, respectively; in this embodiment these gaskets are symmetrical so it does not matter which way they are installed. Top end plate 3202 has internal distributors 3205 to distribute main feed stream into each passageway of first distribution passageways 3005; likewise, bottom end plate 3204 has internal distributors 3205 to collect main effluent stream from each passageway of second distribution passageways 3007. Optional filler 3206 may be inserted into first distribution passageways of adsorptive device 3000n to eliminate dead volume at bottom of first distribution passageways; likewise, optional filler 3208 may be inserted into second distribution passageways of adsorptive device 3000a to eliminate dead volume at top of second distribution passageways. In other embodiments gaskets 3212 may be integrated into each adsorptive device 3000 for convenience in stacking, or they may be separate discrete components as shown in this embodiment to be added during stacking.

Figure 32:
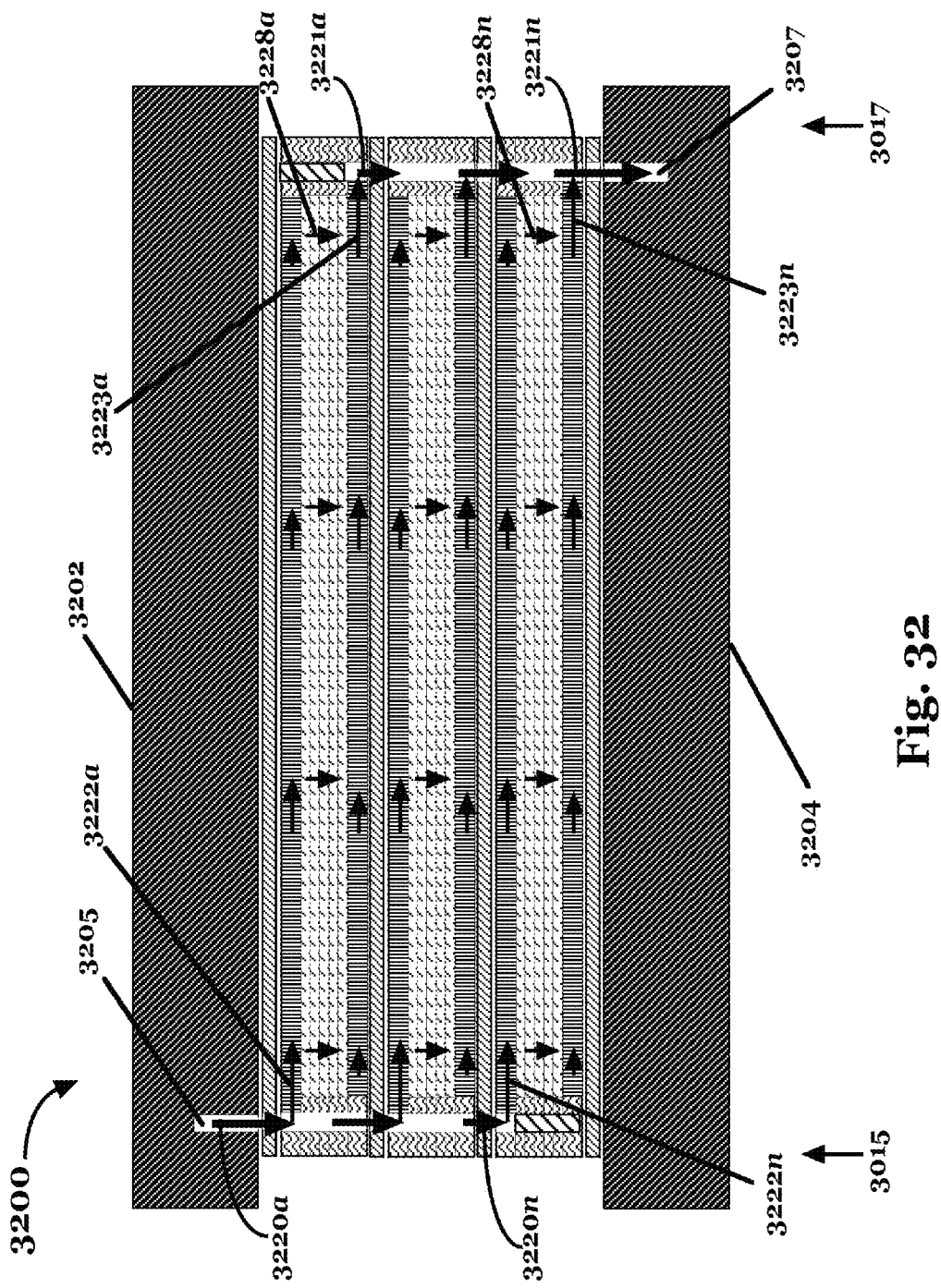
FIG. 32 is a cross-sectional side view of a Chromassette-S adsorptive device assembly identical to that of FIG. 31 with arrows representing the direction of fluid flow in use.

FIG. 32 is a cross-sectional side view of adsorptive device assembly 3200 in operation, with arrows representing schematically the flow direction and magnitude of feed and effluent streams. Main feed streams 3220a-3220n (collectively, main feed streams 3220) gradually decrease in magnitude as they travel from top end plate 3202 to bottom end plate 3204; likewise main effluent streams 3221a-3221n (collectively, main effluent streams 3221) gradually increase in magnitude as they travel from top end plate 3202 to bottom end plate 3204. Main feed stream 3220 is delivered to stack of adsorptive devices 3000 by feed distributor 3205 of top end plate 3202. Feed streams 3220 enter first distribution passageways of each adsorptive device delivering feed stream 3222 into first planar distributor of each adsorptive device, creating streamlines 3228 of each adsorptive device, which are collected by second planar distributor of each adsorptive device to form effluent stream 3223 of each adsorptive device, which flow into second distribution passageways of each adsorptive device forming main effluent stream 3221. Effluent stream 3221n is collected by effluent collector 3207 of bottom end plate 3204.

TWO KINDS OF PLANAR DISTRIBUTORS

Generally, embodiments include two types of planar distributors. A first type (referred to as a Type-I planar distributor) has a porous sheet of substantially uniform thickness, hydraulic permeability and porosity, and a plurality of interconnected flow passages. FIG. 30A and FIG. 30B are examples of a Type-I planar distributor. The fluid permeates the porous structure of the distributor with the flow velocity gradually and continuously decreasing when used as a first planar distributor for distributing fluid (e.g., as shown in the embodiments of FIGS. 29-31), or conversely, with the flow velocity gradually and continuously increasing when used as a second planar distributor for collecting the streams (e.g., as shown in the embodiments of FIGS. 29-31). Type-I planar distributors can be fabricated from non-woven webs, woven webs, perforated or embossed plastic sheets or metal sheets/films, from sintered plastic or metal particles, the important aspect being that they have uniform flow properties and reasonable hydraulic permeability along the planar dimension. Reasonable hydraulic permeability generally indicates low enough permeability such that the low-pressure drop generated by the fluid flow within the planar distributor is sufficiently low.

A second type of planar distributor (referred to as a Type-II distributor) comprises an array of interconnected flow channels or passageways that direct and distribute the fluid in a prescribed manner according to the dimensions of the channels and to the topology of the array.

Figure 33A:
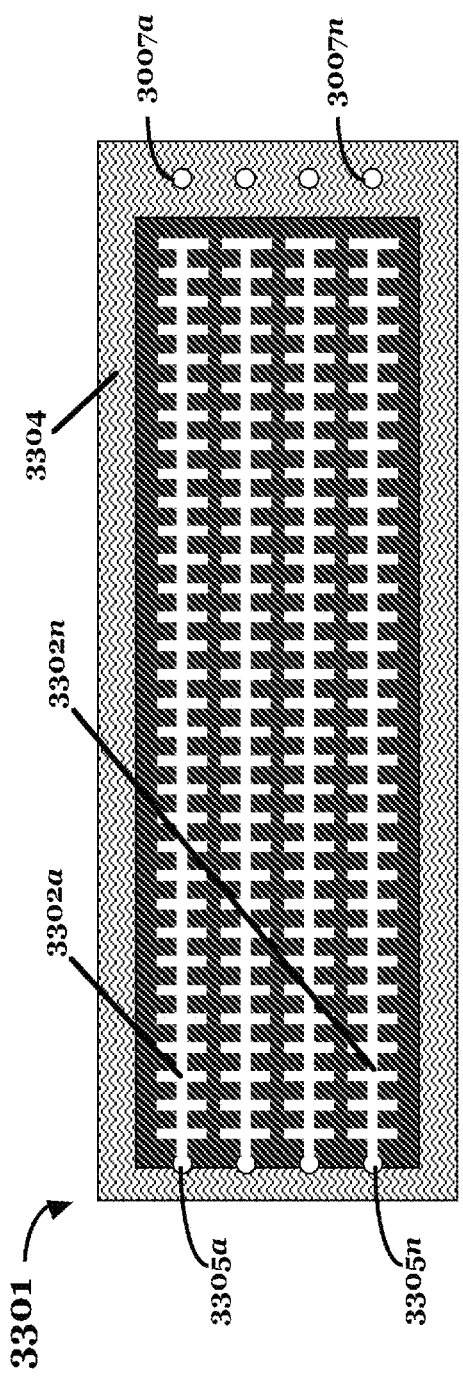
FIGS. 33A-33B are schematic diagrams of plan views of planar distributors.

FIG. 33A shows a Type-II planar distributor 3310 comprising peripheral seal 3304 first distribution passageways 3305a-3305n (collectively, first distribution passageways 3305), second distribution passageways 3307a-3307n (collectively, second distribution passageways 3307), and channel arrays 3302a-3302n (collectively, channel arrays 3302).

Figure 33B:
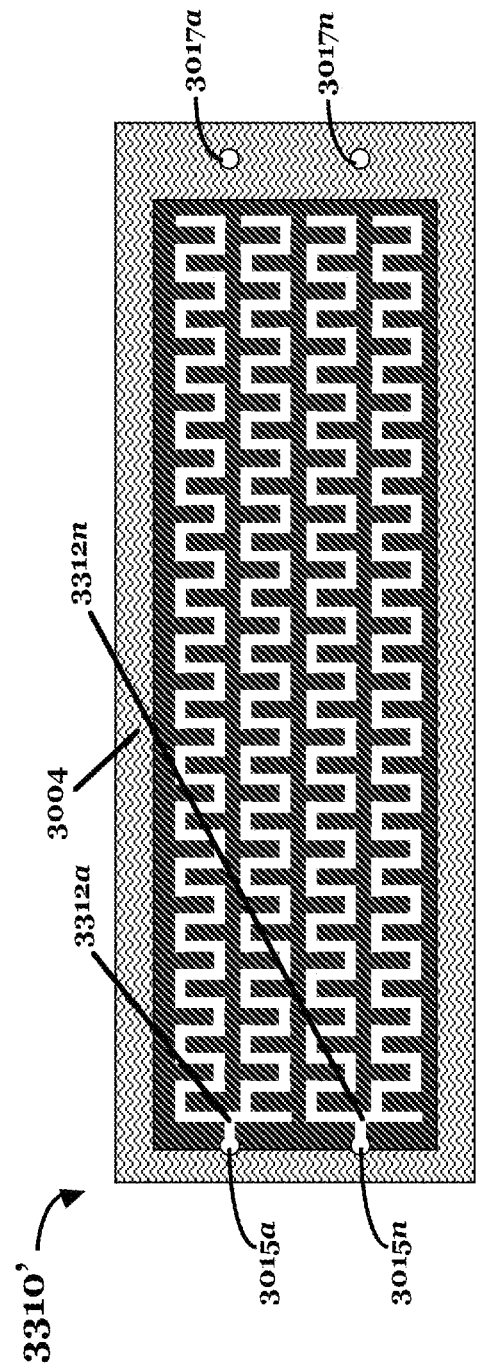

FIG. 33B shows an alternative embodiment of a Type-II planar distributor 3310' having fewer first and second distribution passageways 3315 and 3317, respectively, than the planar distributor 3310 of FIG. 33A and fewer but more elaborate channel arrays 3312. Planar distributors 3301 and 3310 are relatively thin and are in intimate contact with the top or bottom surface of adsorptive block (not shown. Type-II planar distributors may be made by one of many methods known to those skilled in the art, e.g., by plastic molding methods, by perforating a metal plate or plastic film, by etching a metal film, etc. The important aspect being that the planar distributor be of substantially uniform thickness, and that the fluid is uniformly distributed to or collected from the adsorptive block.

A special class of Type-II planar distributor promotes a uniform distribution by virtue that all possible flow passages formed by the channel array have the same length. Such distributors are described in detail in US patent application publication 2012/0097591, and shall be referred to as planar isoflo distributors.

Figure 34:
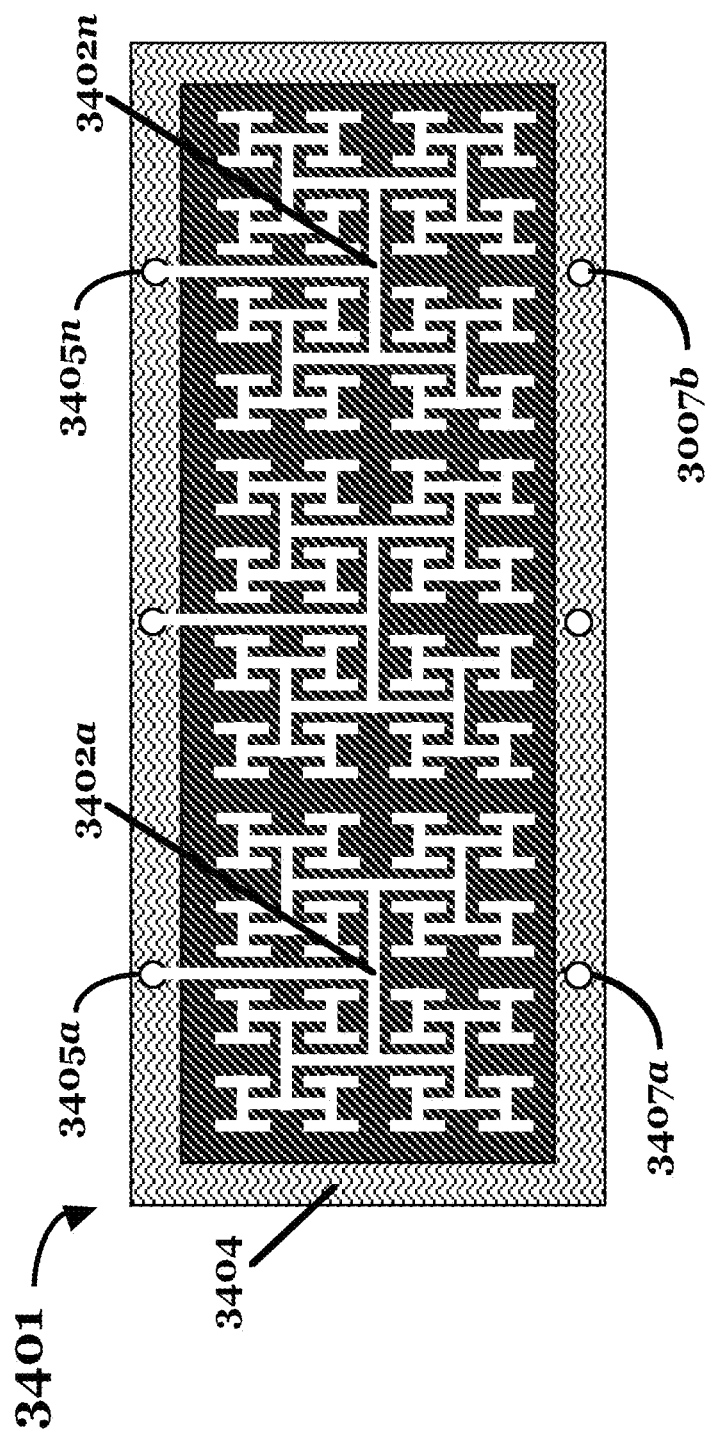
FIG. 34 is a plan view of an exemplary planar isoflo distributor.

FIG. 34 is a plan view of an exemplary planar isoflo distributor. Planar distributor 3401 comprises peripheral seal 3404, first distribution passageways 3405a-3405n (collectively, first distribution passageways 3405), second distribution passageways 3407a-3407n (collectively, second distribution passageways 3407) and channel arrays 3402a-3402n (collectively, channel arrays 3402). All flow passageways in channel arrays 3402 comprise a branched structure wherein the length of the flow path in every flow passage of channel arrays 3402 have the same length. This is accomplished by bifurcating each branch into two identical sub-branches, in this example, a total of five bifurcations, producing a total of 32 distribution or collection points. In this embodiment the channel array has a square footprint; in other embodiment it may have a rectangular footprint; in still other embodiments it may have a circular footprint. The important aspects of isoflo channel arrays is that they are branched, each branch bifurcates in two sub-branches, and at every bifurcation level each sub-branch is substantially an identical twin to the other sub-branch.

In general it should be noted that good chromatographic practice dictates that the hold-up volume of the planar distributors should be small compared to that of the adsorptive block to which it is distributing or from which it is collecting fluid.

OTHER EMBODIMENTS

Good adsorptive and chromatographic practice dictates that all fluid streamlines have the same length and residence time in order to reduce the dispersion of an adsorptive bed; these may be referred to as isoflo conditions. The geometrical symmetry that exists between the feed and effluent streams in the embodiments shown in FIGS. 28A-31 is conducive to conditions that generate streamlines of the same length. Specifically, the first and second distribution passageways are on opposite ends of the adsorptive device, the fluid flow in the first and second planar distributors is in the same direction, and the fluid flow in the first and second distribution passageways are in the same direction. Such a geometrical and flow configuration, in conjunction with uniform hydraulic properties of all the flow passages, the planar distributor, and the adsorptive block ensures that every flow streamline within the adsorptive device has the same length and residence time.

In other embodiments it may be advantageous to feed and collect all streams in either the top or bottom end plates, making the connectivity simpler and more convenient. In still other embodiments it may be advantageous to have the first and second distribution passageways on adjacent ends of the adsorptive devices (rather than on opposite ends) and possibly even on the same end. These situations do not conform to the symmetry that creates the isoflo condition and therefore, may not be optimal for chromatographic dispersion. However, the unfavorable impact of these non-optimal configurations on dispersion may be minimal, or tolerable, if the on the combined fluid volume of the distributors (i.e., the fluid volume of the distribution passageways plus the fluid volume of the planar distributors) is small compared to the total fluid volume of the adsorptive block; in some embodiments the combined fluid volume of the distributors is less than 10% of the fluid volume of the adsorptive block; in other embodiments the combined fluid volume of the distributors is less than 5% of the fluid volume of the adsorptive block. Therefore, such embodiments may still be useful.

Just as shown in FIG. 11A and FIG. 11B, adsorptive devices comprising planar distributors to induce perpendicular flow in the adsorptive block can be fabricated with a double-sided configuration, wherein the first distribution passageways are centered in the adsorptive device feeding fluid to both sides of the adsorptive bed (in this case, left and right sides), whereas the second distribution passageways are on opposite ends collecting fluid. Of course, FIG. 11A and FIG. 11B do not show the peripheral seal encapsulating the distribution passageways in the first planar distributor, which is necessary for this embodiment.

Multiplexed adsorptive devices as shown in FIG. 15A and FIG. 15B are also possible as well as non-rectangular footprints as shown in some of the earlier figures.

FIGS. 35A-C show a device with improved adhesion and sealing performance of the peripheral seals. FIG. 35A shows a plan view of planarly cohesive media 3502 with calendered edge 3514, wherein the porosity of media 3502 has been substantially reduced by mechanically pressing calendered edge 3514 with or without heat. FIG. 35B shows a magnified cross-section of calendered edge 3514, which remains attached to the adsorptive media 3512, showing that the thickness of calendered edge has been substantially reduced. FIG. 35C shows a cross-sectional view of peripheral seal 3504 adhered to calendered edge 3414; peripheral seal 3504 may be molded or cast in place by suitable methods well known to those skilled in the art. The increased surface area of the region between peripheral seal 3504 and calendered edge 3514 improves the adhesion and the sealing performance of peripheral seal 3504. The step created between the calendered edge 3514 and the adsorptive media 3512 further creates a well-defined boundary for limiting the region onto which the peripheral seal is applied. In this embodiment a peripheral seal is applied on each planarly cohesive layer, followed by these being stacked to form an adsorptive block. In other embodiments multiple layers of planarly cohesive media 3502, each with a calendered edge, are stacked and peripheral seal 3504 is applied to all the layers simultaneously resulting in an adsorptive block with a monolithic peripheral seal.

Although FIG. 27-35 describing Chromassette-S adsorptive devices specifically described embodiments utilizing cohesive web media, embodiments utilizing bead-based adsorptive media are also possible. In Chromassette-S embodiments utilizing bead-based media a structural scaffold of planarly cohesive webs according to FIG. 17-23 would be used with the void space packed with beads. Such bead-based Chromassette-S adsorptive devices require that the structural scaffold of planarly cohesive webs be fabricated with a peripheral seal (or a precursor to a peripheral seal) followed by packing it with beads to form an adsorptive block prior to the application of the first and second planar distributors. As described above, bead-based devices disclosed herein utilize packing retainers preferably on both the feed and eluent ends of the device to keep the bed of beads fixed and stationary. In contrast, web-based Chromassette-S adsorptive devices may be fabricated by having its peripheral seal applied at once (i.e., to the adsorptive block and the first and second planar distributors at once).

Other embodiments of devices suitable for bead-based adsorptive media utilize monolithic scaffolds. A monolithic scaffold is a planarly cohesive scaffold interconnected in all three dimensions forming a three-dimensional interconnected lattice (hereafter "interconnected lattice") having structural elements, or struts, and forming an interconnected void space. In other words, two dimensions define the cohesion plane of planarly cohesive media (referred to as the "x-y plane") and the third dimension is the z-coordinate and a monolithic scaffold is one where the cohesion planes are all interconnected in the z-coordinate.

Embodiments fabricated with monolithic scaffolds have some benefits over devices fabricated with scaffolds built with planarly cohesive webs. Monolithic scaffolds do not allow the adsorptive beads to move in the z-direction before the adsorptive device is mounted into a holder. Also, adsorptive devices fabricated with monolithic scaffolds enable the possibility of operating such devices without a holder having end plates to support it. Furthermore, monolithic scaffolds may be fabricated using methods that enable the integration of other elements (e.g., peripheral seals, distribution passageways, packing retainers), thereby simplifying the fabrication of bead-based adsorptive devices, as for example, using 3D-printing methods.

Figure 36A:
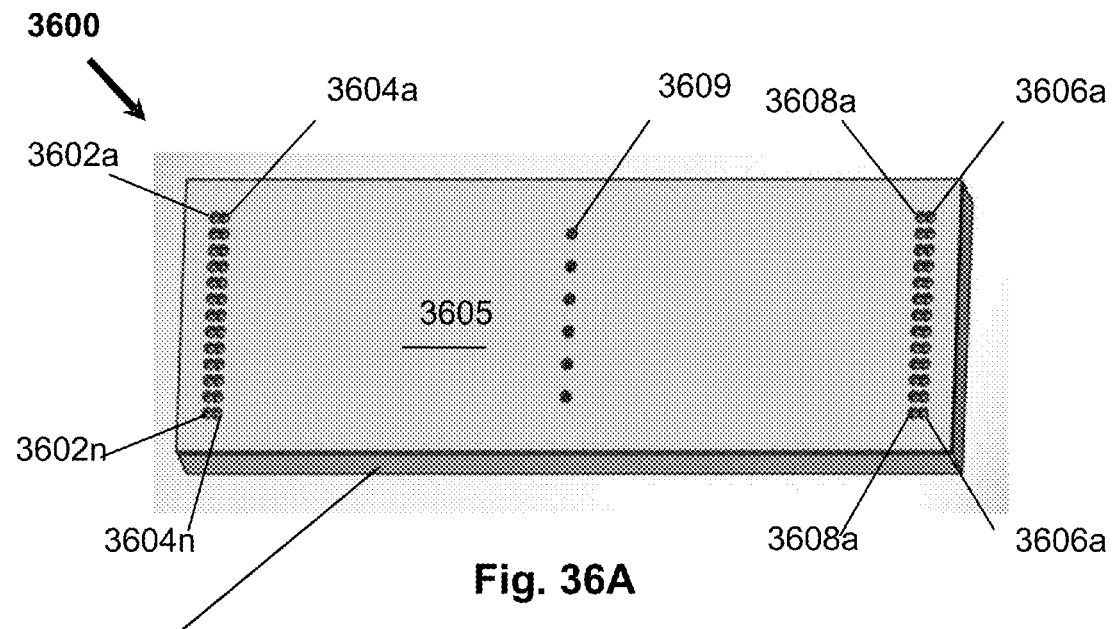
FIG. 36A is an isometric view of a monolithic scaffold fabricated with 3D-printing according to embodiments disclosed herein.

Now, referring to FIG. 36A, an exemplary monolithic scaffold 3600 includes a peripheral seal 3601, an interconnected lattice 3603 (FIG. 36B), a top plate 3605 and a bottom plate (not shown) on opposite side of top plate. The monolithic scaffold 3600 further includes passageways 3602a~3602n (collectively passageways 3602) and passageways 3606a~3606n (collectively passageways 3606) which provide distribution of feed stream and collection of eluent stream, respectively and passageways 3604a~3604n (collectively passageways 3604) and passageways 3608a~3608n (collectively passageways 3608) which provide for insertion of packing retainers (not shown) on feed and eluent ends, respectively. In this embodiment packing retainers are cylindrical porous rods having a diameter approximately equal to the diameter of passageways 3604 and 3608, a length equal to the depth of the passageways, and inserted into the passageways; packing retainers may be fabricated in plastic or metal or ceramic or glass. Once inserted, the packing retainers remain in place by virtue of a slight interference between the inside diameter of the passageways and the outside diameter of the porous rods. After the packing retainers are in place, passageways 3609 on top plate 3605 may be used to insert the adsorptive beads into the void space within the interconnected lattice by slurry packing or other methods known in the art of packing adsorptive beds. Alternatively, distribution passageways 3602 are used to insert the beads, and passageways 3604 remain open and the cylindrical porous rods are inserted after the void space within the interconnected lattice is fully packed with adsorptive beads.

Figure 36B:
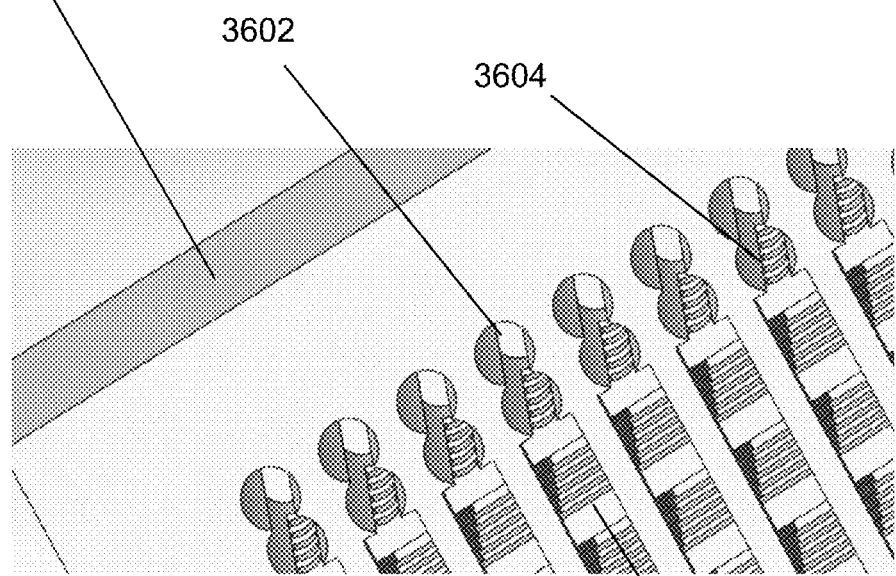
FIG. 36B is a magnified view of the feed end of the monolithic scaffold of FIG. 36A without top and bottom plates.
Figure 37A:
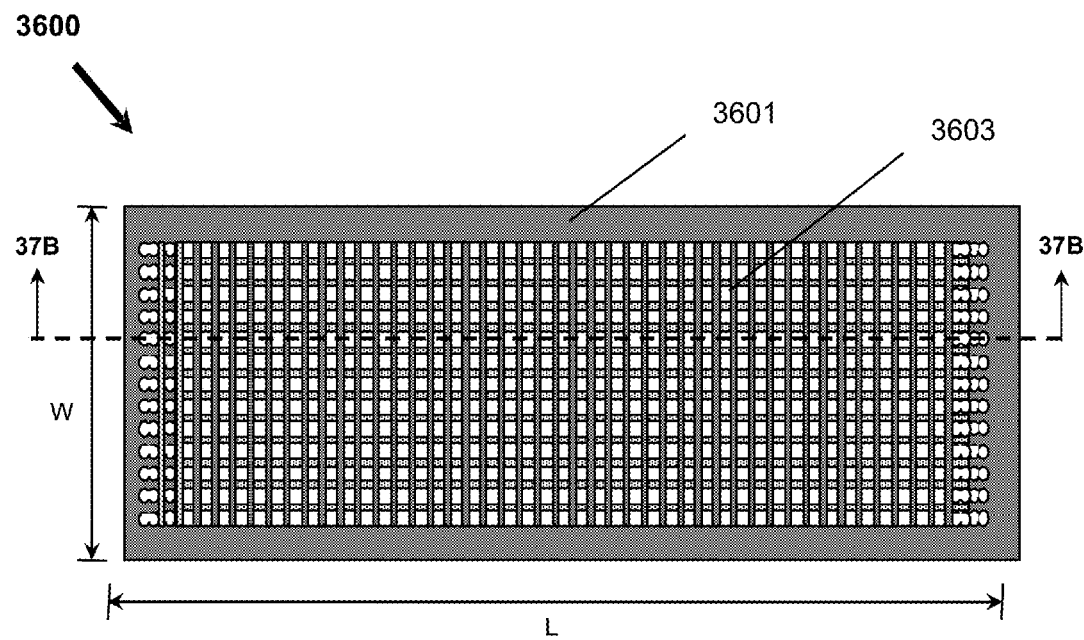
FIG. 37A is a cross-sectional top view of the monolithic scaffold of FIG. 36A.

As shown in FIG. 36B, passageways 3602 are in fluid communication with passageways 3604, which are also in fluid communication with the interconnected lattice 3603. In preparation for use, passageways 3604 accept cylindrical porous rod (not shown) forming a packing retainer by virtue of being located between the void space of the interconnected lattice 3603 (packed with adsorptive beads) and the distribution passageways 3602. Once the porous rods are inserted the adsorptive beads are retained and the adsorptive bed packed in the void space cannot move, providing a stationary adsorptive phase. FIG. 37A shows additional details of the monolithic scaffold 3600 including relative placement of the interconnected lattice 3603 and the peripheral seal 3601. Here the monolithic scaffold 3600 has an overall length, L and an overall width, W.

Figure 37B:
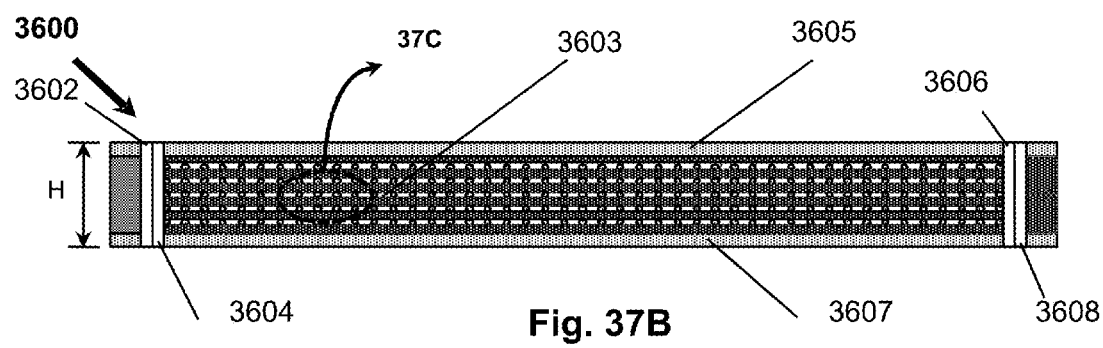
FIG. 37B is a cross-sectional side view of the monolithic scaffold of FIG. 36A.

Referring to FIG. 37B, the monolithic scaffold 3600 includes top and bottom plates 3505 and 3507, respectively, that together with peripheral seal 3601 contain interconnected lattice 3603. In operation the passageways 3602 are used for distribution of the feed stream and passageways 3604 are used for collection of the eluent stream. Passageways 3604 and 3608 accept the porous cylindrical rods (not shown) to form packing retainers on both feed and eluent end of the monolithic scaffold 3600, respectively.

Figure 37C:
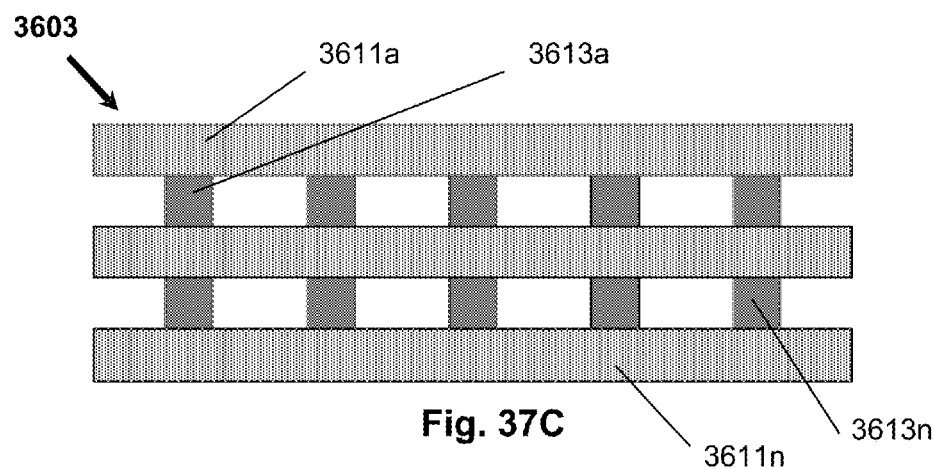
FIG. 37C is a magnified cross-sectional side view of the interconnected lattice included in the monolithic scaffold of FIG. 36A.

Referring to FIG. 37C, interconnected lattice 3603 includes structural elements 3611a~3611n along the length or x-coordinate of the monolithic scaffold in the form of filaments or struts (collectively struts 3611), and structural elements 3613a~3613m along the width or y-coordinate of the monolithic scaffold 3600 in the form of filaments or struts, (collectively struts 3613). In one embodiment, struts 3611 and 3613 are bonded to each other, creating a planarly cohesive scaffold and further imparting to the scaffold cohesiveness in the z-coordinate thereby creating a monolithic scaffold. In this embodiment struts 3611 and 3613 have a rectangular cross-section; however, other cross-sections are possible, for example, circular or elliptical or combinations thereof. Furthermore, the interconnected lattice 3603 has a regular "square" pattern wherein struts 3611 are stacked in the same vertical location relatively to each other. However it is understood that other patterns are possible, including that struts may not be disposed in a regular pattern.

Figure 38:
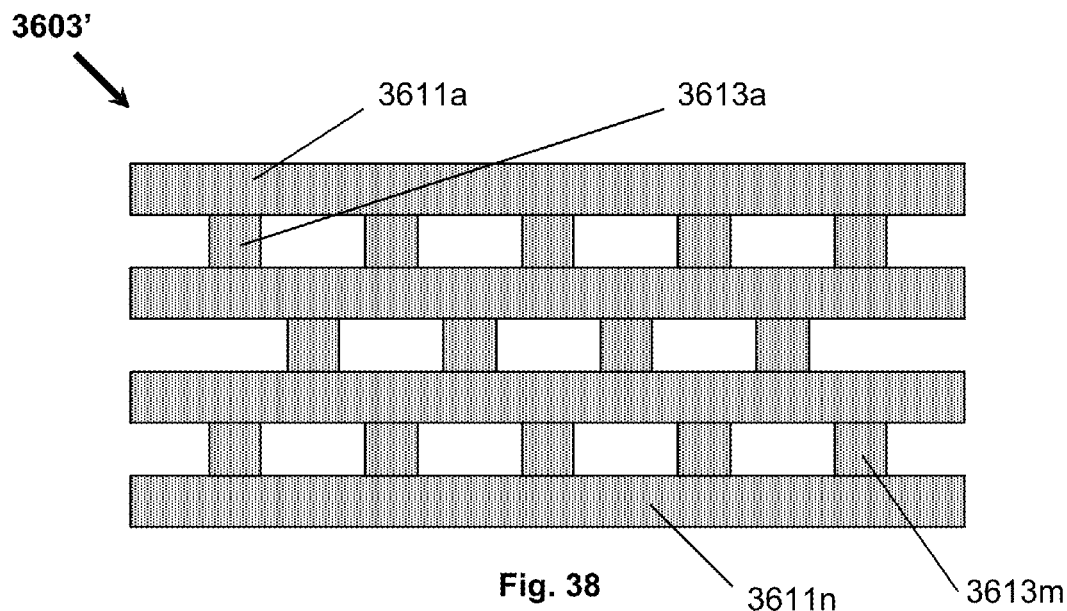
FIG. 38 is a magnified cross-sectional side view of an alternative interconnected lattice having a staggered pattern according to embodiments disclosed herein.

Referring to FIG. 38, and alternative interconnected lattice 3603' includes struts 3613 in the y-direction which are staggered from one layer to the next, forming a "staggered" structure. Likewise, struts 3611 in the x-direction may also be staggered (not shown). Interconnected lattice 3603' also has a regular pattern similar to the lattice 3603.

It should be appreciated that many different patterns for the interconnected lattice 3603 can be used, an important characteristic being that the interconnected lattice 3603 include an interconnected void space to accept the adsorptive beads, and that the size and density of the struts 3611 and 3613 need to be sufficient to provide the monolithic scaffold 3600 sufficient strength to withstand the hydraulic forces during operation. Exemplary monolithic scaffolds have a void volume greater than 25%, preferably greater than 50% and most preferably greater than 65%, while simultaneously having a Young's modulus in the x-y plane exceeding 500 psi, preferably exceeding 1,500 psi and most preferably exceeding 5,000 psi. Furthermore, packing retainers may be inserted along the width of the device, along the y-coordinate, rather than along the z-coordinate; in this case passageways 3604 and 3608 to accept the packing retainers would be drilled from side-to-side rather than from top-to-bottom.

Figure 39:
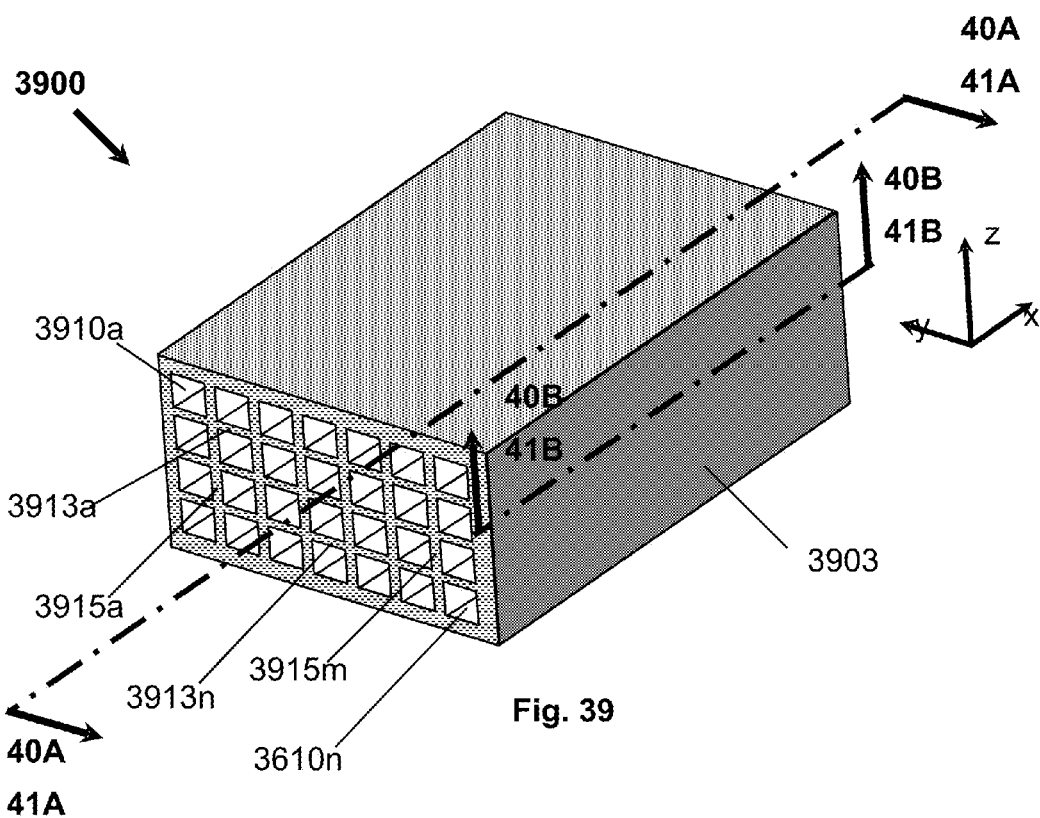
FIG. 39 is an isometric view of monolithic scaffold fabricated by extrusion processes.

Monolithic scaffolds suitable for bead-based media can also be made by extrusion methods. Referring to FIG. 39, monolithic scaffold 3900 is made by an extrusion process and comprises structural shell 3903 housing an array of channels 3910a-3910n (collectively channels 3910) oriented along the extrusion axis (in this case, the x-axis). The array of channels 3910 forms a structural lattice comprising plates in the (horizontal) x-y plane 3913a-3913n (collectively plates 3913) intersecting (vertical) x-z planes 3915a~3915m (collectively plates 3913). Shell 3903, plates 3913 and plates 3915 form an interconnected lattice, fused together as a monolithic scaffold by virtue of the extrusion process. In this embodiment, channels 3910 have a square cross-section and the channel array has a regular stacked layout. It is appreciated that other regular or irregular cross-sections (e.g., circular, triangular, rectangular, hexagonal) are also possible, as well as other layouts (e.g., staggered as well as irregular layouts). The channels in extrusion 3900 form the void space in which the bead-based adsorptive media is packed. It is also appreciated that the monolithic scaffold shown in FIG. 39 can also be fabricated by 3D-printing methods, but extrusion processes offer speed, cost and scaling advantages, as well as the choice of many other materials, including many of plastics, metals and ceramic materials.

Figure 40A:
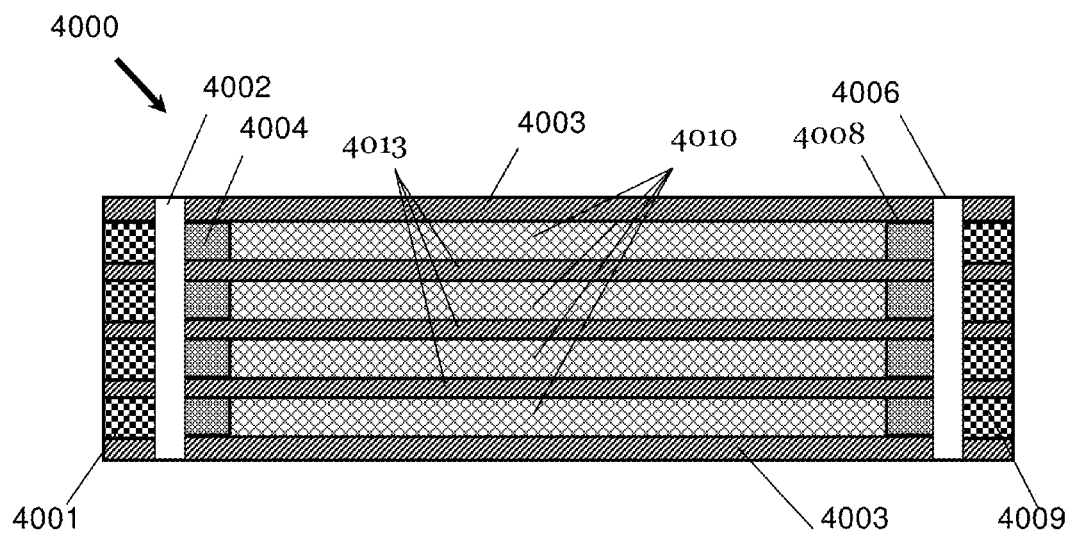
FIG. 40A is a cross-sectional side view of a device of this invention using the monolithic scaffold of FIG. 39.
Figure 40B:
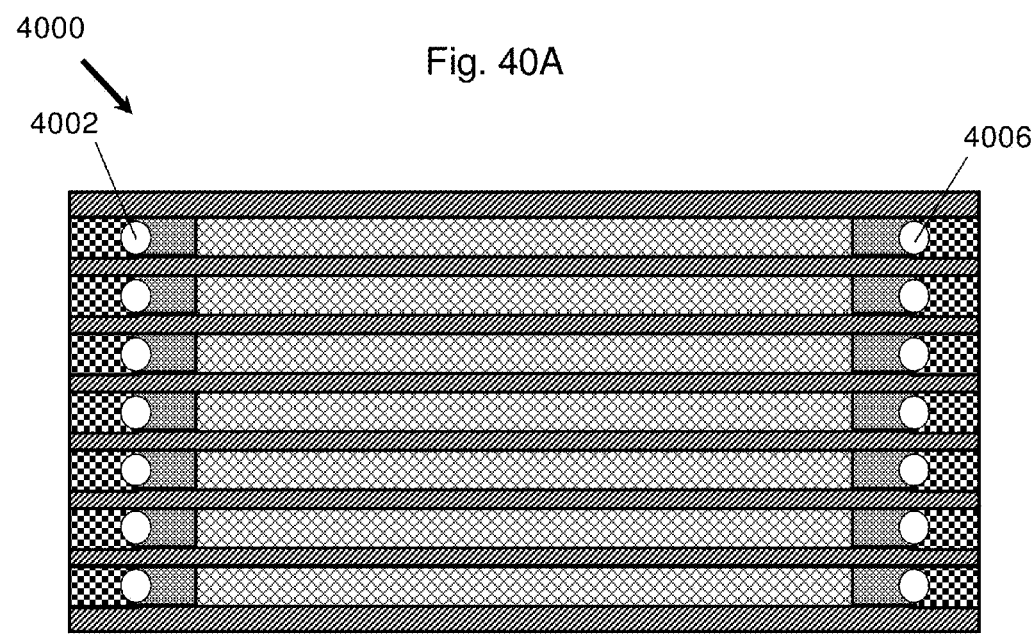
FIG. 40B is a cross-sectional top view of a device of this invention using the monolithic scaffold of FIG. 39.

Referring to FIG. 40A, adsorptive device 4000, fabricated with an extruded monolithic scaffold as shown in FIG. 39, comprises exterior shell 4003, channels 4010, plates 4013 along the x-y plane, plates along the x-z plane (not shown), packing retainers 4004 and 4008 on the feed and eluent ends of the device, respectively, passageways 4002 and 4006 for distribution of feed and collection of eluent, respectively, and peripheral seals 4001 and 4009 on the feed and eluent ends, respectively. One process for fabricating adsorptive device 4000 starts with extruded monolithic scaffold as shown in FIG. 39 cut to the desired length, with the following sequential steps: packing retainers 4008 are inserted on eluent end of device 4000; peripheral seal 4009 is applied on eluent end of device 4000 filling the channels 4010 between packing retainers 4008 and the eluent end of the device 4000; channels 4010 are packed with the desired adsorptive beads (not shown) by methods known to those skilled in the art; packing retainers 4004 are inserted on feed end of device 4000; peripheral seal 4001 is applied on feed end of device 4000 filling the channels 4010 between packing retainer 4002 and the feed end of the device 4000. Finally, as shown in FIG. 40B, passageways 4002 and 4006 are drilled from the top to the bottom of device 4000 to create feed distributors and eluent collectors, respectively.

Figure 41A:
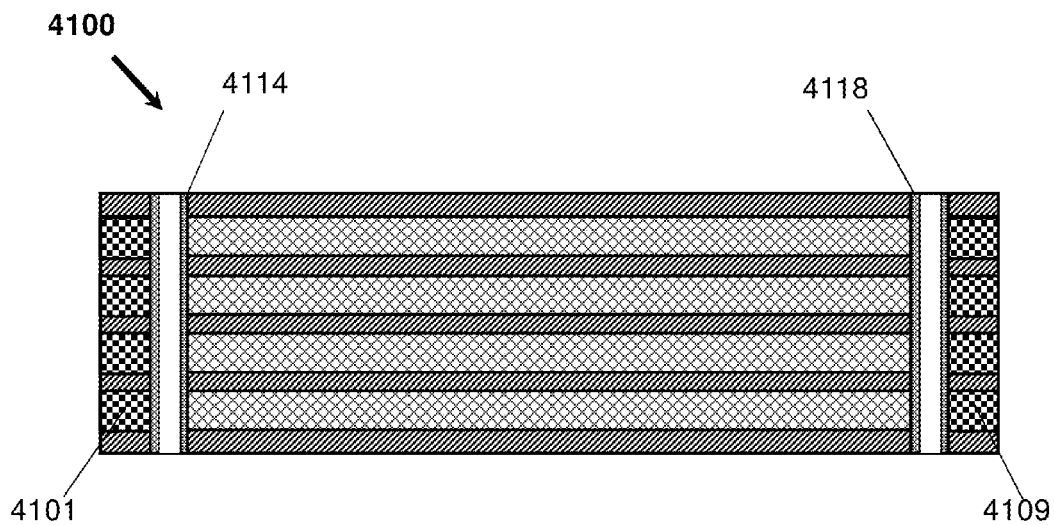
FIG. 41A is a cross-sectional side view of another embodiment of a device of this invention using the monolithic scaffold of FIG. 39.
Figure 41B:
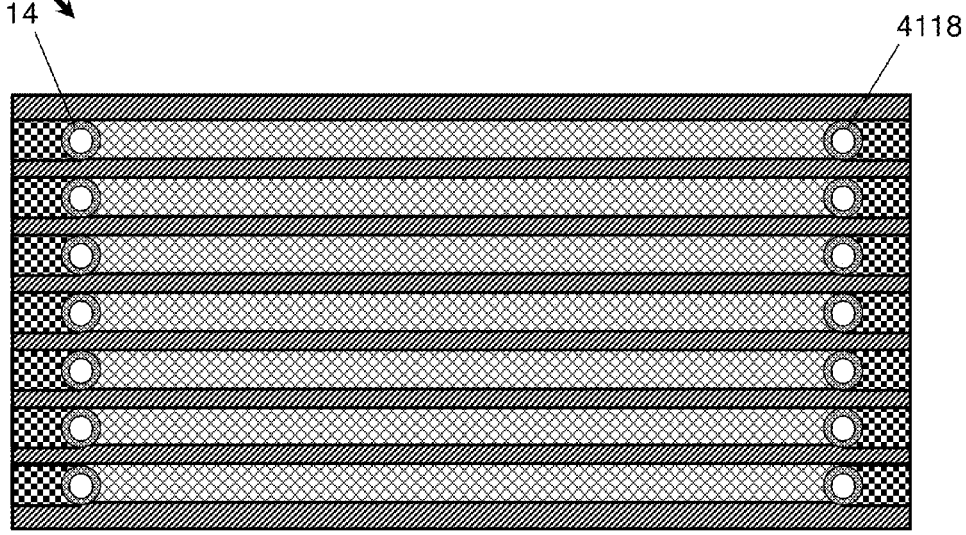
FIG. 41B is a cross-sectional top view of another embodiment of a device of this invention using the monolithic scaffold of FIG. 39.

Variations of the means of retaining the beads are possible. For example, FIGS. 41A and 41B show alternative embodiment 4100, wherein the packing retainers are hollow tubes with porous walls 4114 and 4118 comprising both the packing retainer and the distribution/collection passageways. In this embodiment peripheral seal 4101 and 4109 on the ends of the device may be applied before inserting the hollow tubes 4114 and 4118, followed by drilling of passageways large enough to accept the hollow tubes 4114 and 4118; alternatively, passageways to accept the hollow tubes 4114 and 4118 are drilled first, followed by insertion of the hollow tubes 4114 and 4118, followed by application of the peripheral seal to fill the channels between the hollow tubes and the ends of the device.

In still other embodiments monolithic scaffolds are fabricated by molding plates as exemplified in FIG. 19A-19C. Referring again to FIG. 19A-19C, after inserting packing retainers (not shown) and adding adsorptive beads 1214, the plates are stacked and bonded to each other. To obtain a monolithic scaffold, peripheral seals 1206 on each plate are bonded to peripheral seal 1206 on the plate stacked above it, whereas spacers 1214 are bonded on flat bottom 1220 of to the plate stacked above it.

Variations of the fabrication method of devices of this invention are also possible. For example; the beads may be packed from the eluent end, in which case the sealing of the feed end occurs before that of the eluent end; both ends of the adsorptive devices 4000 and 4100 may be sealed before packing the adsorptive beads, in which case new passageways in the middle of the channels would be created to introduce the beads; etc. The elements of devices having monolithic scaffolds include planar cohesion in the x-y plane sufficient to withstand the operating pressures, channels packed with beads, packing retainers and peripheral seals on both feed and eluent ends of the device, and passageways on both ends of the device for the distribution of feed stream and collection of the eluent stream.

It is understood that although the embodiments described herein relate specifically to bio-molecular applications, the principles, practice and designs described herein are also useful in other applications, including the manufacture of vaccines and biopharmaceuticals. All literature and similar material cited in this application, including, patents, patent applications, articles, books, treatises, dissertations and web pages, regardless of the format of such literature and similar materials, are expressly incorporated by reference in their entirety. In the event that one or more of the incorporated literature and similar materials differs from or contradicts this application, including defined terms, term usage, described techniques, or the like, this application controls.

The section headings used herein are for organizational purposes only and are not to be construed as limiting the subject matter described in any way. While the present invention has been described in conjunction with various embodiments and examples, it is not intended that the present teachings be limited to such embodiments or examples. On the contrary, the present invention encompasses various alternatives, modifications, and equivalents, as will be appreciated by those of skill in the art. While the teachings have been particularly shown and described with reference to specific illustrative embodiments, it should be understood that various changes in form and detail may be made without departing from the spirit and scope of the teachings. Therefore, all embodiments that come within the scope and spirit of the teachings, and equivalents thereto are claimed. The descriptions and diagrams of the methods of the present teachings should not be read as limited to the described order of elements unless stated to that effect.

The claims should not be read as limited to the described order or elements unless stated to that effect. It should be understood that various changes in form and detail may be made without departing from the scope of the appended claims. Therefore, all embodiments that come within the scope and spirit of the following claims and equivalents thereto are claimed.

What is claimed is:

1. An adsorptive bed to receive a liquid comprising:
   a housing comprising a peripheral seal;
   an interconnected lattice disposed within the housing and connected to the peripheral seal and comprising
      a plurality of layers, each layer disposed in a plane perpendicular to the peripheral seal;
      a plurality of open cells formed within the interconnected lattice comprising the plurality of layers;
   a packed adsorptive chromatographic bed comprising a plurality of adsorptive chromatographic beads disposed in each of the plurality of open cells; and
   wherein the interconnected lattice is disposed to restrict movement of the plurality of adsorptive chromatographic beads, support the packed adsorptive chromatographic bed, absorb tensile stress induced by a hydraulic pressure within the packed adsorptive chromatographic bed, absorb compressive stress induced on the plurality of adsorptive chromatographic beads by hydraulic pressure gradients along a direction of the liquid flowing parallel to a plurality of planes of the plurality of layers and transfer a portion of the induced tensile stress and the induced compressive stress to the peripheral seal of the housing.

2. The adsorptive bed of claim 1, wherein each layer of the plurality of layers comprises a separator sheet forming a plurality of separator sheets, each of the plurality of separator sheets being in intimate contact with adjacent separator sheets of the plurality of separator sheets.

3. The adsorptive bed of claim 2, wherein each separator sheet of the plurality of separator sheets comprises a plurality of rigid structural members comprising one of:
   a woven screen;
   a molded plate;
   an extruded sheet; and
   a perforated plate.

4. The adsorptive bed of claim 1, wherein the interconnected lattice has a tensile Young's modulus greater than 5000 psi.

5. The packed adsorptive chromatographic bed of claim 4, wherein the packed adsorptive chromatographic bed supports a liquid flow velocity greater than 150 cm/hour.

6. The adsorptive bed of claim 1, wherein each of the plurality of open cells has a characteristic diameter at least ten times larger than an average diameter of each of the plurality of adsorptive beads.

7. The adsorptive bed of claim 1, wherein each of the plurality of adsorptive chromatographic beads has a diameter of less than 100 microns.

8. The adsorptive bed of claim 1 wherein the interconnected lattice is a monolithic stress absorbing interconnected lattice and the monolithic stress absorbing interconnected lattice further comprises:
   a plurality of passageways for distribution of feed stream fluidly coupled to the plurality of open cells;
   a plurality of passageways for collection of eluent stream fluidly coupled to the plurality of open cells; and
   a plurality of packing retainers fluidly disposed between corresponding passageways of the plurality of passageways for collection of eluent stream and the plurality of open cells.

9. A chromatographic method to process a liquid comprising:
   providing an adsorptive bed comprising:
      a housing comprising a peripheral seal;
      an interconnected lattice disposed within the housing and connected to the peripheral seal and comprising
         a plurality of layers, each layer disposed in a plane perpendicular to the peripheral seal;
      a plurality of open cells disposed within the interconnected lattice formed by the plurality of layers;
      a packed adsorptive chromatographic bed comprising a plurality of adsorptive chromatographic beads disposed in each of the plurality of open cells;
   wherein the interconnected lattice is disposed to restrict movement of the plurality of adsorptive chromatographic beads, support the packed adsorptive chromatographic bed, absorb tensile stress induced by a hydraulic pressure within the adsorptive chromatographic bed, absorb compressive stress induced on the plurality of adsorptive chromatographic beads by hydraulic pressure gradients along a direction of the liquid flowing parallel to a plurality of planes of the plurality of layers and transfer a portion of the induced tensile stress and the induced compressive stress to the peripheral seal of the housing;
   processing the liquid; and
   operating at a pressure of greater than 50 psi.

10. The chromatographic method of claim 9 further comprising flowing the liquid through the packed adsorptive chromatographic bed at a velocity greater than 150 cm/hr.

11. The chromatographic method of claim 9, further comprising:
    adsorbing target solute in the packed adsorptive chromatographic bed;
    washing non-adsorbed solutes;
    releasing purified target solute; and
    conditioning the packed adsorptive chromatographic bed for a following purification cycle; and
    wherein the adsorbing, washing, releasing and conditioning steps have
       a rapid purification process cycle time less than about ten minutes.

12. The adsorptive bed of claim 1 further comprising:
    at least one valve fluidly coupled to the plurality of open cells controlling a flow rate of the liquid;
    at least one pump fluidly coupled to the at least one valve; and
    a rapid cycling controller coupled to the at least one pump and the at least one valve.

13. An adsorptive bed to receive a liquid flow comprising:
    a chromatographic cassette comprising:
       a peripheral seal;
       an interconnected lattice surrounded by and connected to the peripheral seal forming an interconnected void space;
       a first plate adjacent the peripheral seal;
       a second plate adjacent the peripheral seal, opposite the first plate;

wherein the first plate, the second plate and the peripheral seal enclose the interconnected lattice;
at least one distribution passageway having a first end disposed within the first plate and fluidly coupling the first end to the interconnected void space;
at least one packing retainer disposed within the chromatographic cassette and disposed between the interconnected void space and the at least one distribution passageway; and
a packed chromatographic adsorptive bed comprising a plurality of adsorptive chromatographic beads packed into the interconnected void space.

14. The adsorptive bed of claim 13, wherein of the at least one packing retainer comprises one of:
plastic porous rod;
metal porous rod;
ceramic porous rod; and
glass porous rod.

15. The adsorptive bed of claim 13 further comprising:
at least one second distribution passageway having a first end disposed within the second plate and a second end fluidly coupling the first end to the interconnected void space; and
a passageway fluidly coupling the second distribution passageway to the first distribution passageway.

16. The adsorptive bed of claim 15 further comprising at least one second chromatographic cassette adjacent the chromatographic cassette in a stacked configuration, wherein the second at least one distribution passageway of the chromatographic cassette is aligned with the at least one distribution passageway of the second chromatographic cassette having a first end disposed within the first plate of the second chromatographic cassette and a second end fluidly coupling the first end to the interconnected void space.

17. The adsorptive bed of claim 13, wherein the chromatographic cassette is a monolithic chromatographic cassette.

18. The adsorptive bed of claim 17, wherein the monolithic chromatographic cassette comprises a 3D printed chromatographic cassette.

19. The adsorptive bed of claim 18, further comprising a holder; and
wherein the monolithic chromatographic cassette is mounted in the holder.

20. The adsorptive bed of claim 13 further comprising at least one adsorptive bead insertion passageway disposed within the chromatographic cassette coupled to the interconnected void space and having a first end disposed within the first plate.

21. The adsorptive bed of claim 13, wherein the at least one distribution passageway is disposed to create a flow parallel to a plane including the first plate and parallel to a plane perpendicular to the peripheral seal.

22. The chromatographic method of claim 9, further comprising:
adsorbing target solute in the packed adsorptive chromatographic bed;
washing non-adsorbed solutes;
releasing purified target solute; and
conditioning the packed adsorptive chromatographic bed for a following purification cycle; and
wherein the adsorbing, washing, releasing and conditioning steps have a rapid purification process cycle time less than about thirty minutes.

* * * * *